US012800683B2

(12) United States Patent
Rizza et al.

(10) Patent No.: US 12,800,683 B2
(45) Date of Patent: Nov. 17, 2026

(54) APPARATUS FOR NUCLEAR MAGNETIC RESONANCE UTILIZING METAMATERIALS OR DIELECTRIC MATERIALS

(71) Applicants: UNIVERSITA' DEGLI STUDI DELL'AQUILA, L'Aquila (IT); CONSIGLIO NAZIONALE DELLE RICERCHE, Rome (IT)

(72) Inventors: Carlo Rizza, L'Aquila (IT); Angelo Galante, L'Aquila (IT); Marco Fantasia, Rome (IT); Marcello Alecci, L'Aquila (IT)

(73) Assignees: UNIVERSITA' DEGLI STUDI DELL'AQUILA, L'Aquila (IT); CONSIGLIO NAZIONALE DELLE RICERCHE, Rome (IT)

( * ) Notice: Subject to any disclaimer, the term of this patent is extended or adjusted under 35 U.S.C. 154(b) by 1140 days.

(21) Appl. No.: 17/629,137

(22) PCT Filed: Jul. 21, 2020

(86) PCT No.: PCT/IB2020/056842
§ 371 (c)(1),
(2) Date: Jan. 21, 2022

(87) PCT Pub. No.: WO2021/014354
PCT Pub. Date: Jan. 28, 2021

(65) Prior Publication Data
US 2022/0291311 A1 Sep. 15, 2022

(30) Foreign Application Priority Data
Jul. 22, 2019 (IT) ........................ 102019000012492

(51) Int. Cl.
*G01R 33/36* (2006.01)
*A61B 5/055* (2006.01)
(Continued)

(52) U.S. Cl.
CPC .......... *G01R 33/3635* (2013.01); *A61B 5/055* (2013.01); *G01R 33/341* (2013.01); *G01R 33/60* (2013.01)

(58) Field of Classification Search
CPC .. G01R 33/3635; G01R 33/341; G01R 33/60; G01R 33/36; G01R 33/34007;
(Continued)

(56) References Cited

U.S. PATENT DOCUMENTS

| | | | | |
|---|---|---|---|---|
| 6,101,015 A * | 8/2000 | Budil | G01R 33/60 398/1 |
| 2015/0260812 A1* | 9/2015 | Drake | G01R 33/34092 324/322 |

(Continued)

OTHER PUBLICATIONS

Xie, Yihong, Jianfeng Jiang, and Sailing He. "Proposal of cylindrical rolled-up metamaterial lenses for magnetic resonance imaging application and preliminary experimental demonstration." Progress In Electromagnetics Research 124 (2012): 151-162. (Year: 2012).*

(Continued)

*Primary Examiner* — Rishi R Patel
(74) *Attorney, Agent, or Firm* — Ferguson Case Orr Paterson

(57) ABSTRACT

An apparatus for increasing efficiency in the transmission phase and sensitivity in the reception phase, in specific regions of space, of magnetic resonance imaging technique by using at least one metamaterial or dielectric material is provided. Placing the metamaterial or dielectric material in a suitable geometry, in the space delimited by an RF coil and a sample, allows using the surface plasmonic resonances or equivalent dielectric resonances, induced in the metamaterial or dielectric material by the RF coil, to amplify the intensity of the magnetic field in the spatial region of the sample, improving the intensity of the signal transmission and/or the sensitivity of detection. The metamaterial or (Continued)

dielectric material is positioned outside the RF coil to maximize the amplification effect.

21 Claims, 35 Drawing Sheets

(51) Int. Cl.
*G01R 33/341* (2006.01)
*G01R 33/60* (2006.01)

(58) Field of Classification Search
CPC .... G01R 33/3628; G01R 33/34; G01R 33/48; G01R 33/34092; A61B 5/055; G01N 24/08
See application file for complete search history.

(56) References Cited

U.S. PATENT DOCUMENTS

2018/0356483 A1 12/2018 Zhang et al.
2019/0302207 A1* 10/2019 Purea ..................... G01R 1/067

OTHER PUBLICATIONS

Ali, Hassan, Erik Forsberg, and Hu Jun. "Sub-wavelength imaging with BC-SRRs metamaterial lens for 1.5-T MRI." Applied Magnetic Resonance 47.5 (2016): 539-554. (Year: 2016).*
Rizza, C., et al. "Meta-optics inspired configurations for magnetic resonance imaging applications." 2019 Thirteenth International Congress on Artificial Materials for Novel Wave Phenomena (Metamaterials). IEEE, Sep. 2019. (Year: 2019).*
European Patent Office, International Search Report, issued in PCT/IB2020/056842, mailed Oct. 20, 2020, Rijswijk, Netherlands.
Freire M. J. et al., On the applications of π⌈=-1 metamaterial lenses for magnetic resonance imaging, Journal of Magnetic Resonance, Dec. 29, 2009, pp. 81-90, vol. 203, Issue 1, Academic Press, Orlando, FL, US.
A.V. Zayats et al., Nano-optics of surface plasmon polaritons, Physics Reports, Mar. 2005, pp. 131-314, vol. 408, Issues 3-4, Elsevier.
J.B. Pendry et al., Mimicking Surface Plasmons with Structured Surfaces, Science, Aug. 6, 2004, pp. 847-848, vol. 305, No. 5685, AAAS.
European Patent Office, International Written Opinion, issued in PCT/IB2020/056842, mailed Oct. 20, 2020.
Slobozhanyuk A. P. et al., Enhancement of evanescent waves inside a wire metamaterial endoscope, ICECOM 2013, Oct. 14, 2013, pp. 1-4, IEEE.
Li Chun-Lai et al., Planar Magnetic Metamaterial Slabs for Magnetic Resonance Imaging Applications, Chinese Physics Letters, Jul. 4, 2014, p. 77801, vol. 31, No. 7, Institute of Physics Publishing, Bristol, GB.
Sebastian Rupprecht et al., Improvements of transmit efficiency and receive sensitivity with ultrahigh dielectric constant (uHDC) ceramics at 1.5 T and 3 T, Magnetic Resonance in Medicine, Sep. 25, 2017, pp. 2842-2851, vol. 79, No. 5, US.
Hou J. et al., Dependence of Radiofrequency field enhancement on the geometry of the monolithic high dielectric ceramics at 3 T, Proceedings of the International Society for Magnetic Resonance In Medicine, 27th Annual Meeting & Exhibition, Apr. 26, 2019, No. 1518, Canada.
Ismail Masoud Issa, The Use of Metasurfaces for Magnetic Resonance Imaging Applications, Dissertation, Jul. 31, 2018, URL: http://etheses.whiterose.ac.uk/20823/1/Final%20thesis_version.pdf, retrieved on Sep. 30, 2019.
N. Engheta, R.W. Ziolkowski, Engineering, physics, and applications of Metamaterials, 2006, John Wiley & Sons & IEEE Press.
W.X. Tang et al., Concept, Theory, Design, and Applications of Spoof Surface Plasmon Polaritons at Microwave Frequencies, Advanced Optical Materials, Aug. 28, 2018, vol. 7, Issue 1, 1800421, Wiley.
A. Devilez et al., Mimicking localized surface plasmons with dielectric particles, Physical Review B, Dec. 15, 2015, vol. 92, Issue 24, 1412(R), American Physical Society, US.
C. Rizza et al., Harnessing Surface Plasmons for Magnetic Resonance Imaging Applications, Physical Review Applied, Oct. 10, 2019, p. 044023, vol. 12, Issue 4, American Physical Society, US.

* cited by examiner

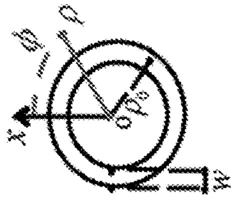
Fig. 22
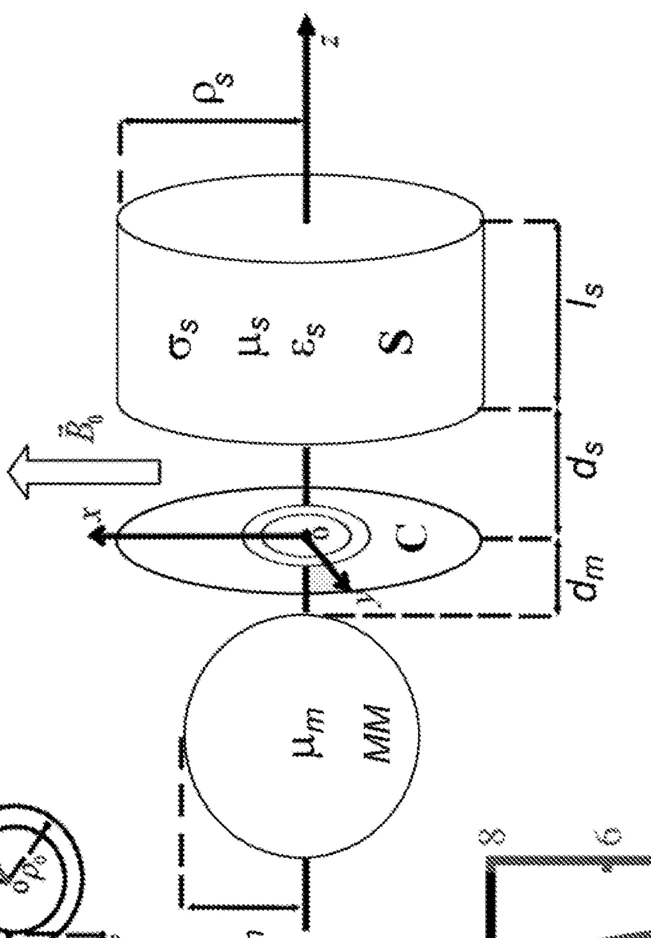
Fig. 23
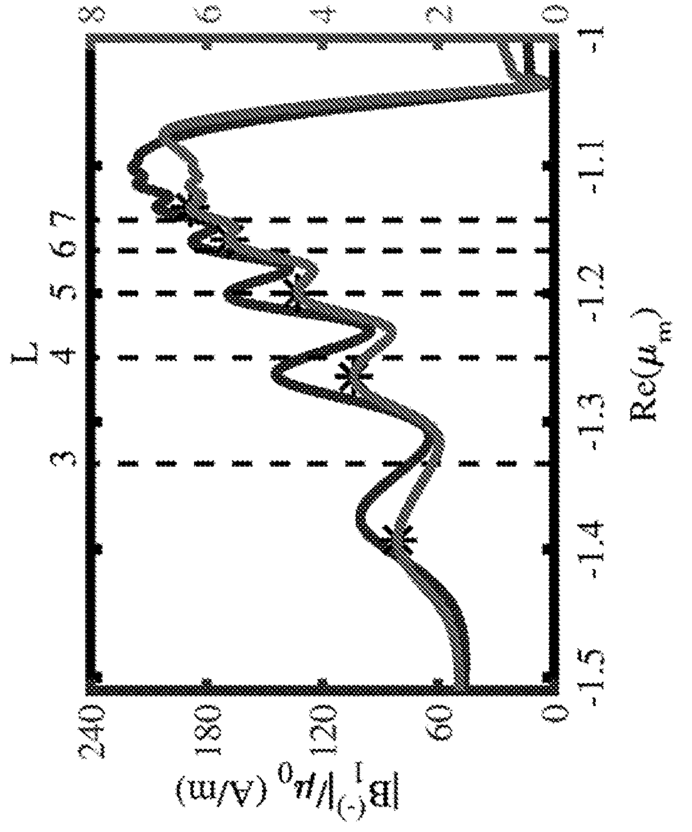

APPARATUS FOR NUCLEAR MAGNETIC RESONANCE UTILIZING METAMATERIALS OR DIELECTRIC MATERIALS

CROSS-REFERENCE TO RELATED APPLICATIONS

This application is a National Phase Application of PCT International Application No. PCT/IB2020/056842, having an International Filing Date of Jul. 21, 2020 which claims the benefit of priority to Italian Patent Application No. 102019000012492, filed Jul. 22, 2019, each of which is hereby incorporated by reference in its entirety.

FIELD OF THE INVENTION

The present invention relates to a magnetic resonance imaging apparatus using metamaterials or dielectric materials.

PRIOR ART

Surface plasmons, i.e. light-Induced collective electronic excitations which lie on a dielectric-metal interface are fundamental ingredients in the field of nanophotonics [1]. These excitations have several significant characteristics, such as a resonant nature with a strong amplification of the electromagnetic field and a spatial confinement thereof. As such, the surface plasmons have been exploited to achieve a huge variety of applications, such as e.g. sub-wavelength waveguides, plasmonic lenses, ultra-sensitive bio-sensors, and chemical sensors. Furthermore, over the past decade, metamaterials have provided an extraordinary platform for plasmonic optics because they display a broad potential for manipulating near-field electromagnetic response as desired.

Metamaterials are artificial composite materials the electromagnetic properties (permeability and permittivity) of which are designed to obtain extraordinary parameters and/or phenomena that are not observed in natural materials, e.g. such as permittivity and/or negative effective permeability [2]. The effective permittivity and permeability of metamaterials derive from their structure rather than from the nature of their components, which are usually conventional conductors and dielectrics. Metamaterials are usually made by repeating resonant elements (elementary cells) which form a periodic structure. An essential property of metamaterials is that both the size of the elementary cells and their periodicity are lower than the length of the electromagnetic waves which propagate through the structure. According to homogenization theories, under such conditions, an effective permittivity and/or permeability of the metamaterial can be defined with values that can produce beneficial and/or unusual effects [2].

As a significant example, the science of metamaterials (MM) has made it possible to design materials with real negative magnetic permeability (magnetic MM) and the observation of the magnetic counterpart of electric surface plasmons (known as surface magnetic plasmons). Indeed, the real part of the negative magnetic permeability is a fundamental ingredient for many fascinating electromagnetic devices, such as the invisibility cloak and far-field super lenses [2].

Furthermore, metamaterials have made it possible to obtain surface resonant electric plasmons which display a real part of the negative electrical permittivity, for frequencies ranging from THz to GHz, e.g. made with appropriate periodic metal structures. The constituent elements (elementary cells) of such metamaterials are equivalent to electrical dipoles the resonant properties of which can be selected through appropriate geometries and values of the relative dielectric constant of the constituent elements [3-4].

In the context of both nuclear and electronic magnetic resonance imaging (NMR/MRI/EPR/EPRI), over the years, the search for increasing the signal-to-noise ratio (SNR) throughout the sample under observation or in a selected region thereof has focused on the possibility of increasing the static magnetic field, obtaining increasingly efficient induction coils, capable of generating an oscillating electromagnetic field which is tuned in a frequency range which typically, but not exclusively, belongs to radio-frequencies (called radio-frequency coils, RF), or use pads with high dielectric constant to optimize the local spatial distribution of the RF magnetic field [5].

More recently, several research teams have exploited metamaterials to manipulate the RF electromagnetic field for magnetic resonance applications, e.g. with micro-structured magnetic materials (Swiss-roll matrices) which make it possible to guide the RF flux from a sample to a remote receiving coil, or a metamaterial with $Re(\mu_m)=-1$ (wherein the real part of the relative magnetic permeability is equal or close to −1) coupled to a substantially planar RF coil [6]. In the latter example, the metamaterial slab behaves like a perfect lens free from loss due to diffraction (Pendry lens), capable of refocusing the RF magnetic field to extend the field of view (FOV) beyond the limits imposed by the standard approach.

In the configuration considered by Freire et al. [6], a metamaterial slab with $Re(\mu_m)=-1$ is located between the RF coil and the sample and can reproduce, in a geometric plane within the sample, the same electromagnetic field configuration present on the surface of the RF coil (in the specific case under examination, this occurs when some conditions occur on the thickness of the metamaterial and its distance from the coil). This type of metamaterial with negative magnetic permeability has been made, in practice, by means of the use of a three-dimensional structure formed by a large number of elementary (cubic) cells which include small (relative to the wavelength) circular resonant coils tuned to the frequency of interest by means of capacitors soldered to the ends of the coils [6].

For magnetic resonance applications. It is advantageous to exploit the high local electromagnetic fields associated with surface plasmons (magnetic and/or electrical) while keeping the RF coil as close to the sample as possible. Other needs with respect to the prior art are

- using the surface plasmonic resonances of the metamaterial to optimize the amplitude and/or spatial distribution of the excitation RF field and/or the detection sensitivity within the sample;
- providing specific physical dimensions and/or spatial arrangements and/or electromagnetic properties of the metamaterial to optimize the amplitude and spatial distribution of the excitation and/or detection RF field and/or the signal-to-noise ratio (SNR) within the sample;
- using the metamaterial for magnetic resonance imaging applications in multinuclear mode (at least two nuclei of interest in the sample);
- using the metamaterial for quadrupole magnetic resonance applications.

Furthermore, several research teams have studied the inclusion of high dielectric index dielectric materials (uHDC) in a standard MRI scanner to manipulate the local RF field distribution [5]. Such materials with high relative dielectric constant (values up to 4000) support intense internal displacement currents and can modify the distribution of the RF electromagnetic field outside the dielectric itself [5]. Such effect was taken into account for shimming and/or RF field focusing with uHDC dielectric elements in MRI scanners, demonstrating its effectiveness at different static magnetic field values (3, 4, 7, 9.4 T). In some cases, the same physical principle is achieved with dielectric gets with high permittivity index to achieve a good degree of adaptation of the electromagnetic impedance between the sample and the RF source.

The dielectric resonances intrinsic to high permittivity liquid materials (e.g. deionized water) have made it possible to select a dielectric resonance mod, appropriately tuned to the Larmor frequency, and to use the liquid itself as a sensor in transmission/reception mode to acquire magnetic resonance images of a sample immersed in the liquid dielectric. Although this is very interesting from a scientific point of view, it has limited practical applications and dielectric losses are quite high.

The use of cylinder-shaped solid dielectric resonators in which a small through-hole along the central axis is cut made it possible to carry out resonance measurements with small samples inserted in such hole by exciting a specific dielectric resonance mode (e.g. $TE_{01}$). Such configuration applies only to selected geometries and in the case of an increase in the diameter of the central hole the dielectric resonance loses effectiveness by reducing the RF field strength on the sample.

The use of an annular dielectric resonator has recently been demonstrated to perform magnetic resonance measurements. One of the problems with the use of these uHDC dielectric materials is the high internal losses caused by displacement currents.

The prior art shows that the use of dielectric materials with high dielectric constant for MRI applications has the following limitations:

- In most magnetic resonance imaging applications, dielectric pads are used as elements for the adaptation of the electromagnetic impedance between RF coil and sample, i.e., they are almost never used under dielectric resonance conditions;
- In the few cases in which dielectrics are used in resonance conditions, either they are composed of a liquid and the sample can be immersed in it with obvious limitations, or they are shaped with a cylindrical internal cavity in which the sample is inserted, with considerable dimensional limitations of the sample itself; and
- Currently, dielectric resonators are tuned to the Larmor frequency of the magnetic resonance instrument by the choice of geometric and/or dielectric parameters, but no methods are reported for tuning with dynamic and/or adaptive mode.

Purpose and Object of the Invention

It is the purpose of the present invention to provide a magnetic resonance imaging apparatus that exploits metamaterials and dielectric materials and solves the problems of prior art either entirely or in part.

An object of the present invention is an apparatus according to the accompanying claims.

BRIEF DESCRIPTION OF THE FIGURES

The invention will now be described by way of example, with particular reference to the drawings of the accompanying figures, in which.

the excitation (co-rotating) RF magnetic field per unit of RF oil current $$|B_1^{(+)}|/\mu_0 \text{ (in } A/m),$$

the RF electric field per unit of RF coil current [E], in absolute (V/m) or normalized units $|E^{(n)}|=|E|/[E_0]$, where $[E_0]$ is the maximum value of the electric field in the sample calculated in the configuration without the MM, the specific absorption rate (SAR) per current unit in the RF coil in (W/kg) and the normalized ($SNR^{(n)}=SNR^{(m)}/SNR^{(V)}$) signal-to-noise ratio (SNR), where $SNR^{(m)}$, $SNR^{(V)}$ are calculated in presence and absence of the metamaterial, respectively.

Figure 2:
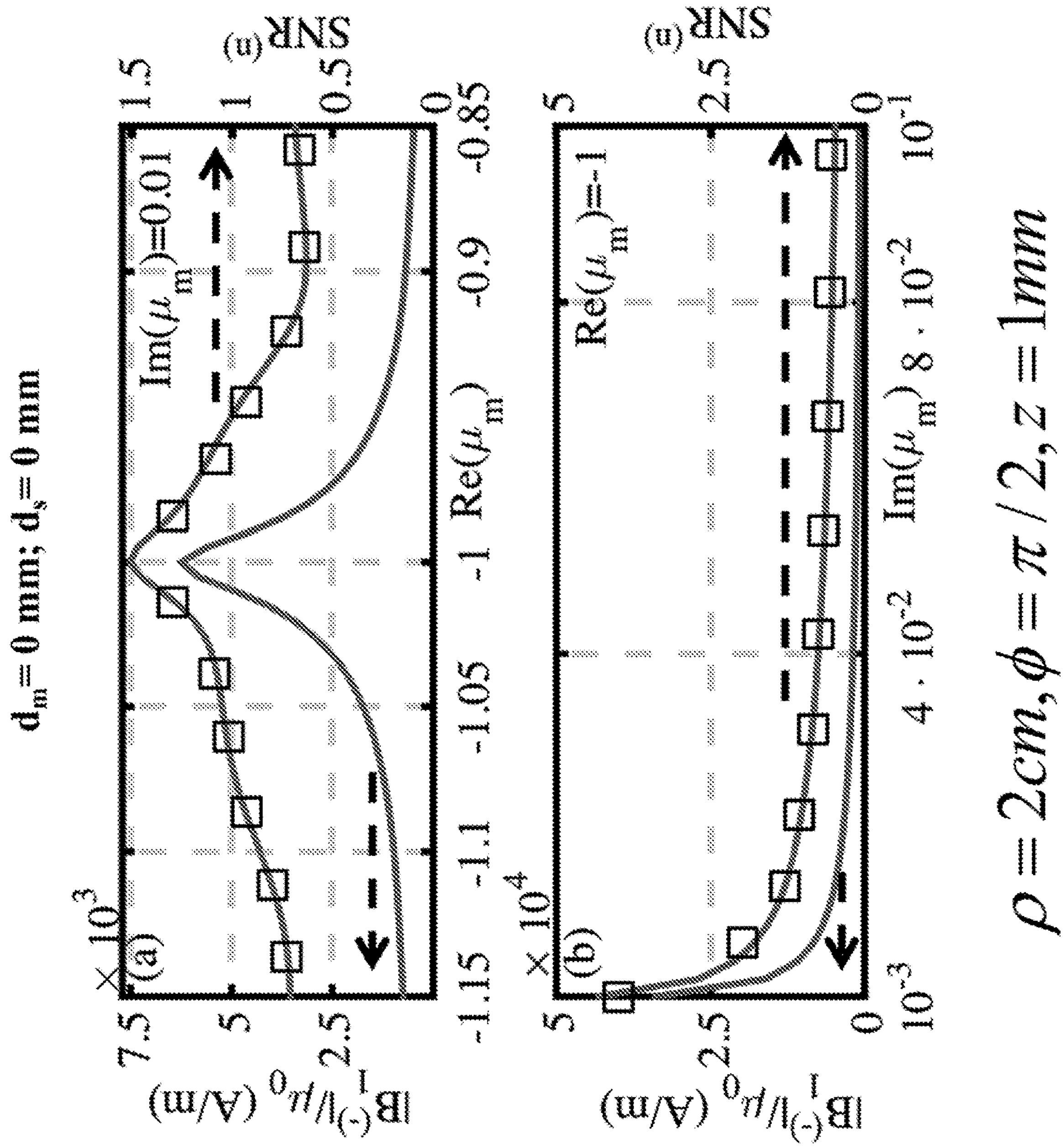

FIG. 2 shows the graph of $$|B_1^{(-)}|/\mu_0 \text{ (curves)}$$

and $SNR^{(n)}$ (curves) and $SNR^{(n)}$ (curves with square symbols) as a function of: (a) Re($\mu_m$) (assuming Im($\mu_m$)=0.01); (b) Im($\mu_m$)(assuming Re($\mu_m$)=−1). In both cases, $$|B_1^{(-)}|/\mu_0$$

and $SNR^{(n)}$ are calculated at $$\rho = 2 \text{ cm}; \phi = \frac{\pi}{2}; z = 1 \text{ mm};$$

having assumed $d_m=d_s$=0 mm.

Figure 3:
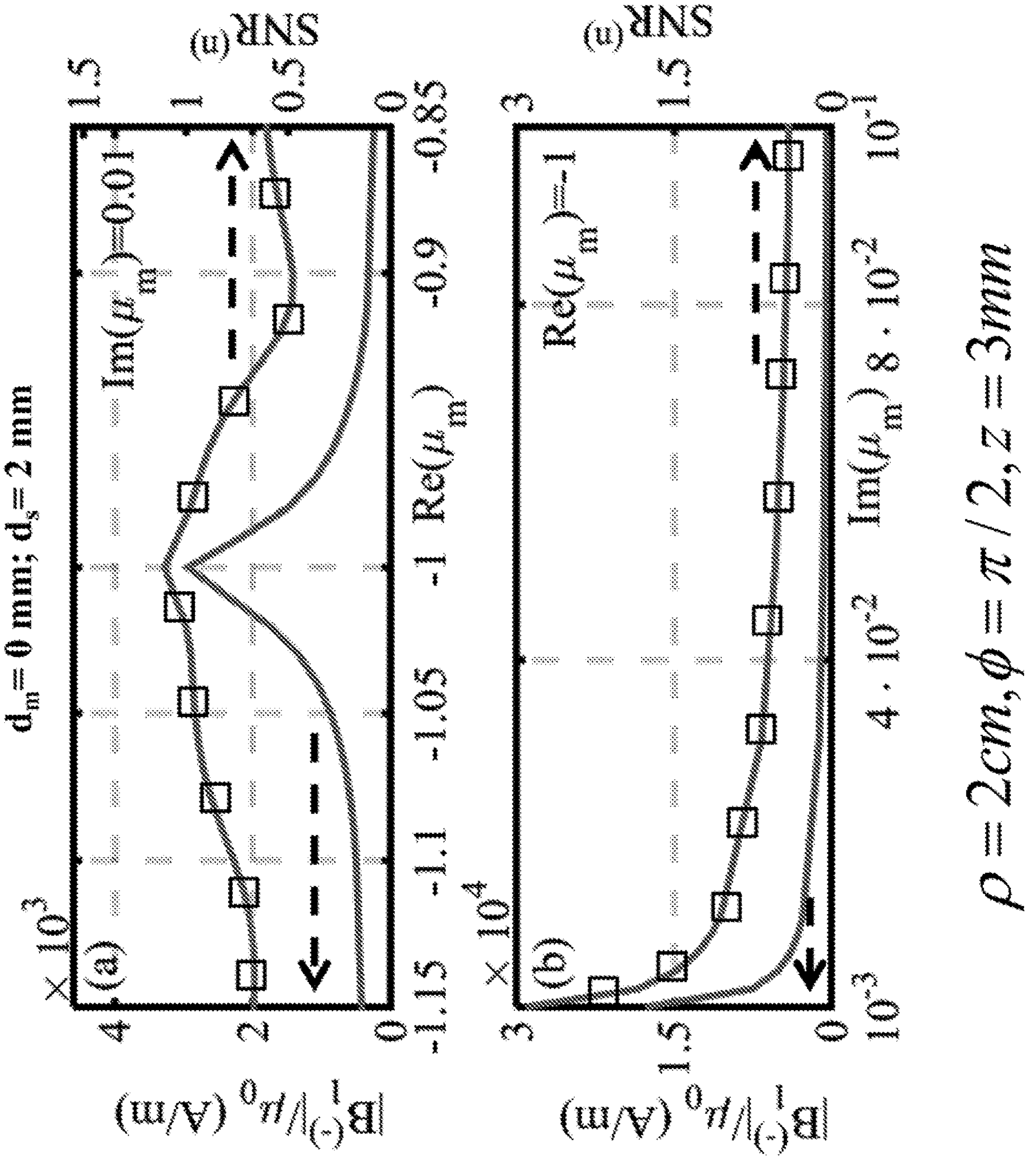

FIG. 3 shows a graph as in FIG. 2 where $$|B_1^{(-)}|/\mu_0$$

and $SNR^{(n)}$ are calculated in the point:

$$\rho = 2\text{ cm};\ \phi = \frac{\pi}{2};\ z = 3\text{ mm; for } d_m = 0\text{ mm};\ d_s = 2\text{ mm}.$$

Figure 4:
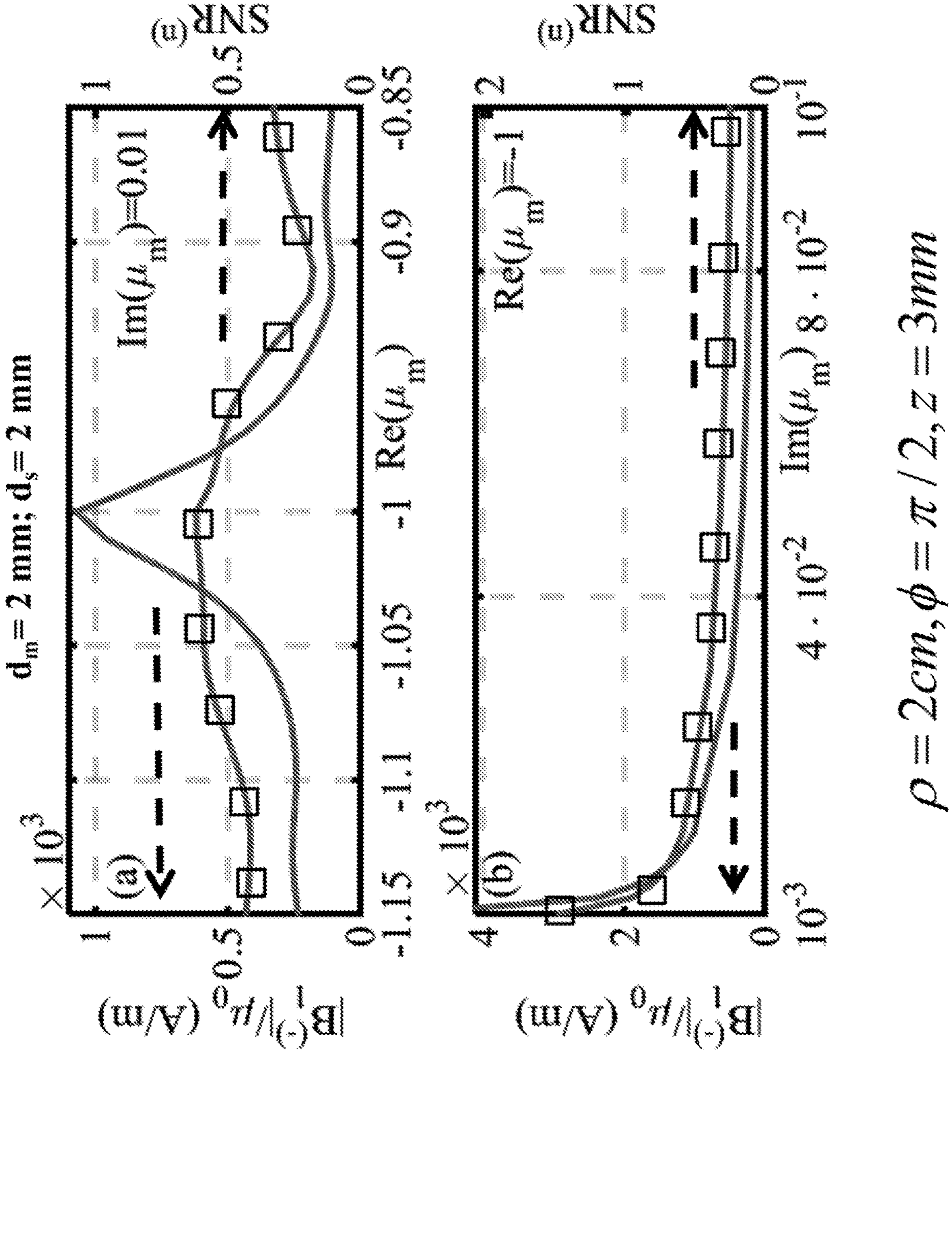

FIG. 4 shows a graph as in FIG. 2 where $$|B_1^{(-)}|/\mu_0$$

and SNR$^{(n)}$ are calculated in the point:

$$\rho = 2\text{ cm};\ \phi = \frac{\pi}{2};\ z = 3\text{ mm};$$

for $d_m$=2 mm; $d_s$=2 mm.

Figure 5:
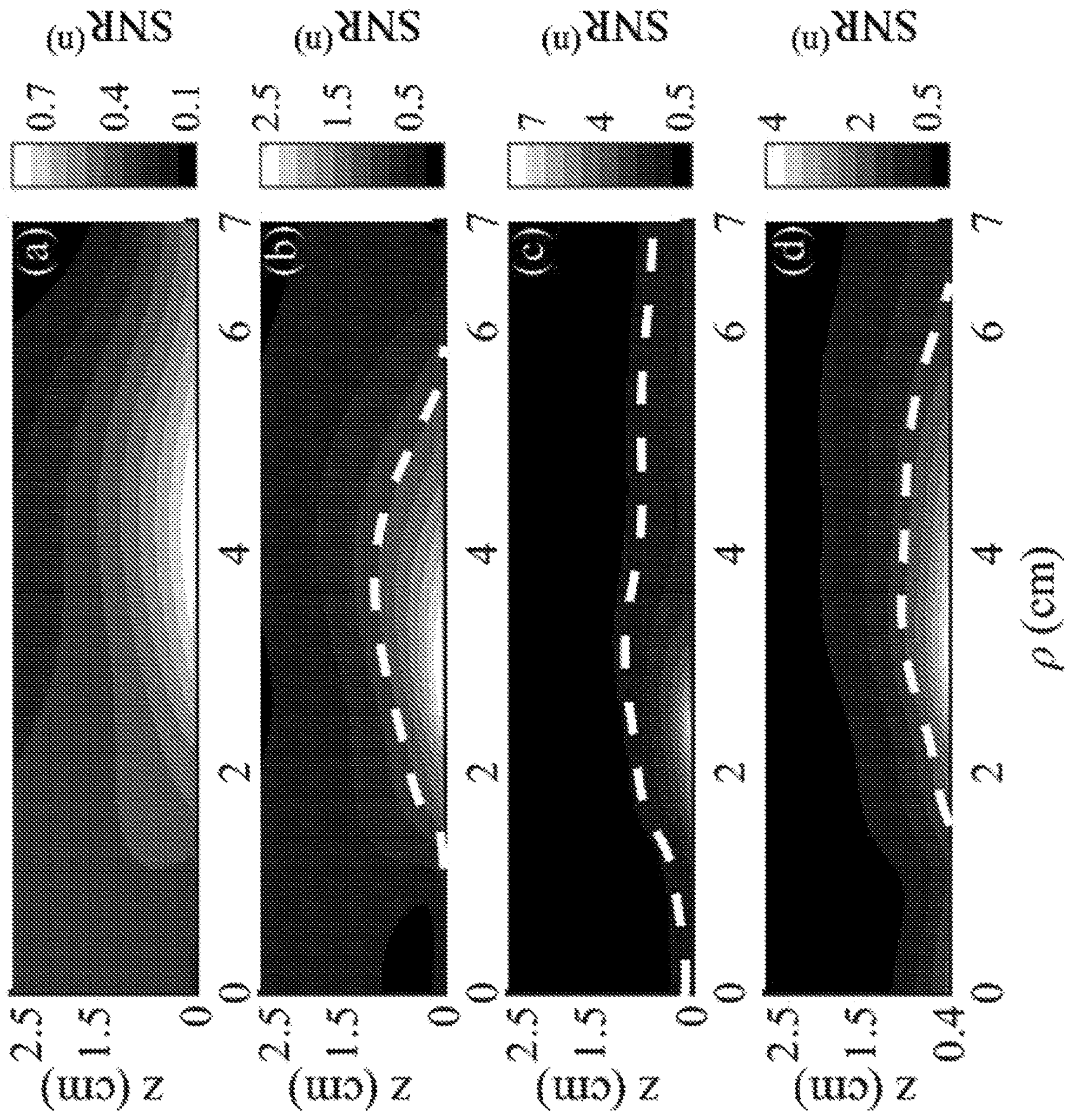

FIG. 5 shows a two-dimensional map in the plane (ρ, z) of SNR$^{(n)}$ in the presence of the metamaterial slab assuming $$\text{Re}(\mu_m) = -1,\ d_m = d_s = 0\text{ mm},\ \phi = \frac{\pi}{2},$$
$$l_m = 5.7\text{ cm},\ l_s = 20\text{ cm}$$
$$\text{with: } (a)\ \text{Im}(\mu_m) = 0.1;\ (b)\ \text{Im}(\mu_m) = 0.01;\ (c)\ \text{Im}(\mu_m) = 0.001;$$

in panel (d) same parameters as (c) but with $d_s$=4 mm; the white dotted curves correspond to level SNR$^{(n)}$=1.

Figure 6:
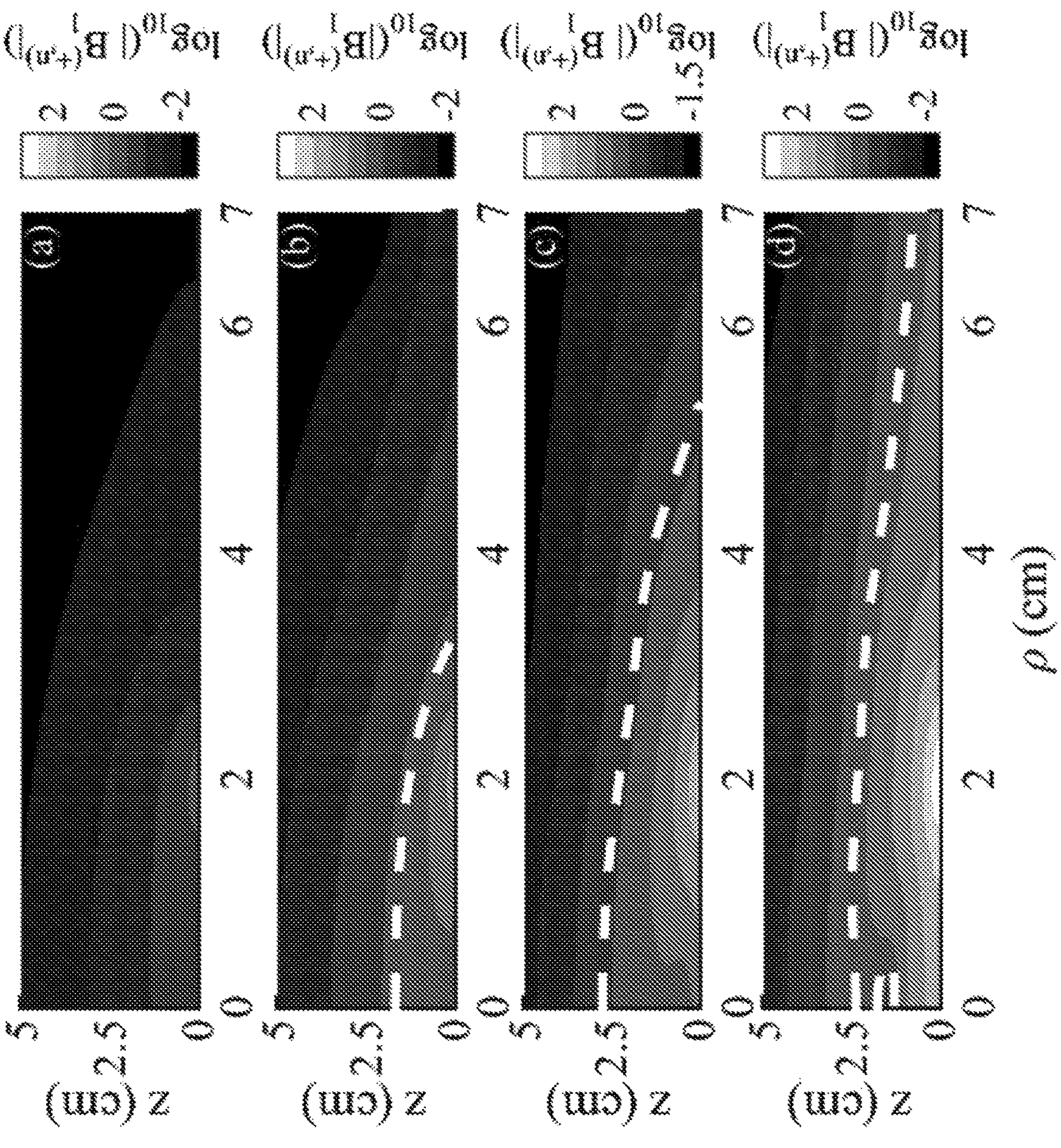

FIG. 6 shows a two-dimensional map in the plane (ρ, z) of $$\log_{10}|B_1^{(+,n)}|,\text{ with } |B_1^{(+,n)}| = |B_1^{(+,MM)}|/|B_1^{(+,V)}|,$$

where $$|B_1^{(+MM)}|$$

is the excitation RF magnetic field calculated in presence of the metamaterial, $$|B_1^{(+V)}|$$

is the maximum of the absolute value of the same quantity, within the sample, in the configuration without the metamaterial; in the figure, it is assumed $$d_m = d_s = 0\text{ mm},\ \phi = \frac{\pi}{2},\ l_m = 5.7\text{ cm},\ l_s = 20\text{ cm}$$

and with: (a) $\mu_m$=1, (i.e. vacuum instead of metamaterial); (b) $\mu_m$=−1+i0.1; (c) $\mu_m$=1+i0.01; (d) $\mu_m$=−1+i 0.001. The white dotted curves correspond to level $$\log_{10}|B_1^{(+n)}| = 0,$$

Figure 7:
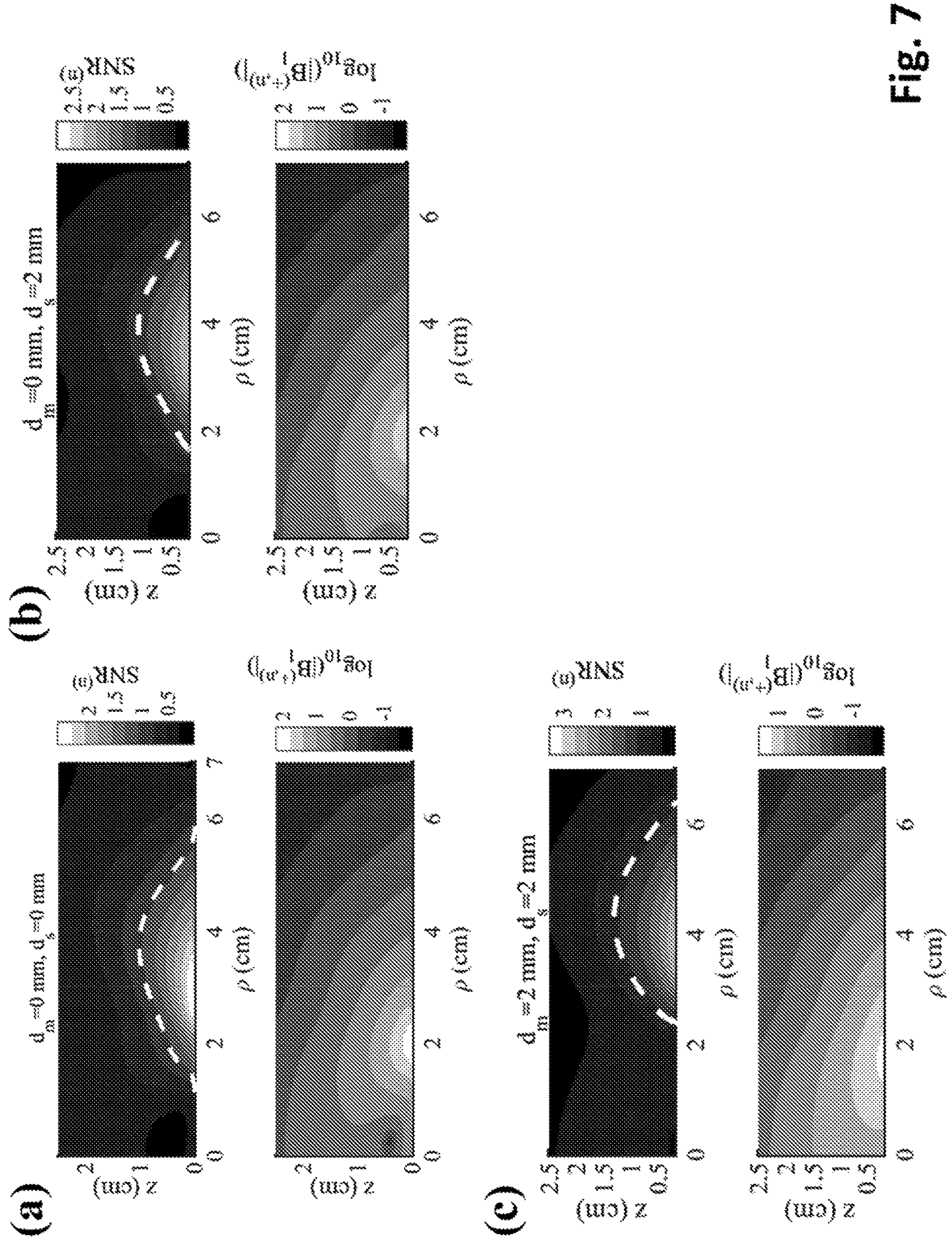

FIG. 7 shows a two-dimensional map in the plane (ρ, z) of SNR$^{(n)}$ and $$\log_{10}|B_1^{(+n)}|$$

assuming $$\phi = \frac{\pi}{2},\ \mu_m = -1 + i0.01,\ l_m = 5.7\text{ cm},\ l_s = 20\text{ cm}$$

and with: (a) $d_m$=$d_s$=0 mm; (b) $d_m$=0 mm, $d_s$=2 mm; (c) $d_m$=$d_s$=2 mm. The white dotted curves correspond to level SNR$^{(n)}$=1.

Figure 8:
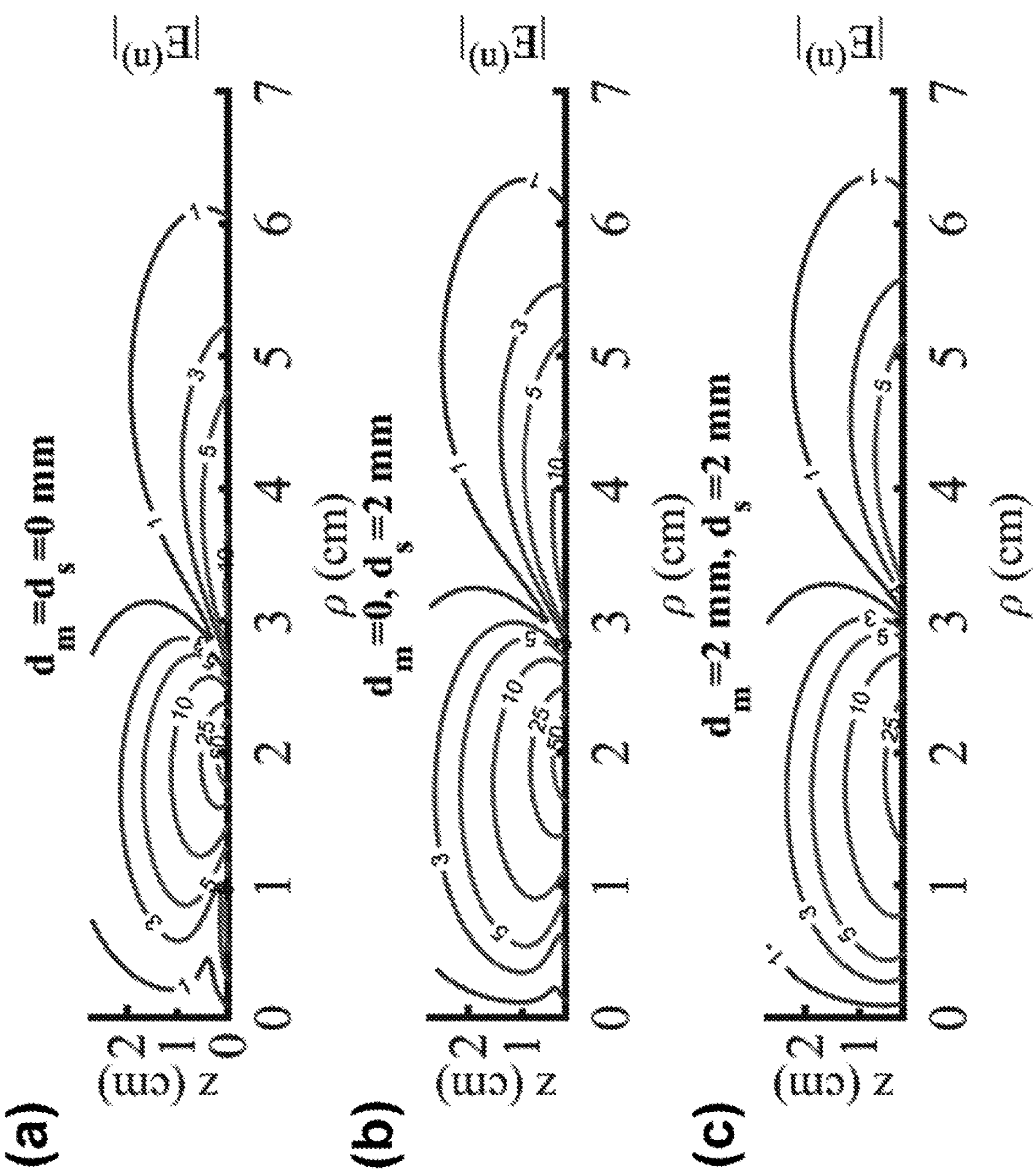

FIG. 8 shows the level curves of the normalized electric field $|E^{(n)}|=|E|/|E_0|$ in the plane (ρ, z), where $|E_0|$ is the maximum value of the electric field in the sample calculated in the configuration without metamaterial, $l_m$=5.7 cm, $l_s$=20 cm and with: (a) $d_m$=$d_s$=0 mm; (b) $d_m$=0 mm, $d_s$=2 mm; (c) $d_m$=$d_s$=2 mm.

Figure 9:
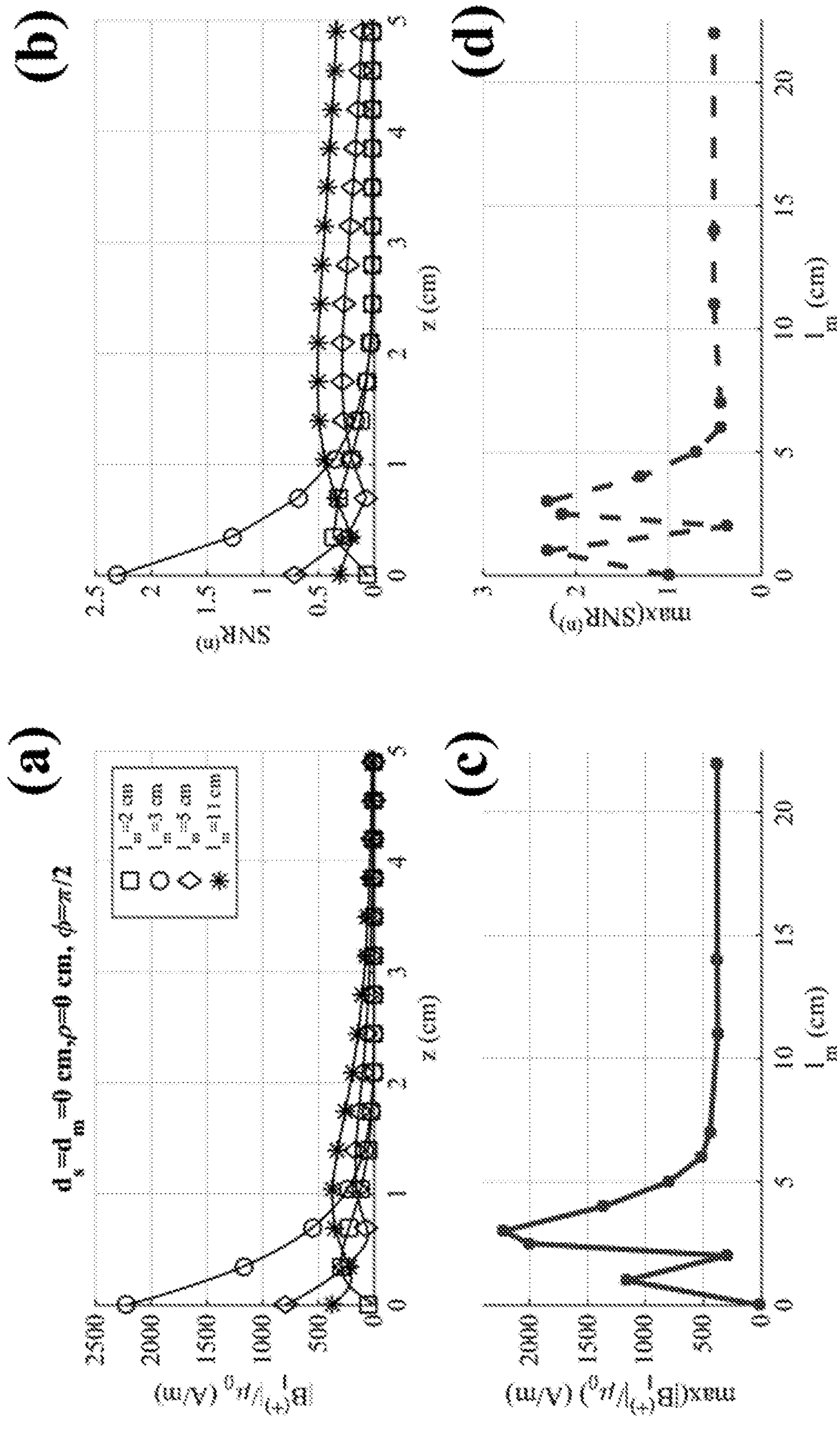

FIG. 9 shows the dependency along axis z of:

$$(a)\ |B_1^{(+)}|/\mu_0$$

and (b) SNR$^{(n)}$, both calculated for $$\mu_m = -1 + i0,1,\ \phi = \frac{\pi}{2},$$
$$\rho = 0\text{ cm},$$
$$d_m = d_s = 0\text{ mm}$$

for metamaterial thickness values $l_m$ between 0 cm and 11 cm and $l_s$=20 cm; in (c) the maximum value of $$|B_1^{((+)}(z)|/\mu_0$$

and in (d) the maximum value of SNR$^{(n)}$(z) are shown, both calculated in the corresponding coordinate z inferred from panels (a) and (b), calculated as a function of $l_m$ (between 0 cm and 25 cm) for $$\phi = \frac{\pi}{2},\ \rho = 0\text{ cm}.$$

Figure 10:
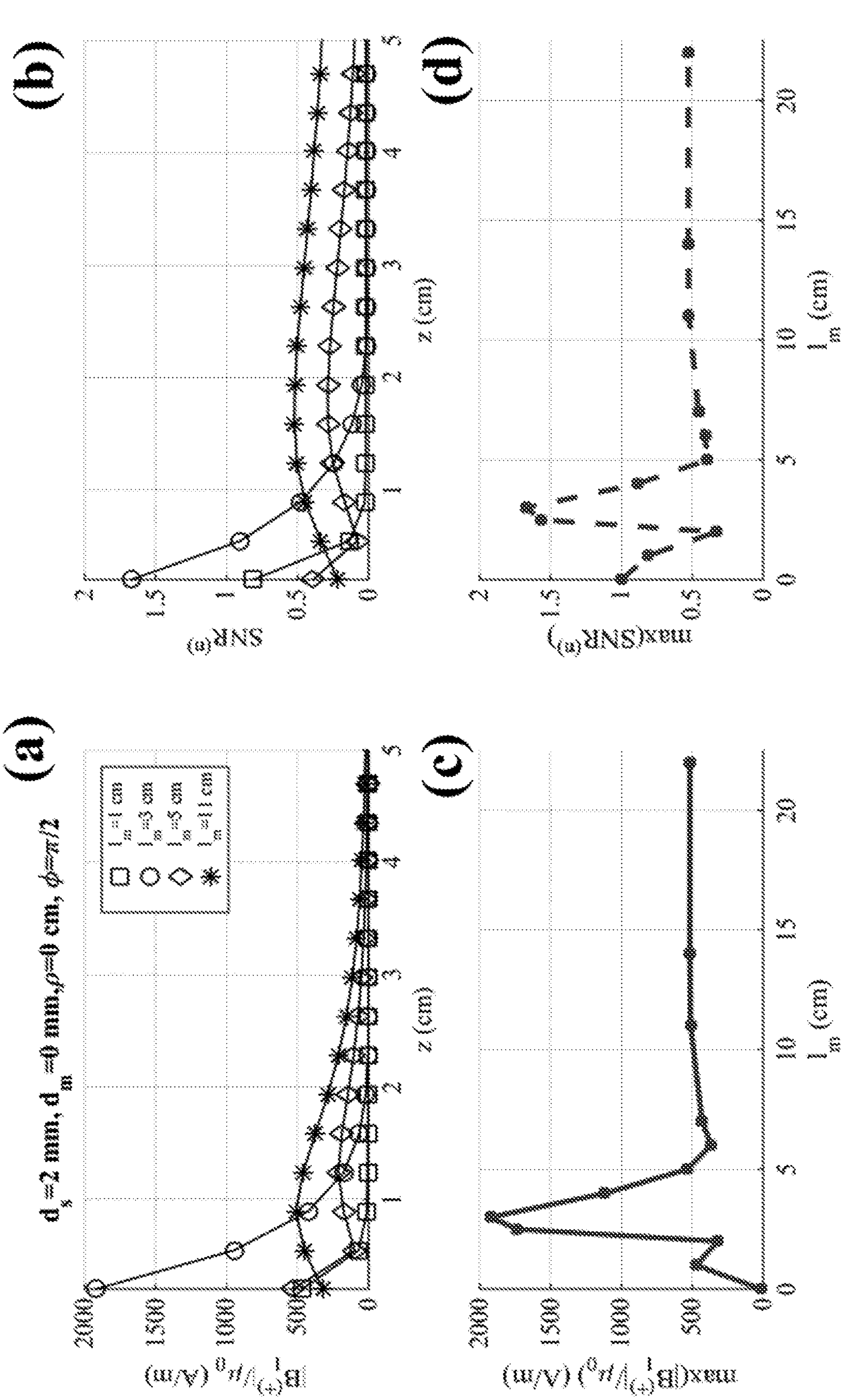

FIG. 10 shows a graph as in FIG. 9 where $d_m$=0 mm, $d_s$=2 mm.

Figure 11:
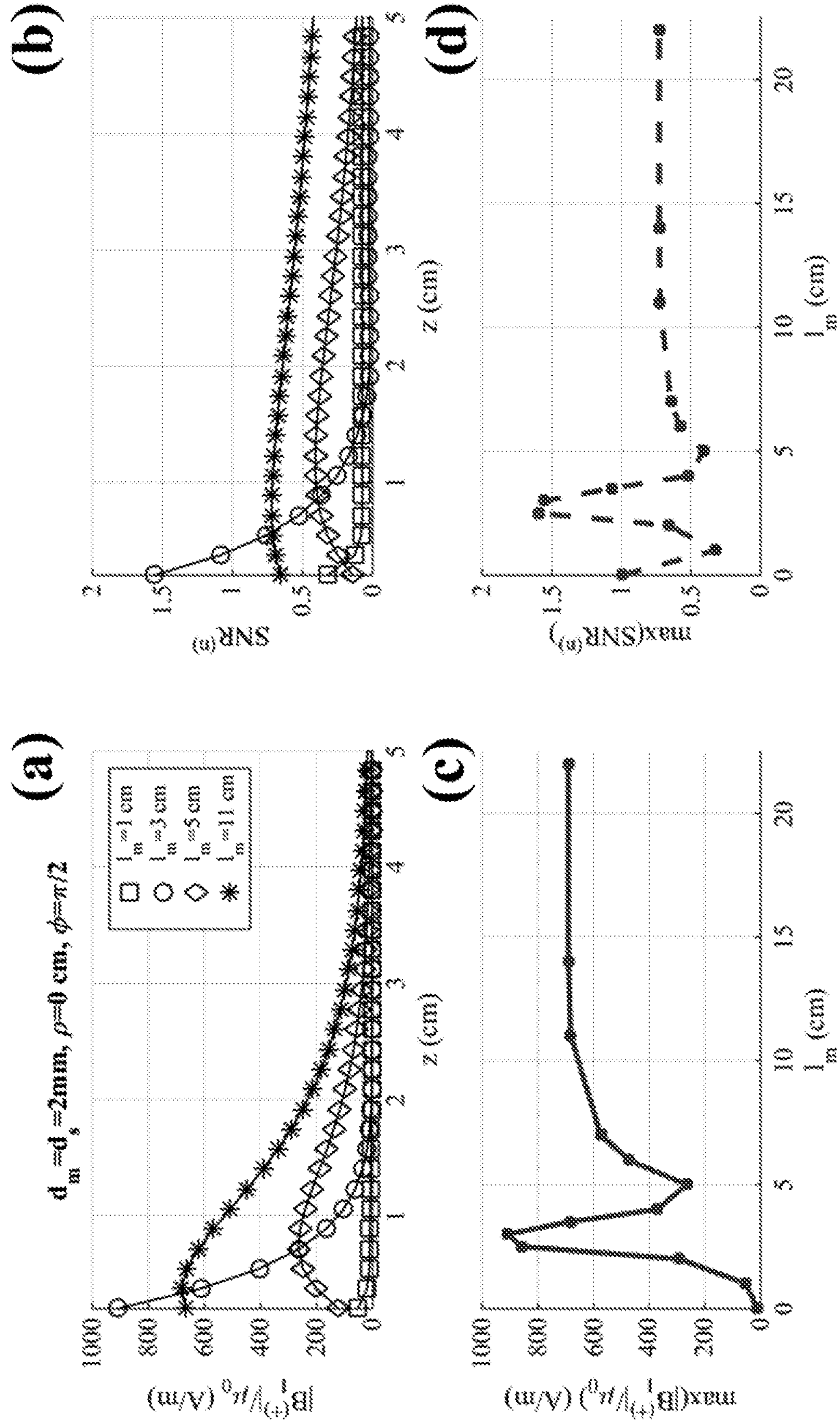

FIG. 11 shows a graph as in FIG. 9 where $d_m$=2 mm, $d_s$=2 mm.

Figure 12:
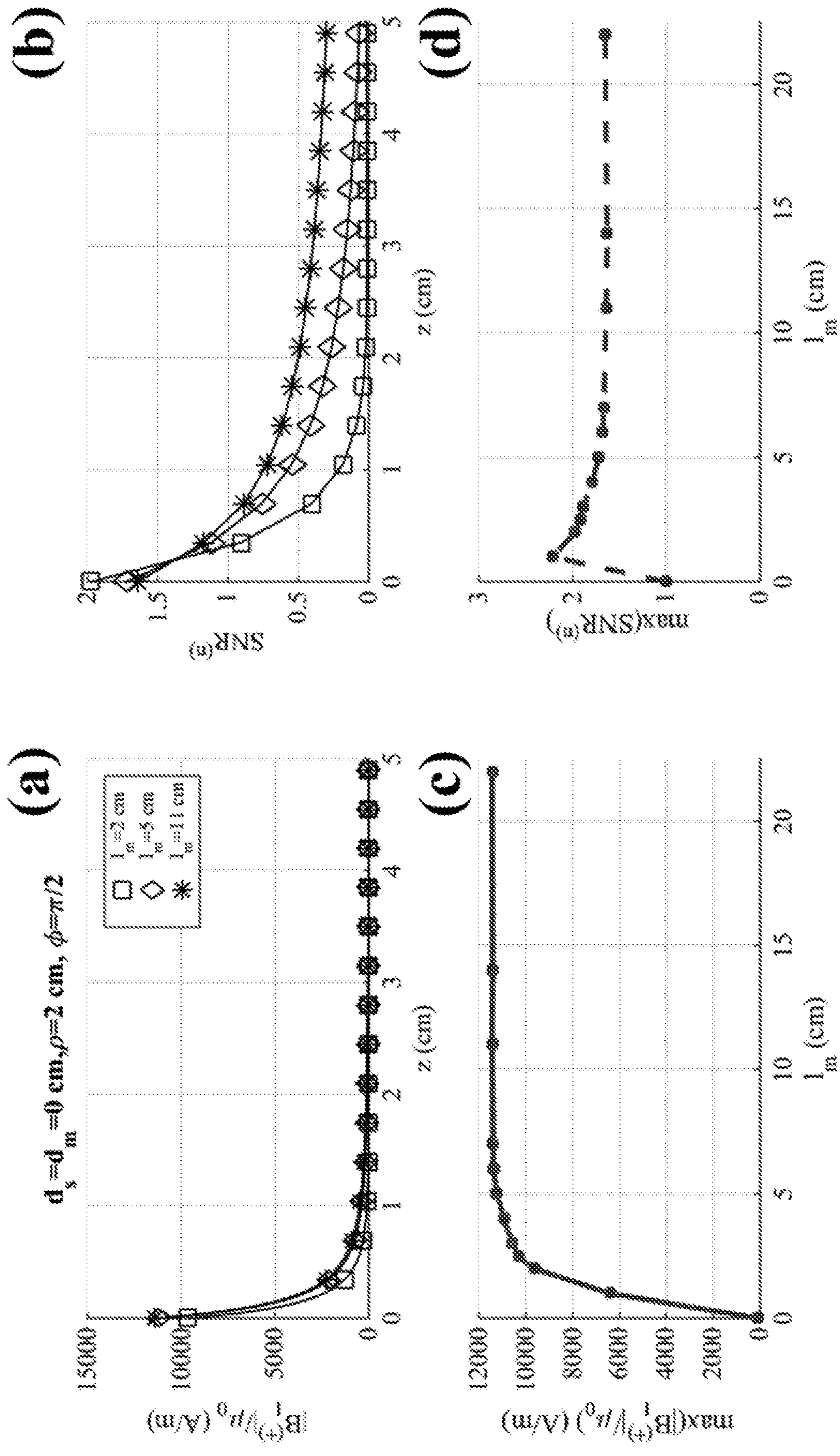

FIG. 12 shows a graph as in FIG. 9 where ρ=2 cm.

Figure 13:
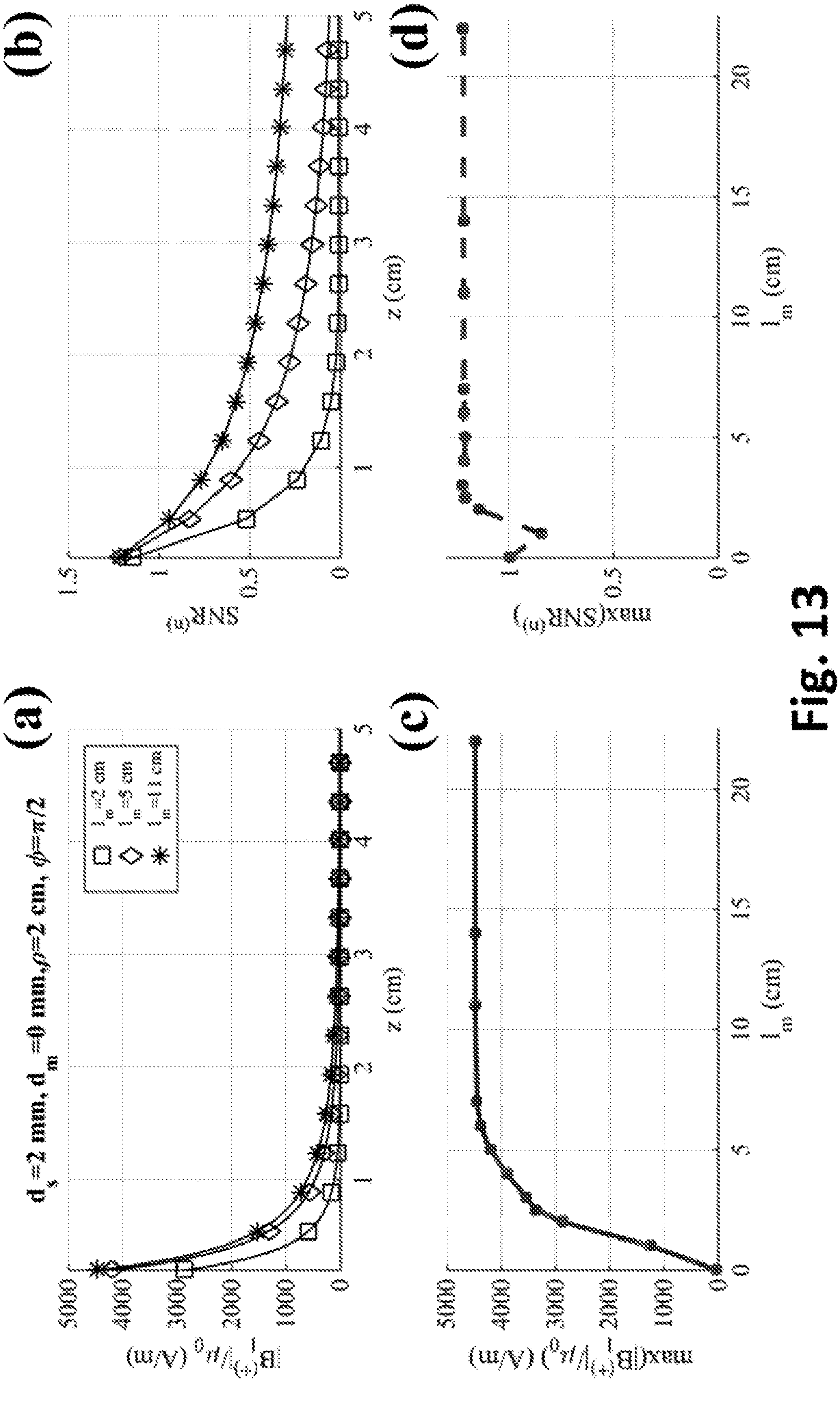

FIG. 13 shows a graph as in FIG. 9 where ρ2 cm, $d_m$=0 mm, $d_s$=2 mm.

Figure 14:
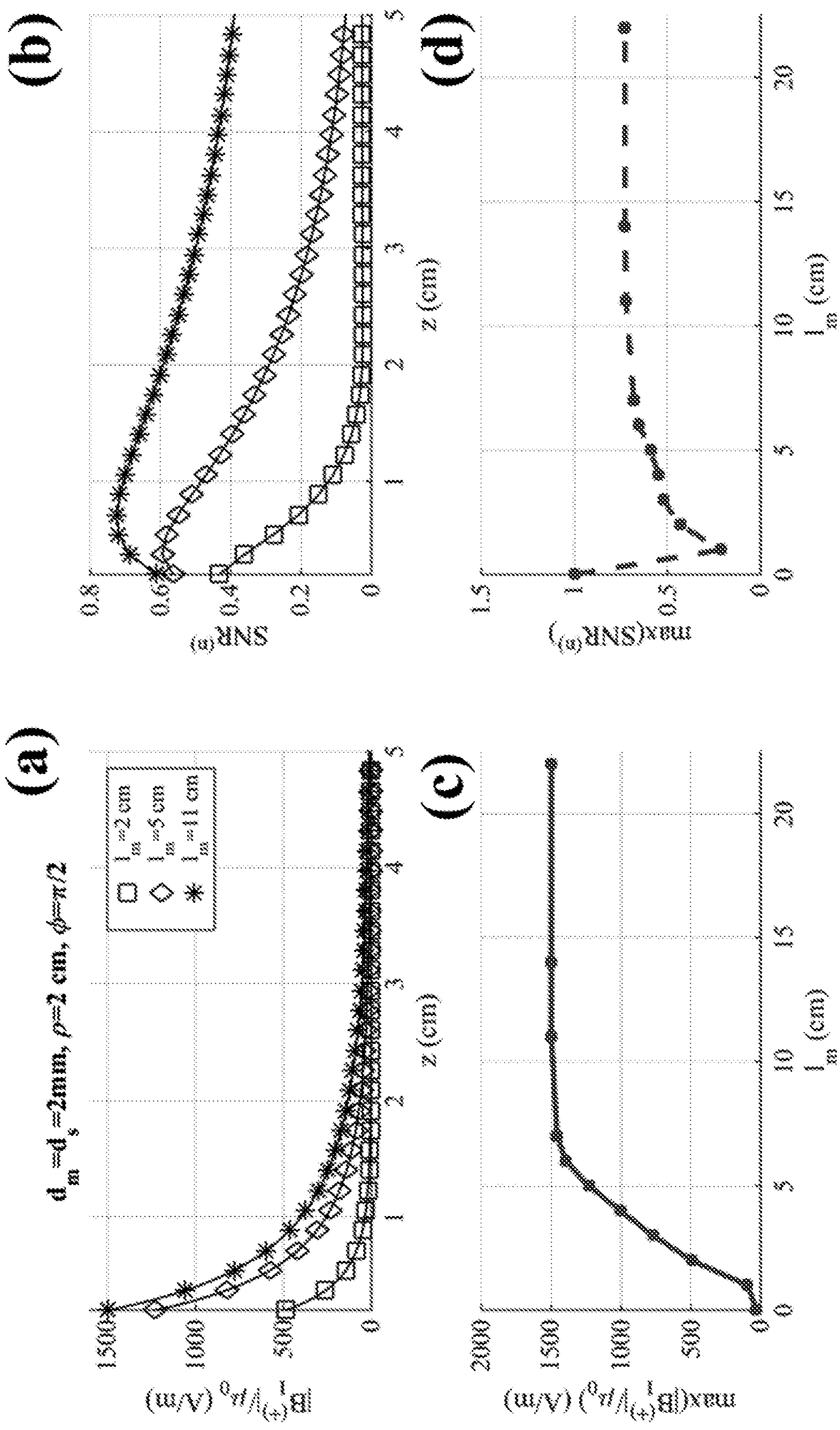

FIG. 14 shows a graph as in FIG. 9 where ρ=2 cm, $d_m$=$d_s$=2 mm.

Figure 15:
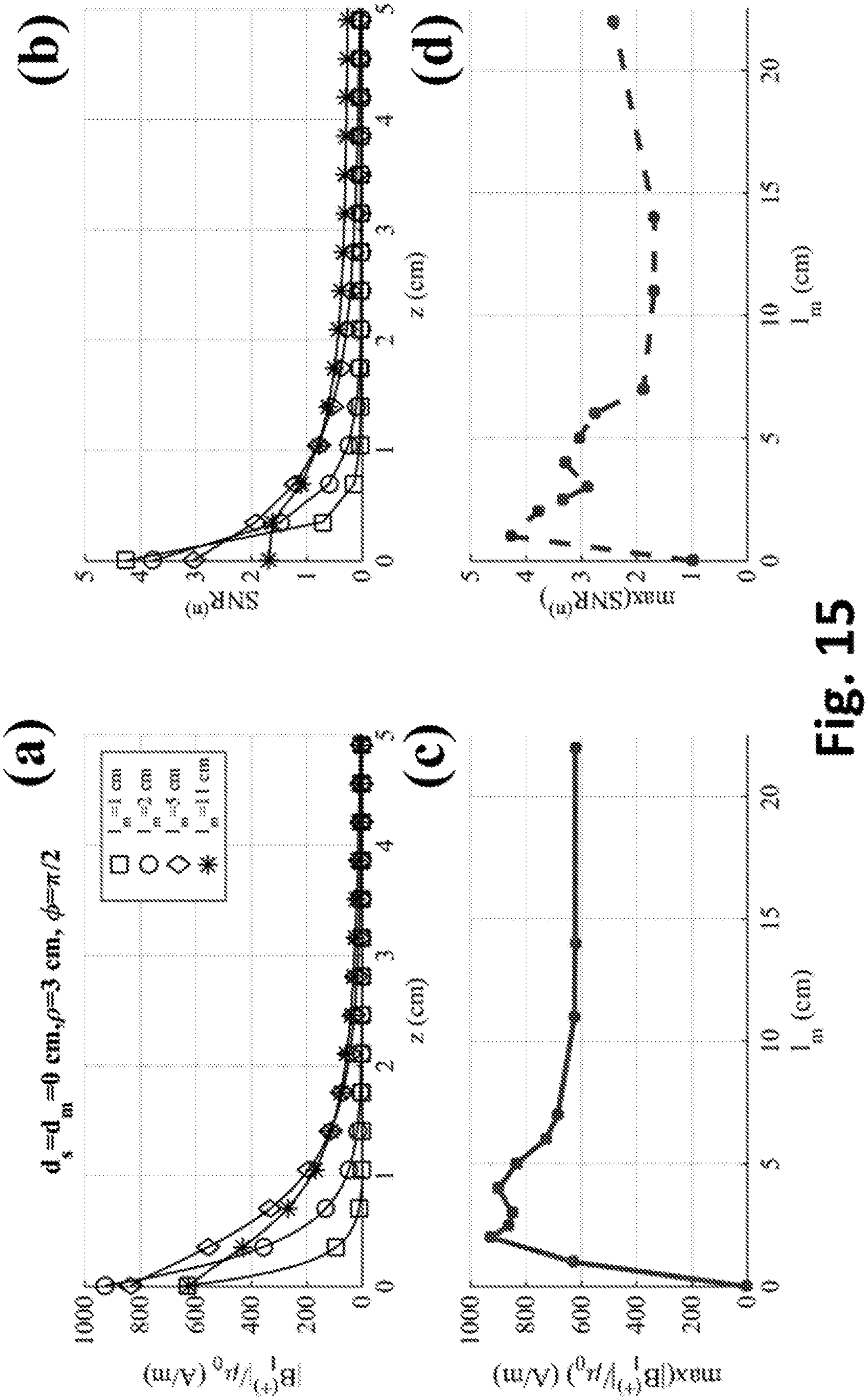

FIG. 15 shows a graph as in FIG. 9 where ρ=3 cm.

Figure 16:
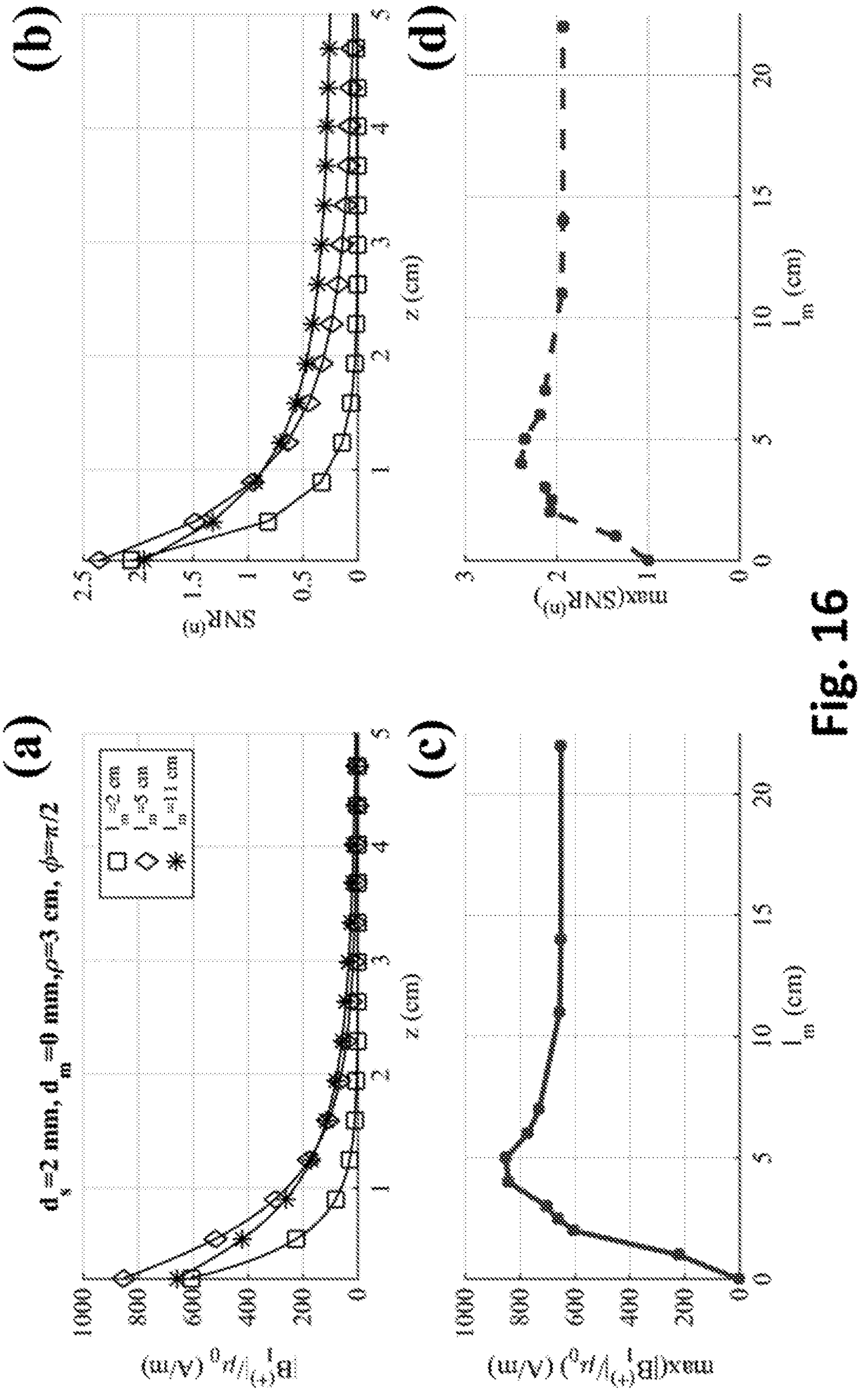

FIG. 16 shows a graph as in FIG. 9 where ρ=3 cm, $d_m$=0 mm, $d_s$=2 mm.

Figure 17:
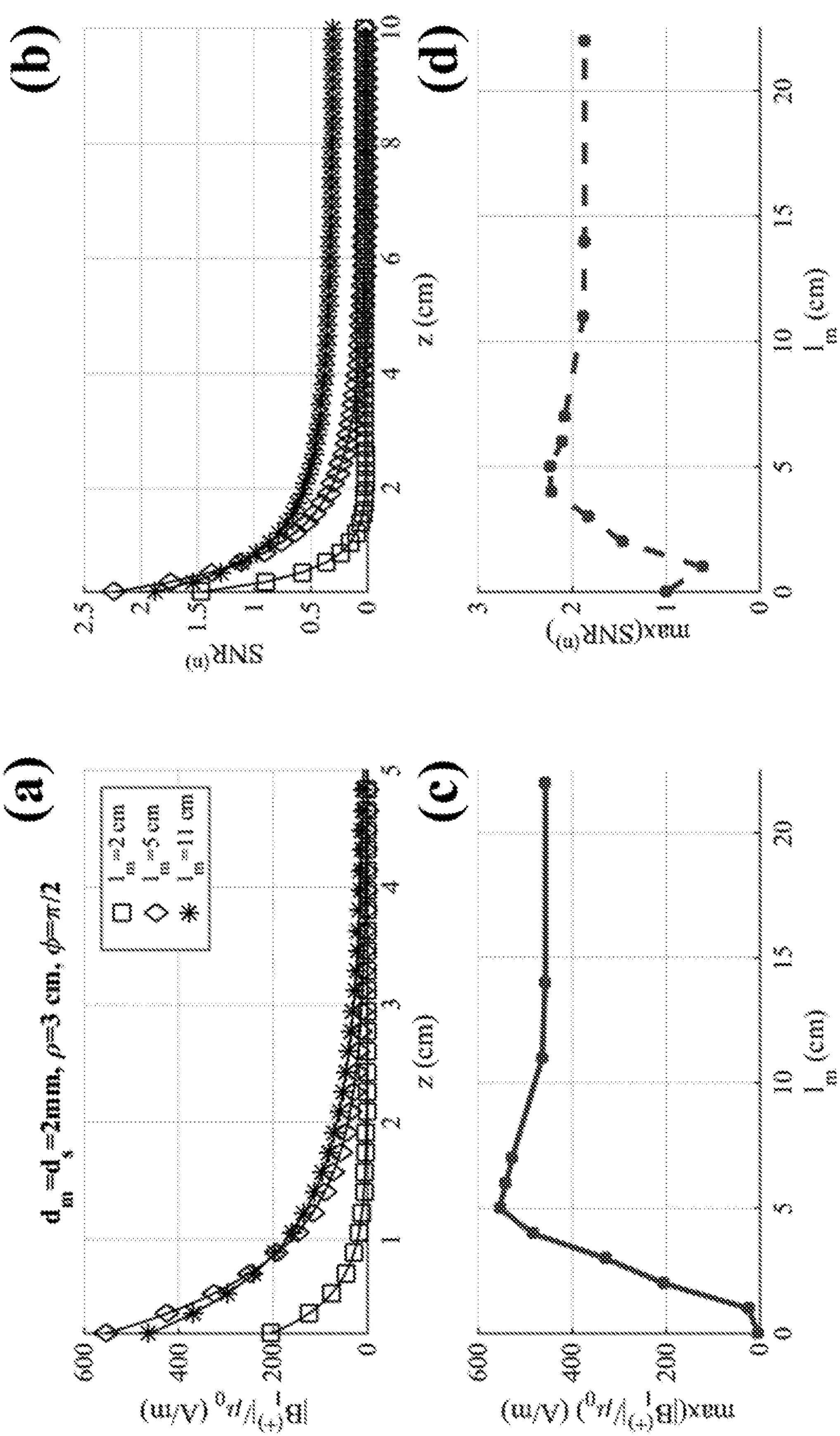

FIG. 17 shows a graph as in FIG. 9 where ρ=3 cm, $d_s$=$d_m$=2 mm.

Figure 1:
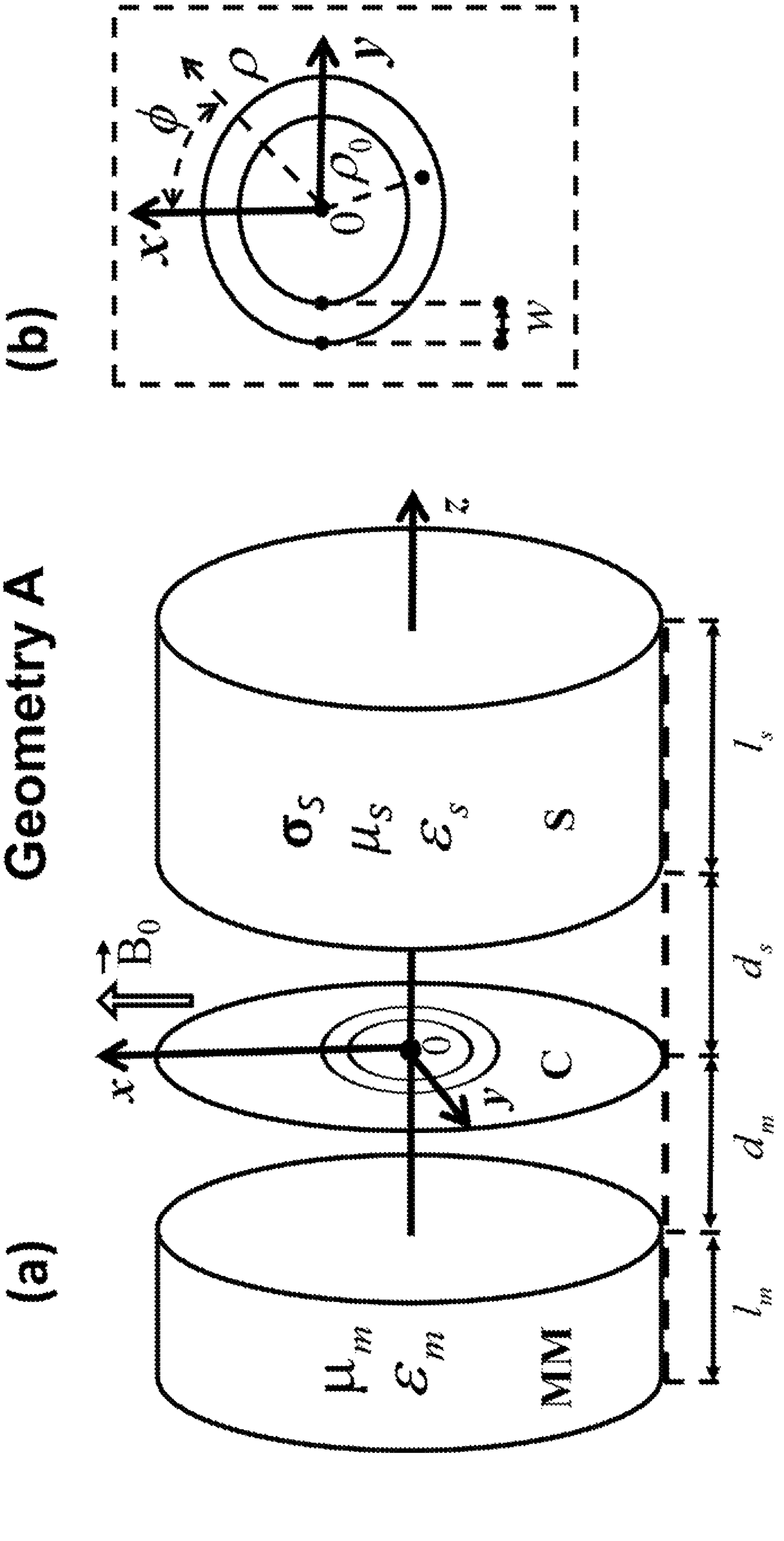
FIG. 1 shows in (a) the geometry A of a configuration according to the invention which comprises: a conventional RF coil (of circular shape, reference "C") positioned in the center of the reference system (x, y, z) and whose principal axis (z) is perpendicular to the applied static magnetic field $\vec{B}_0$; the sample (reference "S", thickness $l_s$, permittivity $\epsilon_s$, conductivity $\sigma_s$, permeability $\mu_s$, assumed to be of transverse dimension greater than the dimension of the coil along axes x and y, positioned at distance (or "quantity") $d_s$ from the RF coil); a metamaterial slab (referenced by "MM", thickness $l_m$, permittivity $\epsilon_m$, permeability $\mu_m$=[Re ($\mu_m$)+Im($\mu_m$)]), supposedly of dimensions larger than the RF coil along x- and y-axes, positioned at distance (or "quantity") $d_m$ from the RF coil. (b) Construction detail of the conventional RF coil with radius $\rho_0$ and radial width w; the spatial coordinates ($\rho$, $\phi$, z) are used to identify points of interest for calculating (or measuring) the detection (counter-rotating) RF magnetic field per current unit of the RF coil $$|B_1^{(-)}|/\mu_0 \text{ (in } A/m),$$
Figure 18:
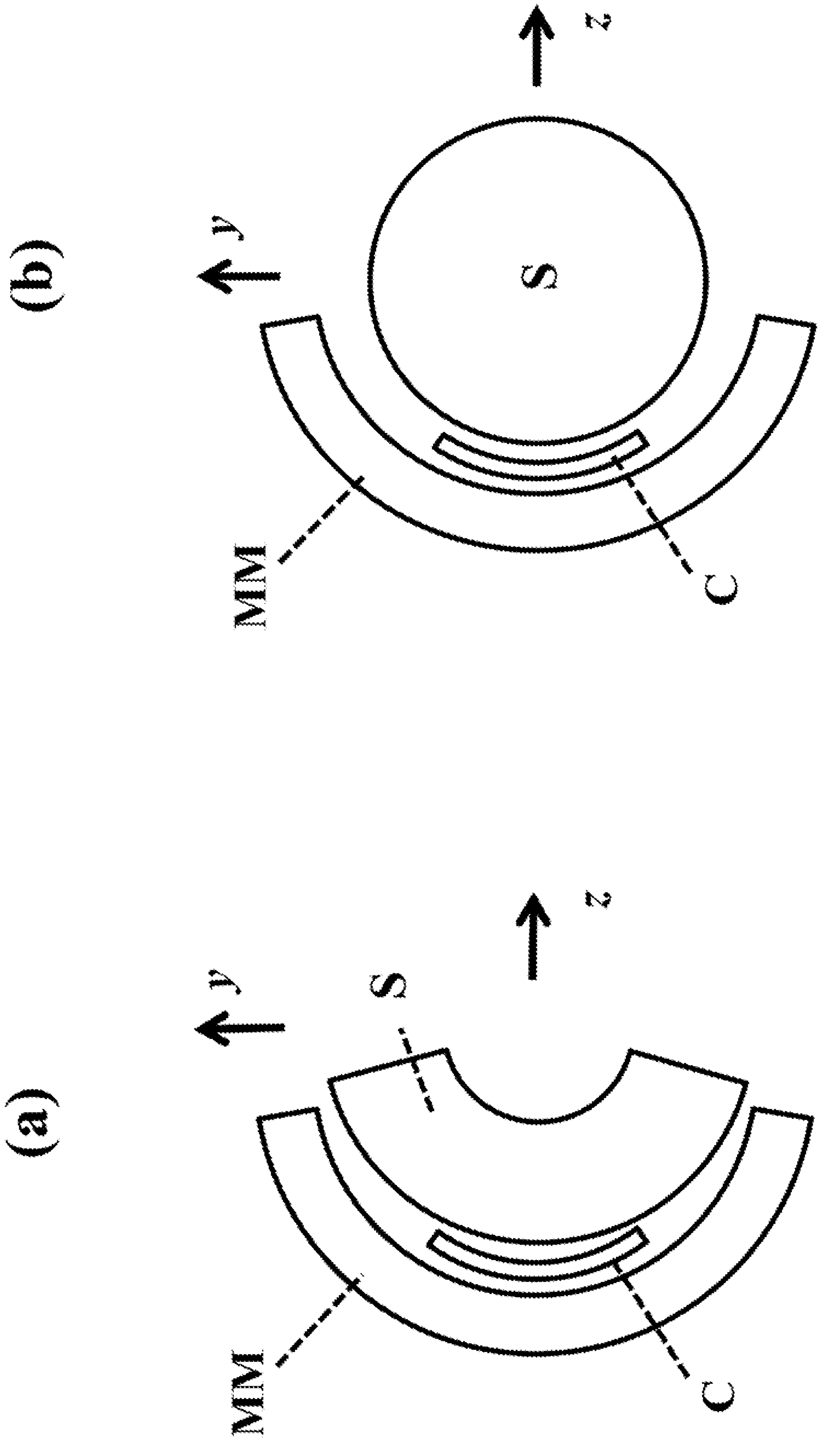

FIG. 18 in (a) shows a layout similar to the one in FIG. 1(*a*) where the three constituent elements (MM, C, S) are deformed according to a given radius of curvature; in (b)

shows a layout similar to the one in FIG. 1 (*a*) where two constituent parts are deformed to a given radius of curvature and the sample has a circular (or nearly circular) cross-section.

Figure 19:
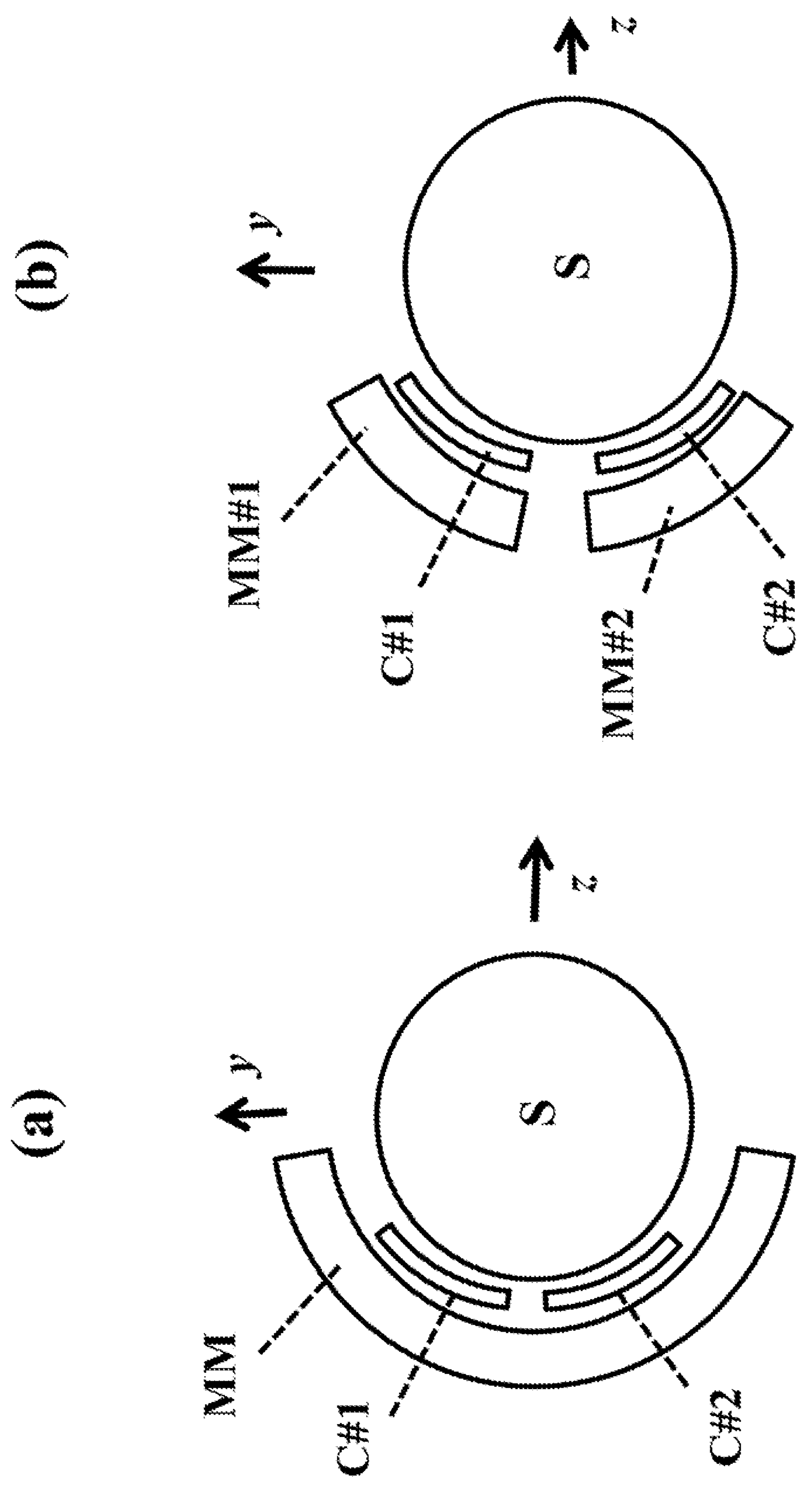

FIG. 19 in (a) shows a layout similar to the one in FIG. 1(*a*) where the metamaterial is deformed to a given radius of curvature, the sample has a circular (or nearly circular) cross-section and there are at least two RF coils which can operate in parallel mode in transmission and/or reception; in (b) shows a layout similar to the one in FIG. 1(*a*) where the metamaterial is deformed to a given radius of curvature and separated into two independent sections, the sample has a circular (or nearly circular) cross-section and there are at least two radio-frequency coils which can operate in parallel mode in transmission and/or reception.

Figure 20:
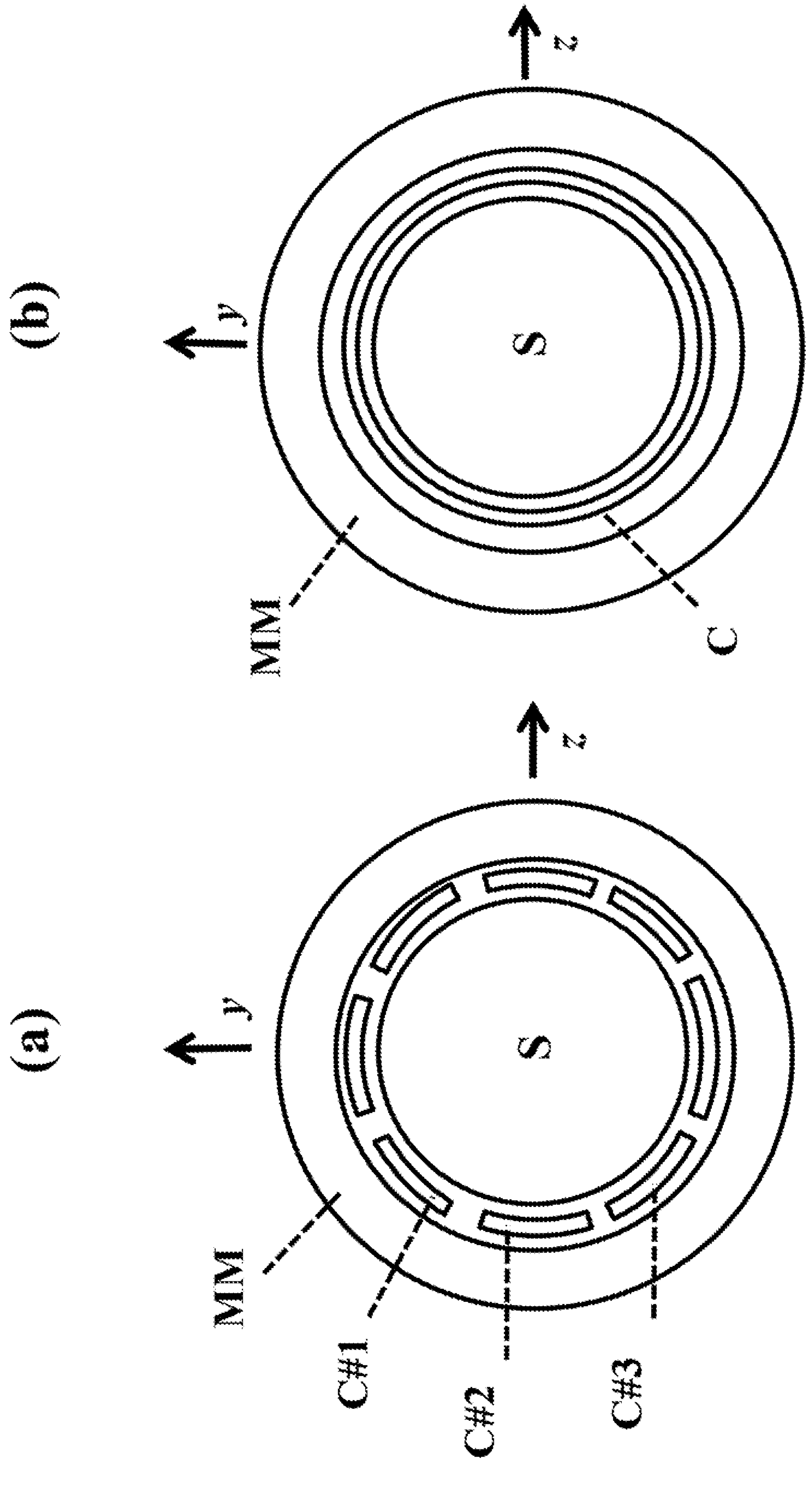

FIG. 20 in (a) shows a layout similar to the one in FIG. 1(*a*) where the metamaterial completely surrounds a sample of circular (or nearly circular) cross-section and there are at least two RF coils which can operate in parallel mode in transmission and/or reception; in (b) shows a layout similar to the one in FIG. 1(*a*) where the metamaterial completely surrounds a sample of circular (or nearly circular) cross-section and at least one RF volume coil is present (e.g. of the birdcage, multiple transmission line type) which can operate in parallel mode in transmission and/or reception; both configurations in (a) and (b) have similar advantages even if the sample does not have a circular cross-section.

Figure 21:
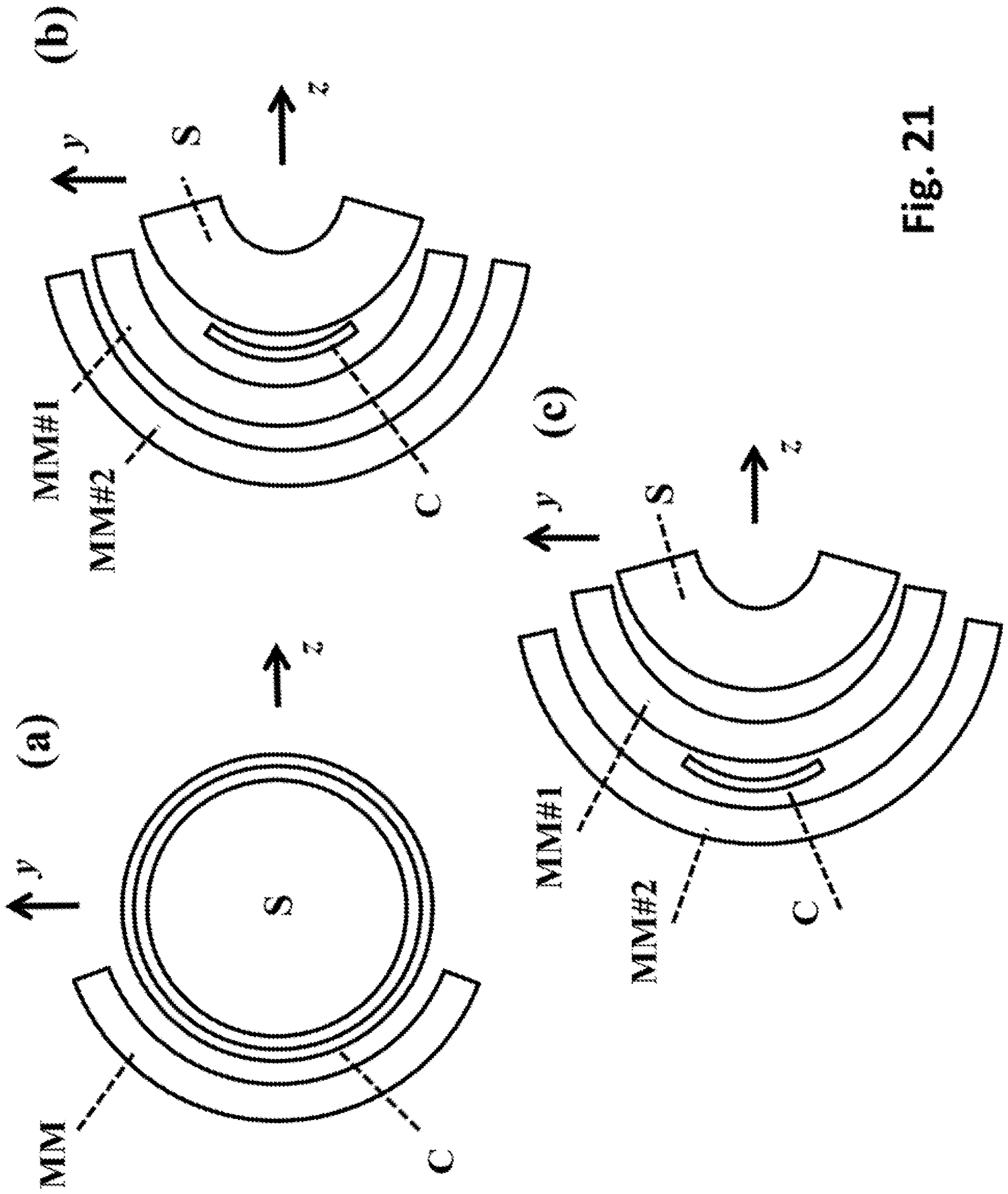

FIG. 21 in (a) shows a layout similar to the one in FIG. 20 (*b*) where the metamaterial partially surrounds the RF volume coil and the circular (or nearly circular) cross-section sample; in (b) it shows a layout similar to the one in FIG. 18 (a) where there are at least two layers of metamaterial facing the RF coil and the sample; the same configuration has similar advantages even if the sample does not have a circular cross-section; In (c) it shows a layout similar to the one in FIG. 18 (*a*) where there are at least two layers of metamaterial facing the sample, with the RF coil comprised between the two layers of metamaterial, the same configuration has similar advantages even if the sample does not have a circular cross-section.

FIG. 22 shows a layout similar to the one in FIG. 1(*a*) with the MRI configuration considered in geometry A which comprises: a RF coil of standard surface (reference "C", with radius $\rho_0$ and radial width w), positioned on the plane z=0 and placed between the magnetic metamaterial (MM) sphere (with radius $\rho_m$ and permeability $\mu_m$=[Re ($\mu_m$)+Im ($\mu_m$)] and the cylindrical sample (reference "S", with radius $\rho s$, thickness $l_s$, relative permittivity $\varepsilon_s$, conductivity $\sigma_s$, permeability $\mu_s$, positioned at a distance d, from the RF coil. $B_0$ is a homogeneous static magnetic field applied along the x-axis and $d_m$ is the minimum distance between the magnetic metamaterial and the plane of the RF coil.

FIG. 23 shows the magnetic field graph $$|B_1^{(-)}|/\mu_0$$

(solid line) and the amplitude of $SNR^{(n)}$ (solid line with star symbols), evaluated within the sample (for ρ=0 mm, z=6 mm, $d_m$=0 mm, $d_s$=2 mm), as a function of the real part of the permeability $\mu_m$, when Im($\mu_m$)=0.01. The star markers highlight the first five local peaks of $SNR^{(n)}$. As a reference, the dark dashed lines show the permeability values which allow the existence of some MLSP, defined by the equation (20), having considered a magnetic metamaterial isolated in the vacuum in the static limit approximation, with the magnetic mode index L which varies from 3 to 7 (from left to right).

Figure 24:
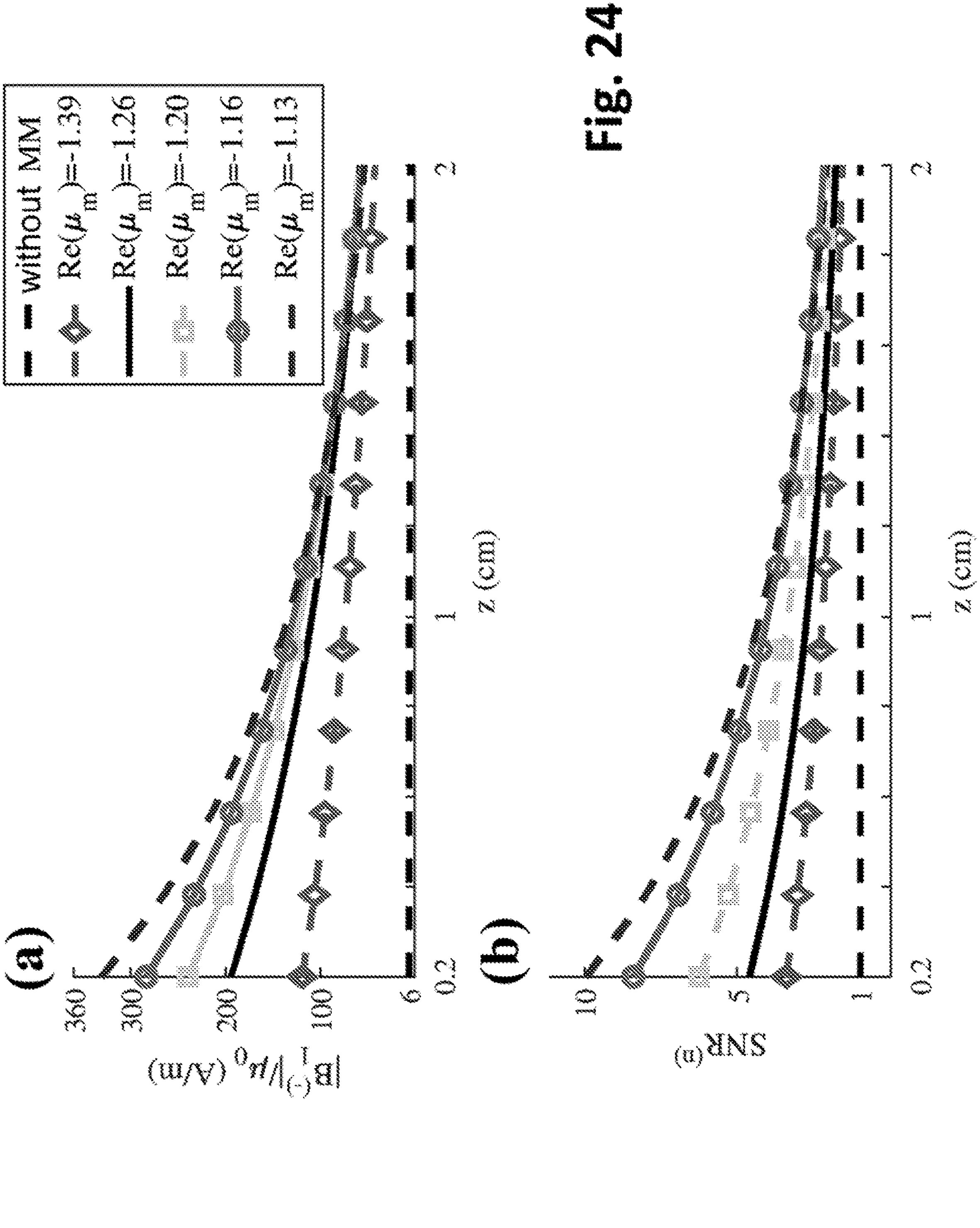

FIG. 24 shows the profiles of $$(a)\,|B_1^{(-)}|/\mu_0$$

and (b) $SNR^{(n)}$, for the geometry described in FIG. 22, evaluated along the z-axis of the sample (ρ=0 mm, z≥2 mm) for the configuration without metamaterial and for five exemplified configurations, with the metamaterial having Im($\mu_m$)=0.01 and Re($\mu_m$) corresponding to the values marked with a star in FIG. 23.

FIG. 2S shows, for the geometry described in FIG. 22: in (a) the SNR map within the sample (z≥2 mm, ϕ=π/2) without the magnetic metamaterial sphere; in (b-f) the map of $SNR^{(n)}$, with the magnetic metamaterial sphere, evaluated for Im($\mu_m$)=0.01 and Re($\mu_m$) corresponding to the values marked with a star in FIG. 23; the dashed black lines are curve lines for $SNR^{(n)}$=1.

Figure 25:
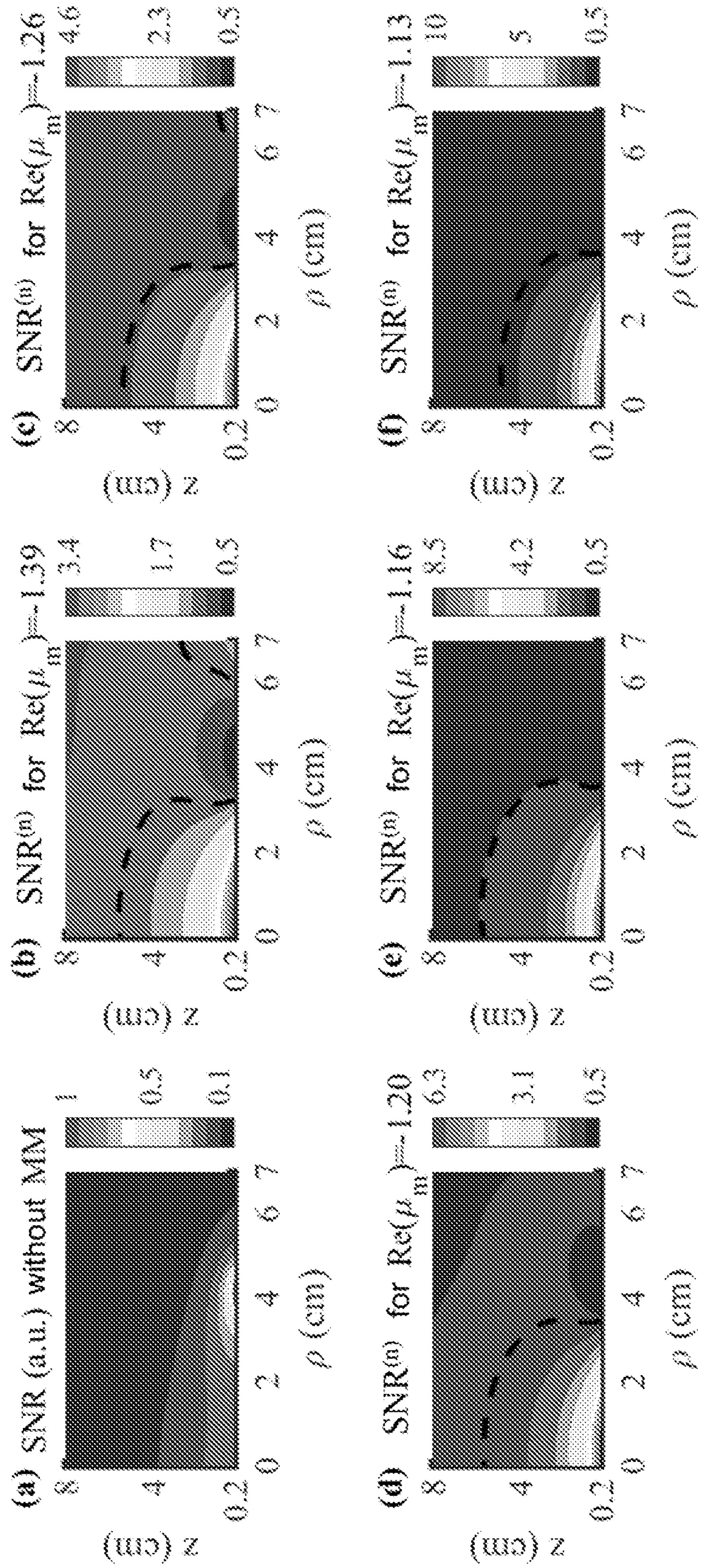
Figure 26:
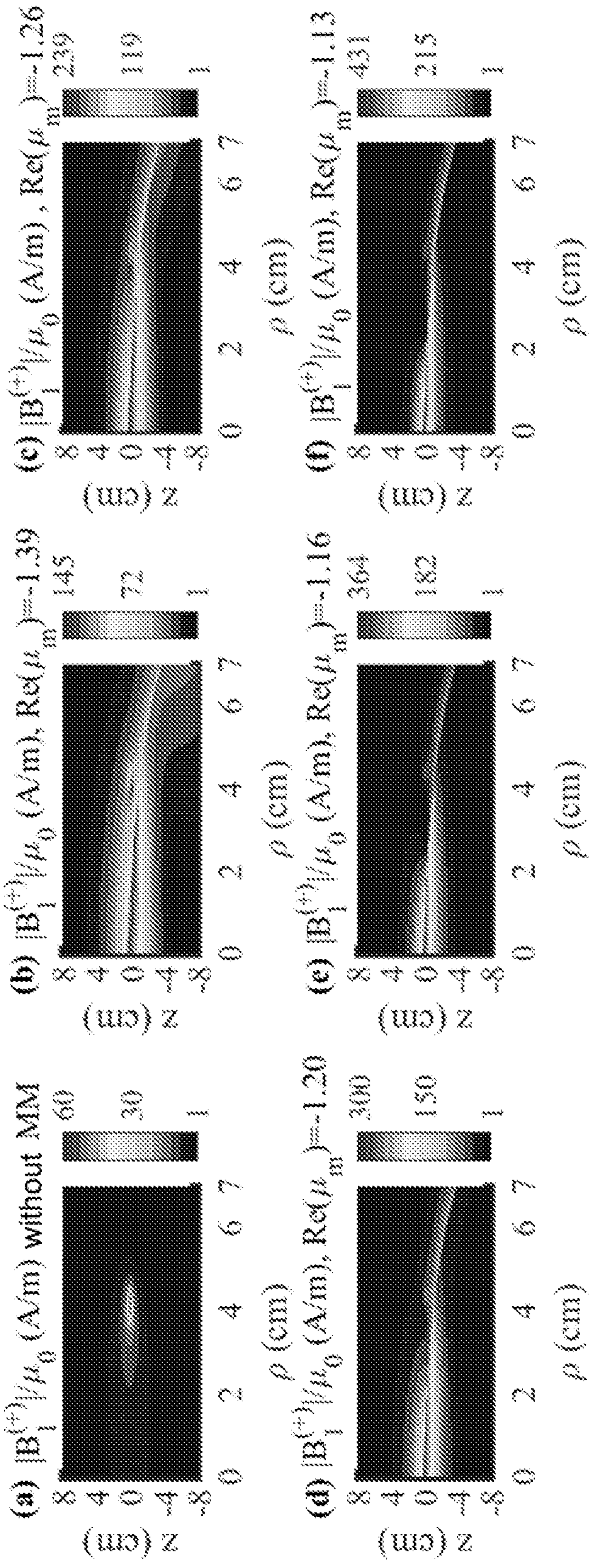

FIG. 26 shows the transmission field maps $$|B_1^{(+)}|/\mu_0$$

with geometry and parameters as in FIG. 25.

Figure 27:
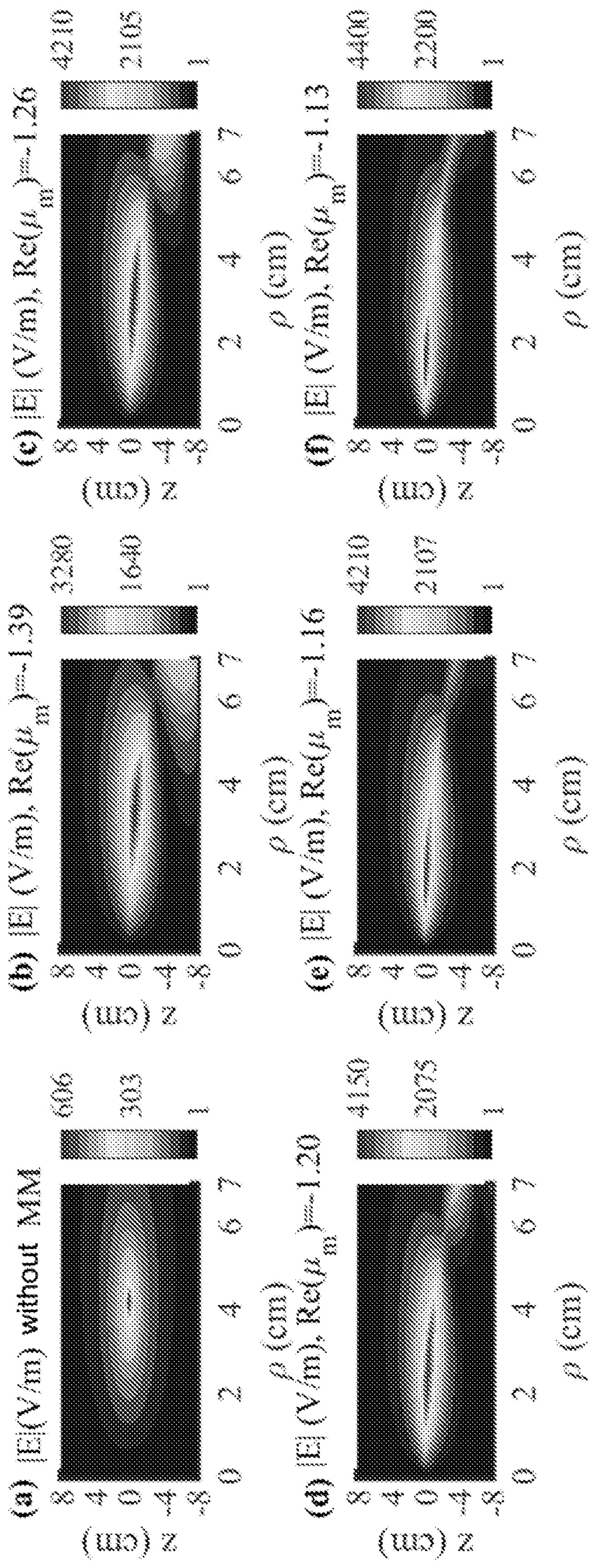

FIG. 27 shows the electric transmission field maps |E| with geometry and parameters as in FIG. 25.

Figure 28:
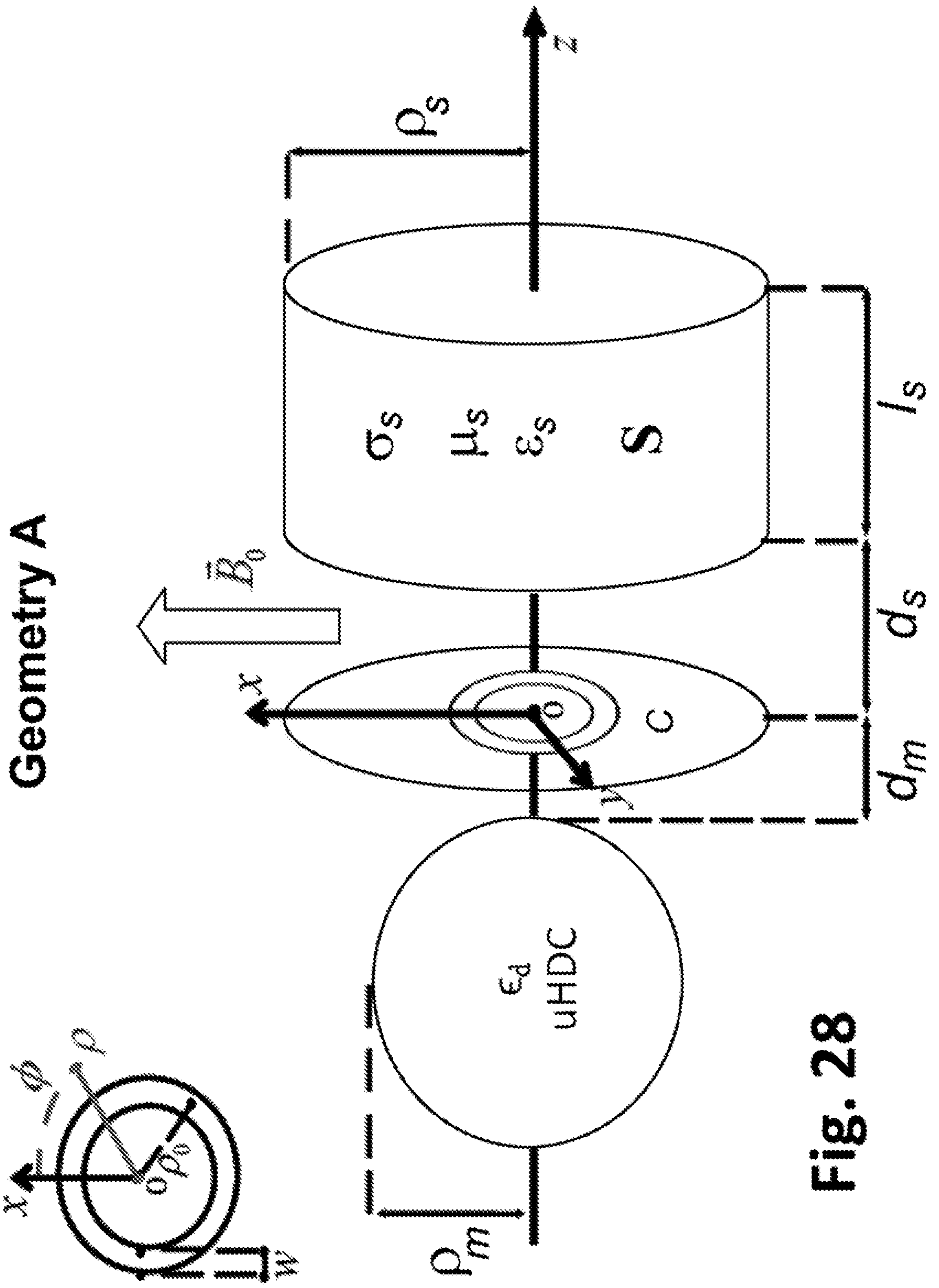

FIG. 28 shows an example layout of the MRI configuration considered with geometry A according to an embodiment of the invention. A standard surface RF coil ("C", with radius $\rho_0$ and radial width w), positioned on the plane z=0, is placed between a positive dielectric constant sphere ("uHDC", with radius $\rho_m$ and permittivity $\epsilon_d$=[Re ($\varepsilon_d$)+Im ($\epsilon_d$)] and the cylindrical sample ("S", with radius $\rho_s$, thickness $I_s$ and relative permittivity $\varepsilon_s$). $B_0$ is a homogeneous static magnetic field applied along the x-axis and $d_m$ (d) is the minimum distance between the metamaterial (the sample) and the plane of the RF coil.

Figure 29:
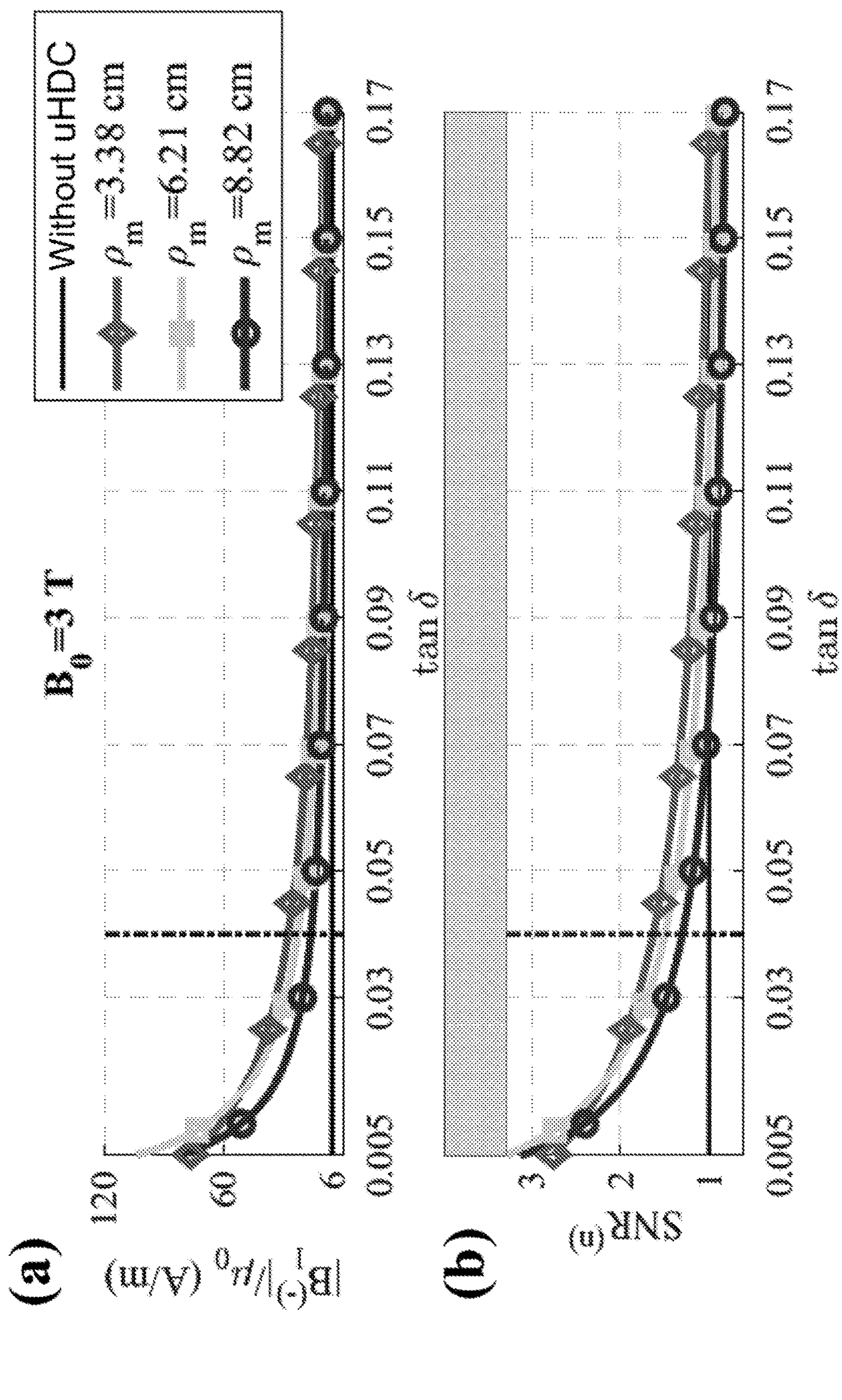

FIG. 29 shows, for the geometric configuration of FIG. 28 with Re ($\epsilon_d$)=1200 and radii $\rho_m$=3.38; 6.21; 8.82 cm which support the resonances L=1; 3; 5, respectively, at the Larmor frequency of 127.74 MHz ($B_0$=3 T): (a) the reception field $$|B_1^{(-)}|/\mu_0$$

and (b) the $SNR^{(n)}$ in point a=2 mm, ρ=0 mm as a function of the loss tangent tan δ. The lines show the evaluated values without the sphere and with several uHOC spheres, the black dashed vertical lines show the case of tan δ=0.04. The gray area at the top of the panel (b) corresponds to a tan δ range which produces a useful $SNR^{(n)}$>1.

Figure 30:
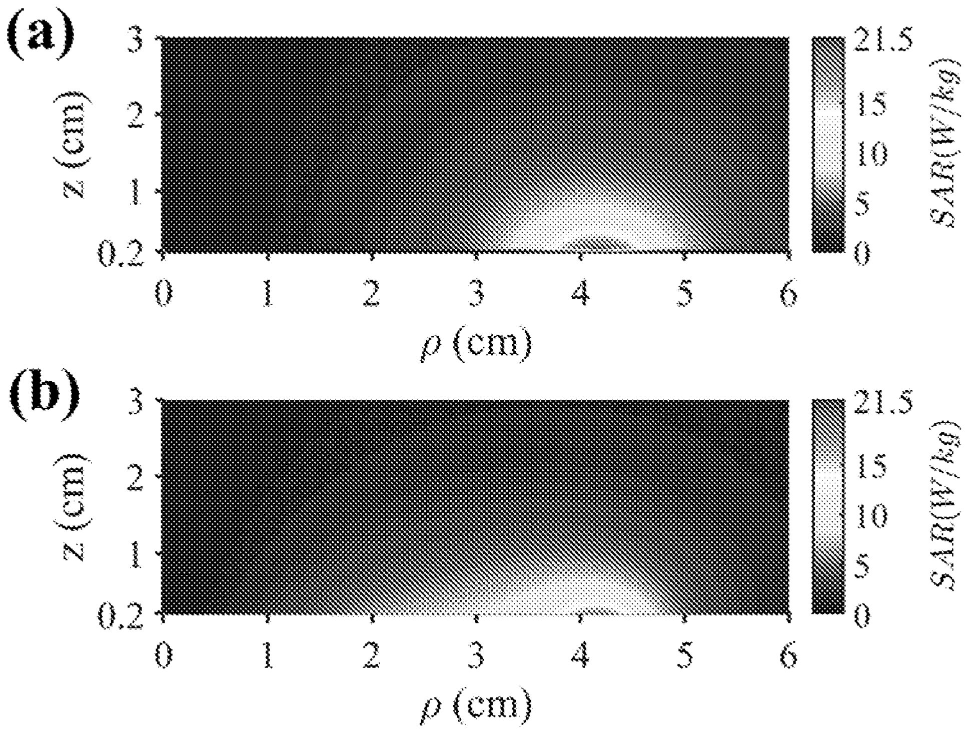

FIG. 30 shows the map in the plane (ρ, z) of the specific absorption rate SAR for the unit current at 127.74 MHz ($B_0$=3 T) with the same parameters as FIG. 29 without (a) and with (b) the uHDC sphere and for tan δ=0.04 and ρ=8.82 cm.

Figure 31:
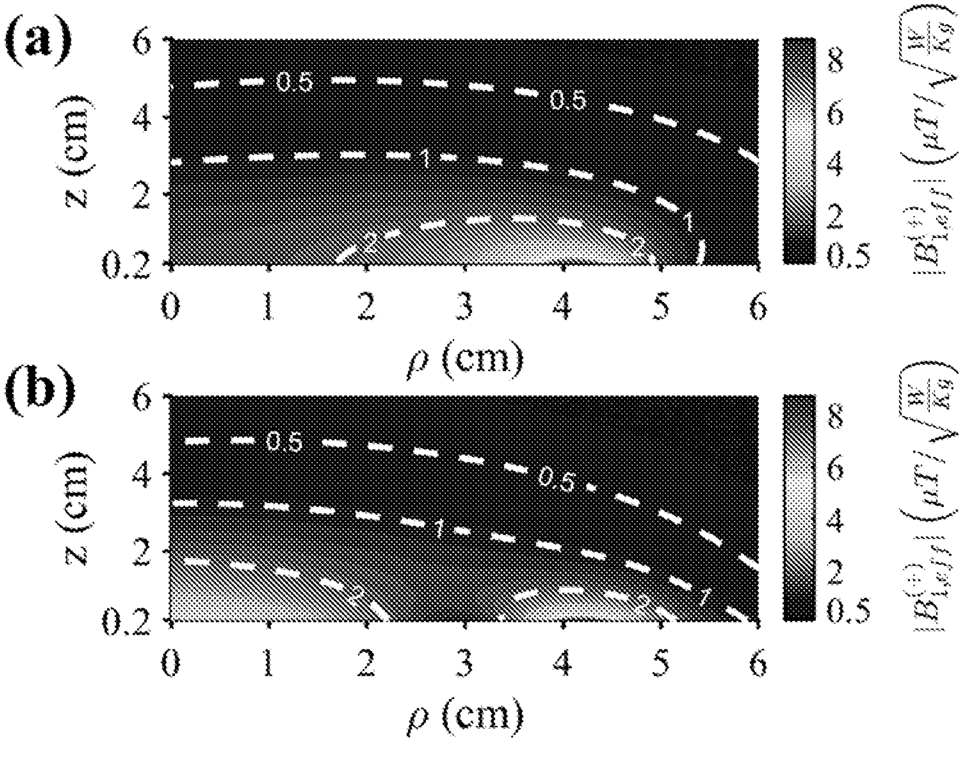

FIG. 31 shows the map in the plane (ρ, z) of $$|B_{1,eff}^{(+)}|\,(\phi = \pi/2)$$

with the same parameters as in FIG. 29 without (a) and with (b) the uHDC sphere for tan δ=0.04 and $\rho_m$=8.82 cm.

Figure 32:
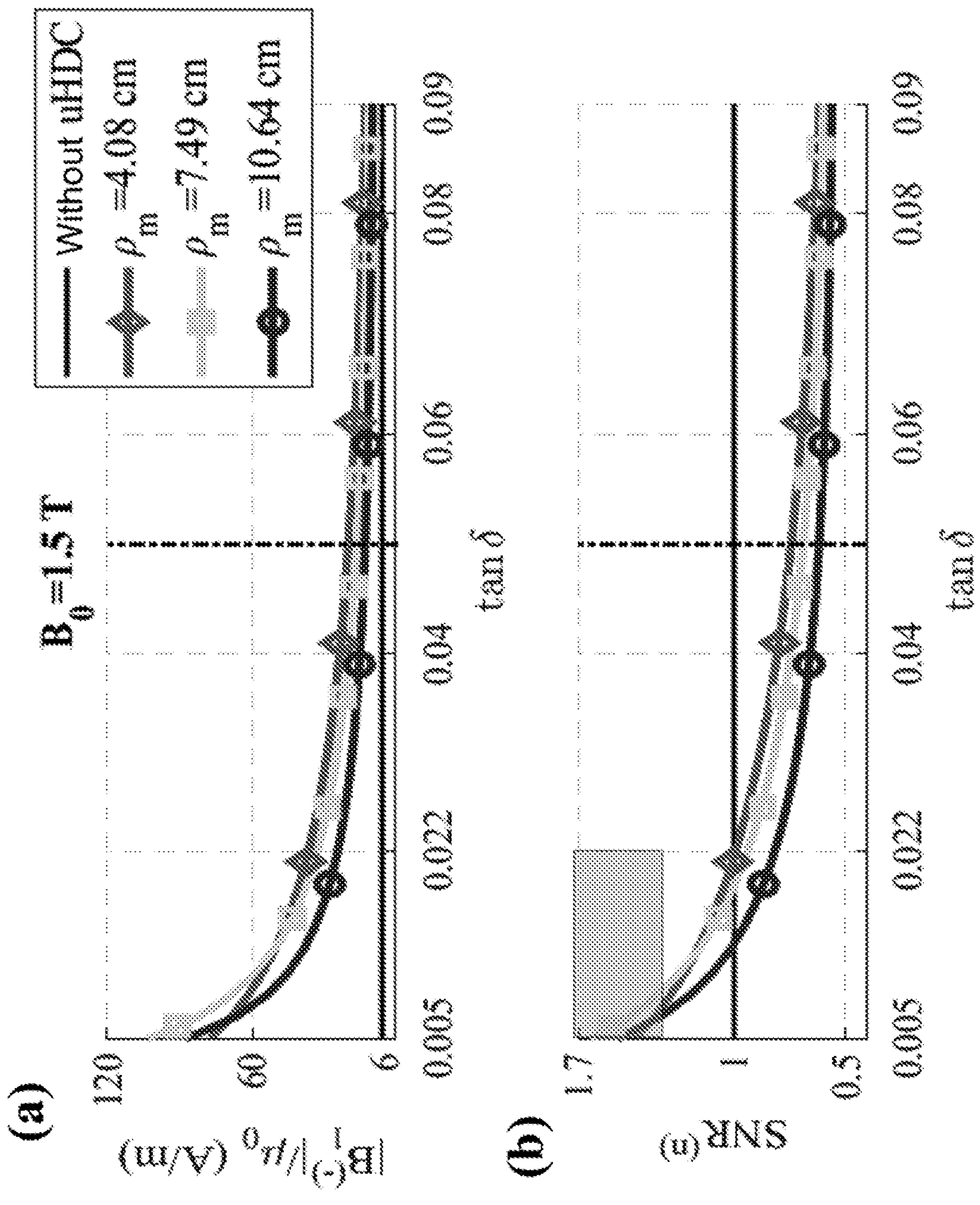

FIG. 32 shows the same geometric configuration as FIG. 28 per Re ($\epsilon_d$)=3300, radii $\rho_m$=4.08, 7.49, 10.64 cm supporting resonances L=1, 3, 5, respectively, at Larmor frequency of 63.87 MHz $$(B_0 = 1.5\ T).\ (a)\left|B_1^{(-)}\right|/\mu_0$$

and (b) $SNR^{(n)}$ at point z=2 mm, ρ=0 mm as a function of the tangent of tan losses δ. The horizontal lines without symbols are evaluated without the uHDC sphere and vertical dashed black lines highlight the case of tan δ=0.04. The gray area in (b) corresponds to a tan δ range which produces a useful $SNR^{(n)}$>1.

Figure 33:
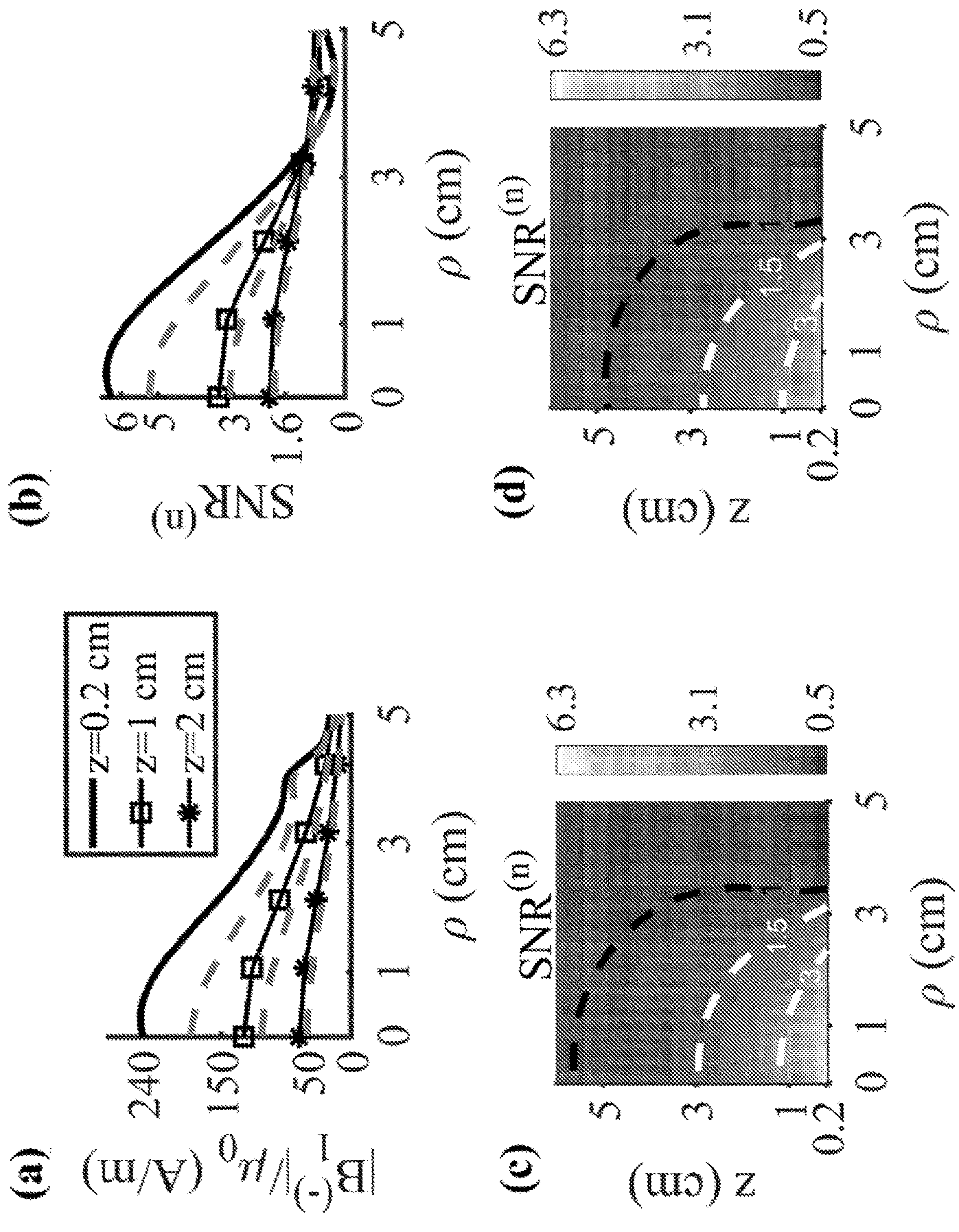

FIG. 33 shows the comparison between the geometries in FIGS. 22 and 28, respectively, with the metamaterial magnetic sphere (μm=−1.20+i0.01) and the uHDC sphere ($\epsilon_d$=1324+/1.65), with reference to resonance L=5 in both cases. The profiles of $$\left|B_1^{(-)}\right|/\mu_0$$

(a) and $SNR^{(n)}$ (b) are as a function of ρ within the cylindrical sample (z≥2 mm, ϕ=π/2) for different z-values in the presence of the magnetic sphere of metamaterial (continuous lines) or dielectric (dashed lines). The maps of $SNR^{(n)}$ for the magnetic sphere of metamaterial (c) or dielectric (d) refer to the plane (ρ, z) within the sample (z>=2 mm, ϕ=π/2). Black dashed lines are level lines for $SNR^{(n)}$=1, white dashed lines for $SNR^{(n)}$=3, and $SNR^{(n)}$=1, 5.

Figure 34:
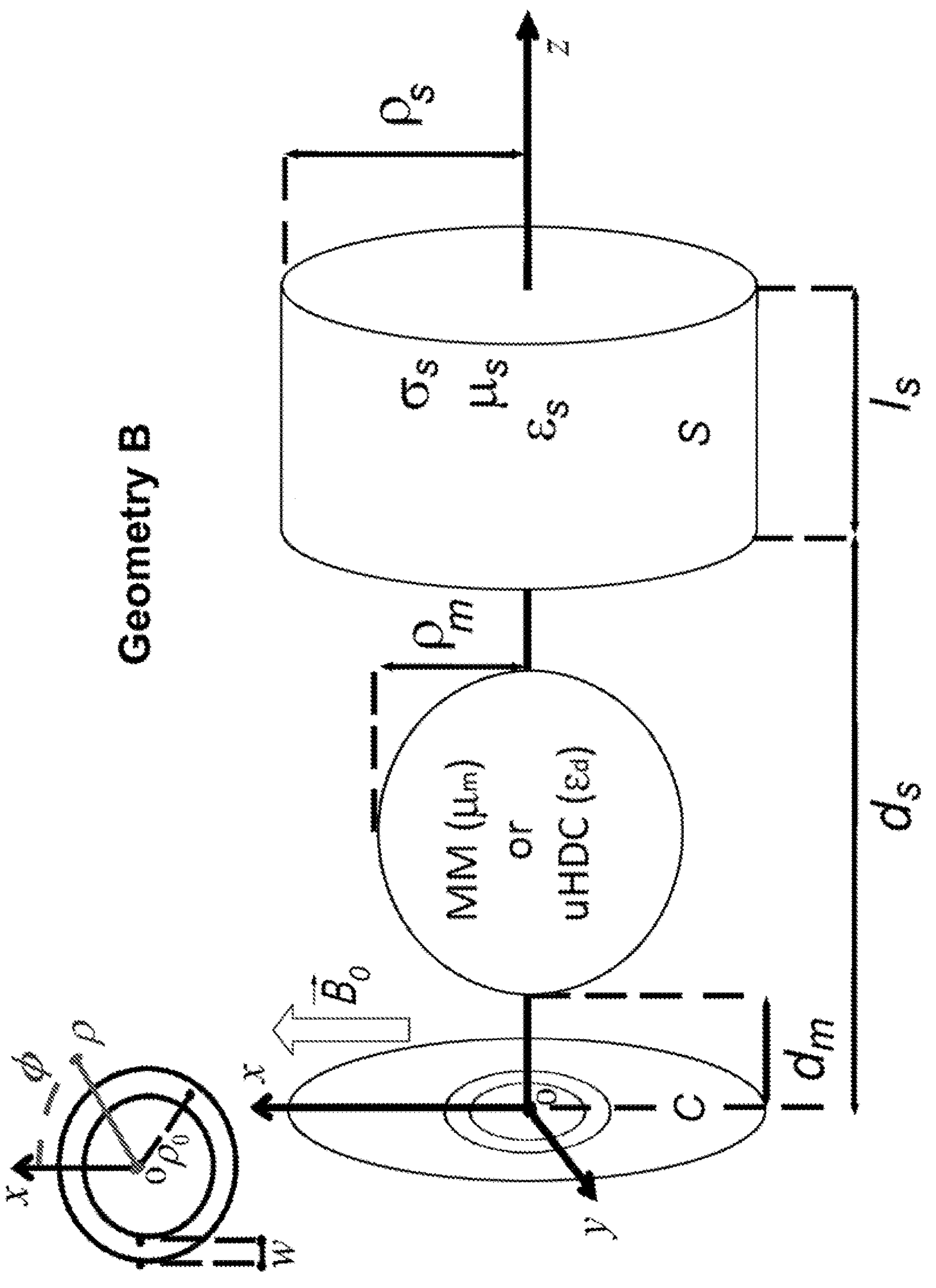

FIG. 34 shows an example layout of an MRI configuration with geometry B according to an embodiment of the invention, with the magnetic sphere MM, or uHDC positioned between a standard surface RF coil and the cylindrical sample.

Figure 35:
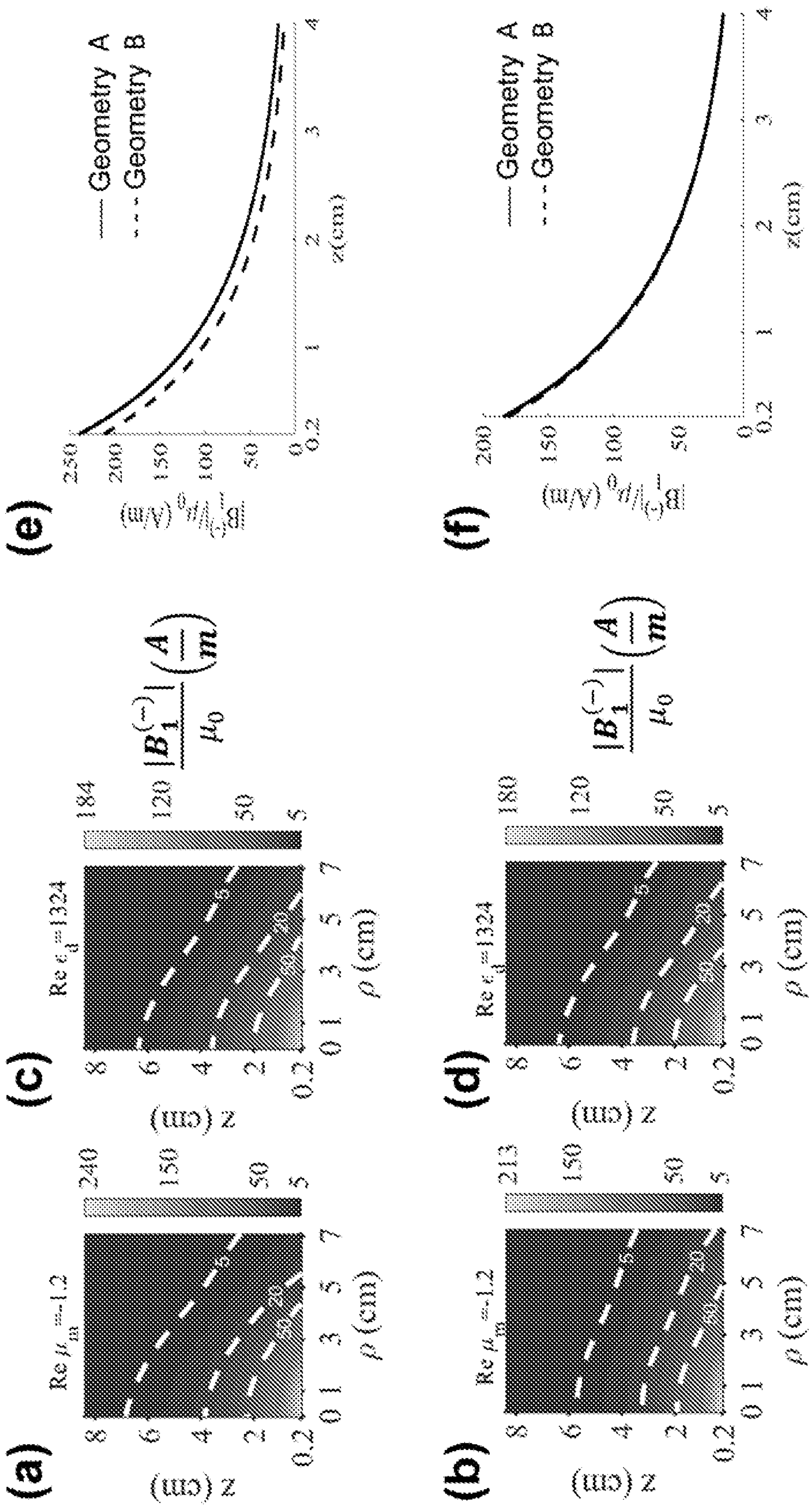

FIG. 35 shows the maps, in the plane (ρ, z), of $$\left|B_1^{(-)}\right|/\mu_0$$

inside the cylindrical sample ($d_m$=0 mm; z≥2 mm) in the presence of: magnetic sphere MM ($\mu_m$=−1.2+i0.01) with (a) geometry A ($d_s$=2 mm) or (b) geometry B ($d_s=\rho_m$+2 mm); the uHDC sphere ($\varepsilon_d$=1324+i1.65) with (c) geometry A ($d_s$=2 mm) or (d) geometry B ($d_s=\rho_m$+2 mm). Profile comparison of $$\left|B_1^{(-)}\right|/\mu_0$$

on axis ρ=0 mm for geometries A and in the presence of the MM sphere (a) or uHDC sphere (t) defined above.

Figure 36:
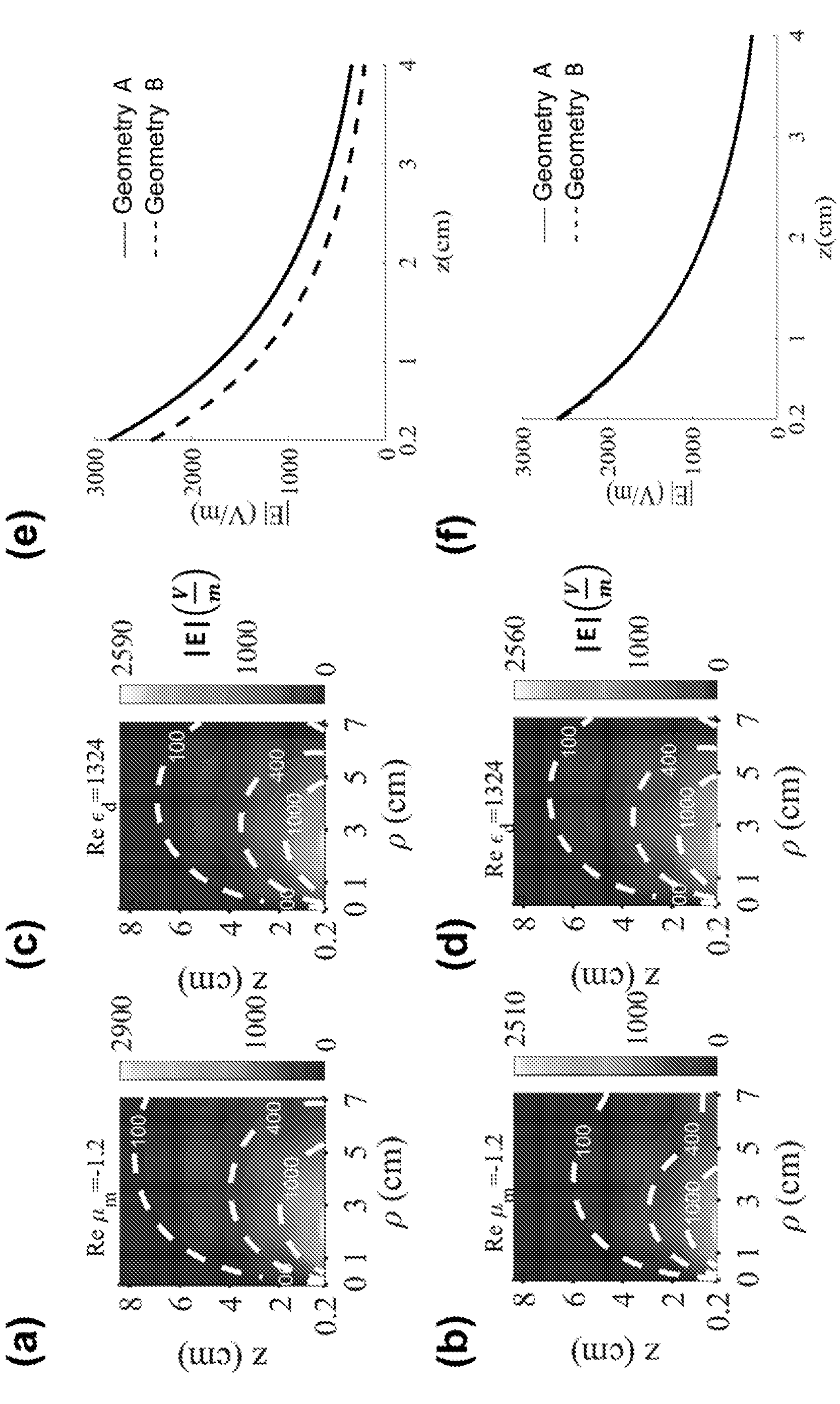

FIG. 36 shows the graphs as in FIG. 35 for the field |E|.

Figure 37:
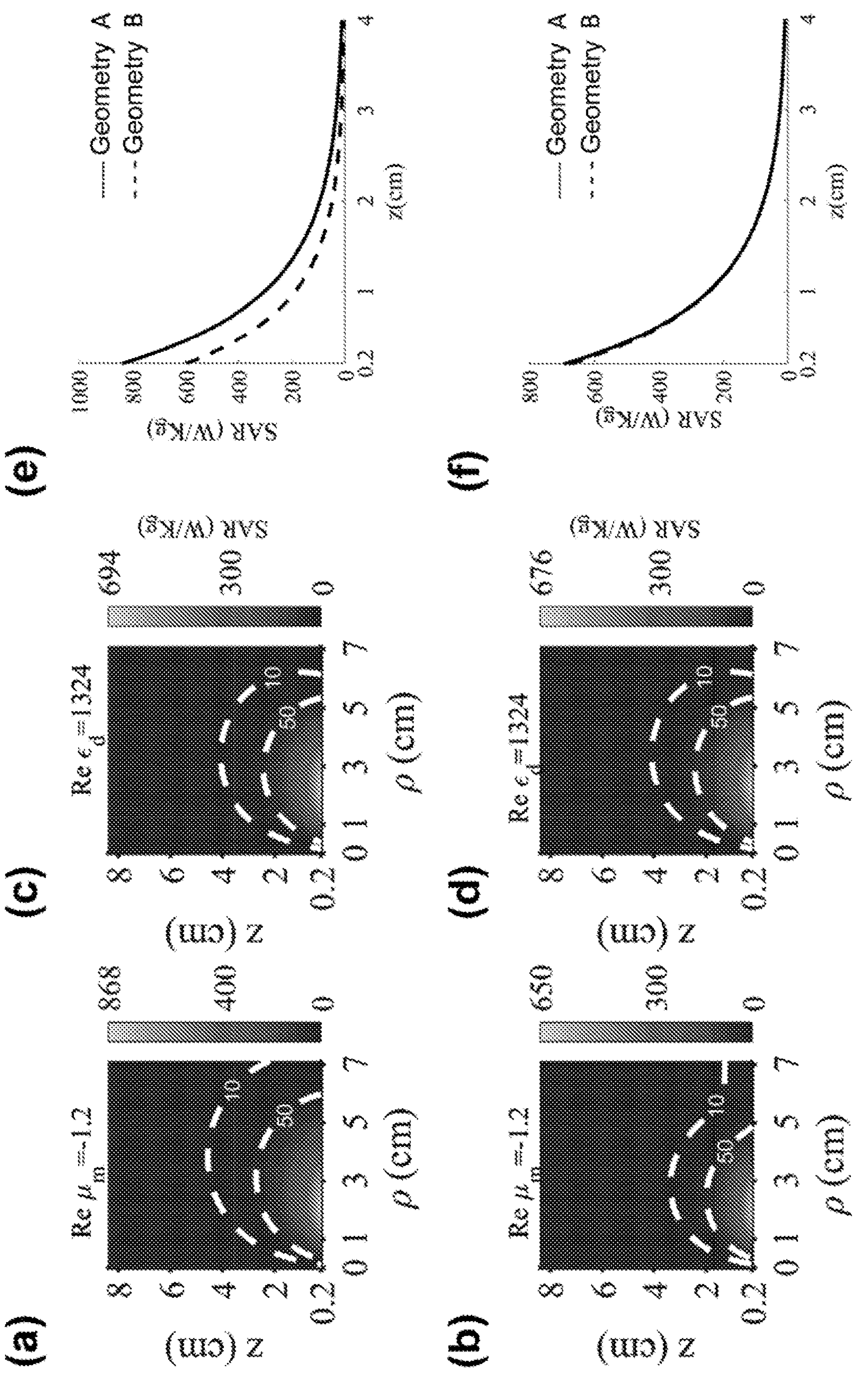

FIG. 37 shows the graphs as in FIG. 35 for the S.

It is worth noting that hereinafter elements of different embodiments may be combined together to provide further embodiments without restrictions respecting the technical concept of the invention, as a person skilled in the art will effortlessly understand from the description.

DETAILED DESCRIPTION

The present description also makes reference to the prior art for its implementation, with regard to the detail features which not described, such as, for example, elements of minor importance usually used in the prior art in solutions of the same type.

When an element is introduced it is always understood that there may be "at least one" or "one or more".

When a list of elements or features is given in this description it is understood that the invention according to the invention "comprises" or alternatively "consists of" such elements.

In the description of the embodiments, reference will generally be made to a sample to be subjected to magnetic resonance imaging (NMR/MRI/EPR/EPRI) and containing at least one electronic or nuclear spin of interest.

Furthermore, reference will be made to an "induction coil" or "RF coil" or even just "coil" meaning a coil that generates a non-static electric and/or magnetic field at radio frequencies or even microwaves or other useful frequencies. The term "RF coil" is also used in literature for frequencies other than radio-frequencies to distinguish this coil from other coils present in magnetic resonance equipment, such as coils for static magnetic fields, coils for magnetic field gradients necessary for spatial localization of the resonance signal.

Furthermore, the coil can have any cross-section shape (plane x, y in the figures) and thus in general we will speak of maximum transverse dimension instead of diameter in the circular case.

In general, the coil is tuned (e.g. In a bandwidth) about the Larmor frequency defined based on the static magnetic field and at least the electronic or nuclear spin of interest.

In this context, according to the invention, that illustrated as a technical effect for the case of magnetic plasmons also applies to electric plasmons. Indeed, the metamaterial can develop a surface plasmonic regime with electrical resonances (see [1, 3] and references cited therein), by appropriately selecting a negative dielectric permittivity value ($\varepsilon_m$).

In the case of a slab of infinite transverse dimension (dimension x, y of FIG. 1 (*a*)) and finite thickness 4, this value is equal to Re($\varepsilon_m$)=−1. An additional geometric configuration of metamaterial capable of supporting the electrical plasmonic regime is that of a sphere, the negative dielectric permittivity value of which must satisfy, with a given degree of approximation, the following condition Re($\varepsilon_m$)=−[(1+L)/L)].

The excitation means of the magnetic and/or electrical plasmonic resonance must be appropriately chosen from the possible configurations which can be divided between methods with an internal or external metamaterial source. For example, a method may be used with a small circular RF coil (or other shapes) which has its axis oriented at a given angle variable between 0° and 90° with respect to the surface of the stab of MM (i.e. relative to an axis lying in the x-y plane in FIG. 1(*a*)). Alternatively, an RF coil may be used which has at least one linear current element in the plane of the coil itself (eight-shaped coil, or double-O coil). In the prior art, resonant transmission lines (microstrip transmission lines) are also used, which have at least one linear conductive element terminating on a capacitor, the axis of which must be appropriately oriented relative to the z-axis of FIG. 1(*a*).

Therefore, the coil or the excitation means (or more generally "induction means") can also or only perform the function of excitation of electrical surface plasmons. Furthermore, as reported in the prior art of antenna theory, such excitation can occur by means of the use of a linear dipole induction coil, the main axis of which must be appropriately aligned with the electrical modes that the metamaterial can support.

In this respect, the excitation procedures of the magnetic metamaterial (finished slab, cylinder, sphere, spheroid, cube, parallelepiped, etc.) also apply to the resonance excitation method of the dielectric material, and the choice of method depends on the shape of the dielectric itself and the chosen resonance mode. The implementation details in individual cases can be obtained analytically, as in the examples below, or numerically, following methodologies well known in the literature [2] and verified by the inventors.

Embodiments

With the present invention, a step forward is made in the use of metamaterials for magnetic resonance imaging, by suggesting the use of excited surface plasmons on at least one surface of a magnetic type metamaterial (e.g. for a slab that has Re $(\mu_m)=-1$) and of electrical type (e.g. for a slab having Re $(\varepsilon_m)=-1$), as far as it is possible to approximate these conditions in reality.

For the first time, to the knowledge of the inventors, it is shown that the resonant nature of magnetic surface plasmons can be appropriately exploited to improve the efficiency of magnetic resonance imaging. Here, by way of example, a metamaterial slab will be considered characterized by Re $(\mu_m)=-1$ and incorporated in a magnetic resonance configuration as shown in FIG. 1. In this configuration, we will show that the metamaterial supports magnetic surface plasmons and their excitations can increase the magnetic field useful to excite the sample (in general, containing at least one active nuclear spin and/or an electronic spin of interest) and/or increase the magnetic resonance signal-to-noise ratio (SNR) relative to the current settings.

In an attempt to exploit the high local fields associated with surface plasmons by keeping the RF coil (or in general a coil or induction means which can also generate microwaves or other frequencies) on the surface as close as possible to the sample, there is suggested the configuration shown in FIG. 1*a*), wherein the coil C is located between the metamaterial slab MM and the sample S. The considered configuration geometry has the added advantage of not introducing limitations to the relative position between the coil C and the sample S by placing the metamaterial slab MM in a region usually free in many magnetic resonance configurations. In the situation in which the distances (or real value quantities in general, because they can be negative) $d_m$ and $d_s$ are small (compared to the dimensions of the RF col, $d_m \cong d_s \cong 0$ mm) and the thickness of the metamaterial is large (compared to the dimensions of the RF coil), we expect, based on known theories [1,2], that the metamaterial slab with $\mathrm{Re}(\mu_m)=-1$ supports the magnetic surface plasmons, which are located in a reduced thickness on the surface of the metamaterial MM facing the coil C and on the surface of the opposite metamaterial MM, away from the coil C. The magnetic surface plasmons provide, following the excitation of such resonance, a considerable increase in the electromagnetic field within the sample. By performing appropriate full-wave numerical simulations of the electromagnetic field, the configuration shown in FIG. 1 *a*) was analyzed and the spatial distribution of the non-static magnetic field, as well as the spatial distribution of the SNR, was assessed. In the numerical examples, the chosen frequency $\nu_0=63.866$ MHz (where $\nu_0$ is the Larmor frequency of the hydrogen nucleus spin corresponding to a static magnetic field $|\vec{\mathbb{B}}_0|=1.5$ T), $l_m=5.7$ cm (thickness of the metamaterial slab MM or in general dimension along said axis z between a first plane and a second plane perpendicular to the axis z which define the ends of the material along the same axis, the first plane being farther from said at least one housing of the sample S and the second plane being closer to said at least one housing of the sample S, along the axis z), $l_s=20$ cm (thickness of the sample slab), the relative permittivity of the sample $\varepsilon_s=90$ and a conductivity equal to $\sigma_s=0.69$ S/m (the latter two values corresponding to the average of the known values for human tissues at the considered frequency). The coil C is modeled with a negligible thickness along the z-axis and a surface current density which has only one azimuthal component, i.e. $J_\varphi=K_\varphi\delta(z)$, where $K_\varphi(\rho)=b_0\cdot\rho\cdot\exp[-(\rho-\rho_0)^2/w^2]$ being $\delta(\cdot)$ the Dirac delta function, $\rho_0=2$ cm, w=2 mm, $b_0$ a constant whose value allows a unit current to be defined on the coil C. Further tests were done with $l_m$ between 1 cm and 5.7 cm still achieving an increase in signal-to-noise ratio. For values smaller than 1 cm, we noted that the improvement introduced by one side of the slab was canceled by the contribution of the other. In general, it can be said that $l_m>1/10$ of the transverse dimension (relative to the z or the coil axis) of the maximum induction coil C, however this is a preferred value and the minimum quantity depends on the whole system configuration: it can be calculated each time with analytical and/or numerical methods or by experimentally verifying the existence of plasmonic regimes and the effect of the electromagnetic field produced in the sample in each position of interest (it could affect only a very narrow area of the sample and consequently only some configurations of the magnetic plasmonic regime or dielectric regime resonances).

Although the distance $d_s$ should ideally be close to or equal to 0 mm, for safety reasons it is still set to a few mm, in any case preferably less than 1 cm. More in general, the maximum distance $d_s$ between said at least one induction coil C and said at least one sample S housing (relative to a plane tangent to its end along the axis z closer to the metamaterial or dielectric material) is comprised in the range from 0 to the maximum transverse dimension of the induction coil.

In general, the distance $d_m$ is defined between at least one metamaterial MM and at least one induction coil C, or also as the difference between the position along the axis z of the induction means C and the position along the z axis of the first plane of the metamaterial MM or the dielectric material uHDC. $d_s$ can instead be defined as a real values quantity which represents the difference between the position along the z axis of the sample S housing and the position along the z axis of the induction means C. Both can be comprised in the range from 0 to the maximum transverse dimension of the induction coil, preferably between 0 and 1/10 of the maximum transverse dimension of the induction coil. $d_s$ can be comprised between 0 and 1 cm. It is worth noting that in all embodiments the various components S, MM, uHDC, Care positioned one after the other (in the order given each time or claimed) along the z-axis, but this does not mean that they must have symmetry relative to this axis or cannot be offset in directions perpendicular to such axis.

It is possible to obtain the aforesaid static magnetic field through a permanent magnet, or an electromagnet, or a superconducting magnet, or in general by means of a static magnetic field.

In a generic configuration for magnetic resonance, the signal from the sample detected by an RF coil is given by $$S \propto \left|B_1^{(-)}(\rho, \phi, z)\right|.$$

Considering the geometry shown in FIG. 1 *a*), where $\vec{\mathbb{B}}_0$ is along the x-axis, it holds $$B_1^{(-)} = (B_{1\rho}\sin(\phi) + iB_{1z})/2,$$

where the RF magnetic field in cylindrical coordinates is given by $\vec{\mathbb{B}}_1(\rho, \phi, z) = \mathrm{Re}[(B_{1\rho}\hat{\rho} + B_{1z}\hat{z})e^{-i\omega t}]$, with $\omega = 2\pi\nu$ and $\nu$ the Larmor frequency of the spin of interest. On the other hand, the noise received by the RF coil is proportional to the square root of the power P dissipated in the system, so that the SNR of the receiving RF coil is $\propto$ $$\left|B_1^{(-)}\right|/\sqrt{P}.$$

After the RF coil losses, the power dissipation is expressed as $P = P_s + P_m$, where $P_s$ and $P_m$ are the power dissipated in the sample and the metamaterial, respectively. To highlight the advantages related to the presence of the metamaterial slab, hereinafter we will consider the normalized signal-to-noise ratio $SNR^{(n)}$ defined above.

The advantages related to the presence of the metamaterial slab are apparent in FIGS. 2, 3, 4 which show, as provided by the known theory, a resonant behavior of the RF magnetic field (continuous curve) and, more importantly, the $SNR^{(n)}$ (curve with square symbols) becomes greater than one in the plasmonic resonance condition (e.g. in FIG. 2 *b*) $SNR^{(n)} \simeq 5$ for $\mu_m = -1 + i10^{-3}$).

To physically understand the role of surface plasmons and the results shown in FIG. 2-4, we have analytically solved Maxwell's equations in the configuration in FIG. 1 *a*) where, for simplicity of calculation, we considered that the sample is a semi-infinite slab in the direction of the z-axis (i.e. $l_s \to \infty$). Taking advantage of the rotational symmetry of the system about the z-axis, the complex amplitudes of the electric and magnetic fields can be written as $E_\phi = i\omega A_\phi$, $B_1 = \nabla \times A_\phi$, where $A_\phi$ is the azimuthal component of the electromagnetic potential vector. We then look for solutions to Maxwell's equations using the Hankel transform to express $$A_\phi(\rho, z) = \int_0^{+\infty} dk_\rho k_\rho J_1(k_\rho \rho)\tilde{A}_\phi(k_\rho, z).$$

Within the static limit, two relevant regimes can be highlighted:

(i) the Pendry regime, in which the metamaterial slab with $\mathrm{Re}(\mu_m) = -1$ can behave like a Pendry lens, if the spatial spectrum of the $\tilde{K}_\phi(k_\rho)$ (Hankel transform of density current $K_\phi(\rho)$) is different from zero in the region of $$k_p \ll k_1, \tag{1}$$

(ii) the plasmonic regime, in which a metamaterial slab with $\mathrm{Re}(\mu_m) = -1$ supports surface plasmonic excitations, in the situation where $\tilde{K}_\phi(k_p)$ is not null in the region of $$k_\rho \gg k_1, \tag{2}$$

being the parameter $$k_1 = l_m^{-1}\log\left[2/\mathrm{Im}(\mu_m)\right]$$

defined by the geometry of the metamaterial slab and its losses, identified by the imaginary part of $\mu_m$. In general, we may also have a less important plasmonic regime for $k_\rho > k_1$.

In regime (i), the overall amplitude of the potential vector in the region occupied by the sample is $$A_\phi(\rho, z > 0) \simeq -\frac{\mu_0\mu_m}{2}\int_0^{+\infty} dk_\rho J_1(k_p\rho)\tilde{K}_\phi e^{-k_\rho z} \tag{3}$$

while, in the plasmonic regime (ii), we obtain $$A_\phi(\rho, z > 0) \simeq \frac{\mu_0\mu_m}{1+\mu_m}\int_0^{+\infty} dk_\rho J_1(k_\rho\rho)\tilde{K}_\phi e^{-k_\rho z}. \tag{4}$$

The Pendry mechanism applies to plane waves whose transverse wave number satisfies condition (i) $k_\rho \ll k_1$ and this corresponds to a minimum resolution relative to the image $\Delta = 2\pi l_m/\log[2/\mathrm{Im}(\mu m)]$ [2]. Considering the definition of $K_\phi(\rho)$, it can be understood that this regime is achieved when the coil size ($\rho$) is very large. On the other hand, if the RF coil is small enough, a significant portion of the spatial spectrum of $K_\phi(\rho)$ can be found in the region $k_\rho > k_1$, where surface plasmons can be excited. It is worth noting that equation (3) with $\mu_m = -1$ coincides with the expression of the field potential if the metamaterial is absent. Consequently, in the regime (i) and configuration of FIG. 1 considered here, the metamaterial does not influence the spatial distribution of the electromagnetic field within the sample. From Eq. (4), it is apparent that a very large increase in the amplitude of the field $A_\phi$ can be obtained in the condition $\mathrm{Re}(\mu_m) = -1$ and $\mathrm{Im}(\mu_m) \ll 1$. This condition corresponds to the existence of electromagnetic modes located on the surface of the metamaterial at z=0 (with a skin depth which depends on the losses of the metamaterial). If we suppose to use the RF coil shown in FIG. 1 for the reception of the magnetic resonance signal, the intensity of the received signal, as indicated above, depends on the RF field $B_1^{(-)}$ and condition (ii) may lead to increase it resulting in increased performance of the magnetic resonance system.

From the theoretical analysis (in the approximation of static regime), the amplitude of the magnetic resonance signal is proportional to the function $$f(\mathrm{Re}(\mu_m) \mid \rho, \phi, z) = \left|\frac{\mathrm{Re}(\mu_m) + i\mathrm{Im}(\mu_m)}{1 + \mathrm{Re}(\mu_m) + i\mathrm{Im}(\mu_m)}\right|\left|B_1^{(-)}(\rho, \phi, z)\right| \tag{5}$$

which has a maximum, once the spatial position has been fixed, for $\mathrm{Re}(\mu_m) = -1$. The full width at half maximum (FWHM) of the function depends on the imaginary part of the relative magnetic permeability and is about $2\mathrm{Im}(\mu_m)$. From this, it follows that in an optimized configuration the relative magnetic permeability $\mu_m$ of the metamaterial is such that $\mathrm{Re}(\mu_m)$ is in a range around the value $-1$, said range being equal to $2\text{-}\mathrm{Im}(\mu_m)$.

The physical mechanism considered here is very different from that suggested by Pendry. The Pendry mechanism is due to the fact that the evanescent waves show an exponential, non-intuitive growth within the metamaterial so that the wave modes emitted by the source, which satisfy condition (i), can be transmitted without diffraction for an adequate lens thickness. Instead, the surface plasmons located near the surface of the metamaterial exist in the opposite regime (ii), in which the wave modes satisfy the condition given by Eq. (2). In this regime, the metamaterial with Re(μ)=−1 does not behave like a lens and can produce a hyperfocusing of the electromagnetic field near the surface of the metamaterial.

The spatial visualization of the mechanism is given by FIGS. 5, 6, 7 which show the spatial distribution of $SNR^{(n)}$ and of $$B_1^{(+,n)}.$$

For $Im(\mu_m)=10^{-1}$, we obtain a significant spatial modulation of $SNR^{(n)}$ and the losses, within the metamaterial, are responsible for an overall reduced performance of the receiving system ($SNR^{(n)}<1$ throughout the explored region). Considering $Im(\mu_m)=10^{-3}$ ($Im(\mu_m)=10^{-2}$), near the surface of the slab, the plasmonic excitation results in a more intense RF electromagnetic field and a strong improvement in $SNR^{(n)}$, i.e. $SNR^{(n)}\simeq 7.5$ ($SNR^{(n)}\simeq 2.5$). In FIG. 5-7, dashed lines indicate isolines with $SNR^{(n)}=1$. From FIG. 5 it is apparent that, for the considered geometry, with $Im(\mu_m)<10^{-3}$, the value of SNR which can be achieved in a magnetic resonance experiment, in the presence of metamaterial, may be increased, by a high factor, in the region $0\leq\rho<7$ cm and $0\leq z<2.5$ cm.

To evaluate the impact of surface plasmon excitations on the signal transmitted by an RF coil, we will consider the spatial distribution of the excitation field (transmission)

$$B_1^{(+)} = (B_{1\rho}\sin\phi - iB_{1z})^*/2$$

normalized to the current in the RF coil (C) (FIGS. 6, 7). As predicted by theoretical analysis, as $Im(\mu_m)$ decreases, the value of $k_1$ increases [see Eq. (2)], the excited wave modes are more closely confined near the metamaterial-vacuum interface, and the amplification factor increases (Eq. (4)). Consequently, a possible application of the setup according to the invention is related to the transmission phase of the magnetic resonance signal. The high field increase $|B_1^{(+,n)}|$ can increase the transmission performance of the system by allowing much shorter RF pulses and/or the use of less powerful RE amplifiers (with cost savings and system management), the flip angle of the macroscopic magnetization of the sample in presence of the static magnetic field being equal. Such an effect may be possibly beneficial, also when multiple RF transmission coils are available, to implement parallel transmission magnetic resonance imaging techniques.

FIG. 8, for the sake of completeness, shows the spatial trend of the normalized electric field which is observed at three geometric configurations in which the mutual distance between coil and/or metamaterial and/or sample varies by a few millimeters.

Diagrams for the use of metamaterials are given below, but the conclusions are also valid when using a dielectric material appropriately shaped and with a permittivity value (uHOC) selected ad hoc so that it reproduces an equivalent electromagnetic field (with good approximation) relative to that produced by a magnetic and/or electrical metamaterial (see the example of the sphere of magnetic MM below). To better quantify the advantages which can be obtained with the present invention. FIGS. 9-17 show quantities $|B_1^{(+)}|$ and $SNR^{(n)}$ as a function of the depth z in the sample, for different geometric configurations and their dependence on the thickness of the metamaterial slab.

Now with reference to FIGS. 18-21, we will illustrate some examples of possible geometries of the inventive layout of FIG. 1(*a*).

In the first of these embodiments, the three basic constituent elements are deformed according to a given radius of curvature, in particular in the variant of FIG. 18(*a*) the RF induction coil C, sample S and metamaterial MM all have substantially circular ring sections, although the lengths of the sections may vary, e.g. the length of coil C is less than the length of the other two elements. In the variant of FIG. 18 (*b*), the sample section is circular. In the case of the two opposite faces of the slab, the minimum radius of curvature of at least one of the two opposite faces of the slab is greater than the maximum transverse dimension of the induction coil.

Furthermore, in FIG. 18 as in each of the other figures and embodiments and variants, the sample must be understood as a volume of interest in the matter placed in a housing (not shown) of the magnetic resonance apparatus according to the invention. So, for example, the sample in FIG. 18 (*b*) may be an ROI within a body with a cubic outer shape, without loss of generality.

The embodiment in FIG. 19 comprises the elements as in FIG. 18 (*b*), in which the sample has a circular cross-section but the RF induction coil C is double, with shorter sections and the metamaterial MM is an arc of circumference in a single piece or is double, in this case consisting of identical or different MM elements based on the local properties of the sample adjacent to each one. The same applies to a subdivision of the RF coil elements into several parts, beyond the two shown, which can operate in parallel mode in transmission and/or reception.

The embodiment in FIG. 20 comprises in (a) a whole or almost whole-ring metamaterial and a circular section sample, while a plurality of curved RF coils C#1, C#2, C#3, etc. is present and in (b) instead there is a ring-shaped RF coil, which is also a whole or an almost whole ring. For these cases, the specifications on the plasmonic regime—and therefore on the choice of the metamaterial—can be calculated by numerical simulation.

Again, in the embodiment in FIG. 21(*a*) only the metamaterial is not circular in section, but extends for an arc of circumference, while in the embodiment in FIG. 21(*b*) there are two metamaterials (MM #1 and MM #2) along two concentric arcs of circumference and now the sample also extends along an arc of circumference. In general, there may be more than two metamaterials even nonconcentric, and also flat. The combination of surface plasmonic resonances determined by the geometry and magnetic permeability of the two metamaterials (MM #1 and MM #2), coupled through at least one RF coil, will produce an RF magnetic field distribution inside the sample which can be modulated appropriately with beneficial effects for the magnetic resonance experiment.

Following the principle described in FIG. 1(*a*), the case of a slab of thickness $l_m$ and finite transverse dimension can also be considered. In this case, the geometric figure of the slab is transformed into that of a cylinder with one of the bases facing towards the circular coil. Such geometry may be modified, without losing the effectiveness of the metamaterial, by rotating the cylinder by an angle between 0° and 90°, i.e. by orienting its axis of symmetry in a direction which goes from parallel to perpendicular to the z-axis. Here, too, the specifications on the plasmonic regime can be calculated numerically.

Examples of Study of Operation

I. Details on the Numerical Simulation

The full-wave numerical results shown in FIGS. 2, 3, 4 are obtained by means of the commercial software package COMSOL Multiphysics. Taking advantage of the invariance by rotation around the axis of the RF induction coil (i.e. the axis z), we have performed 2D simulations the validity of which has been confirmed, in some specific geometries, by 3d full-wave simulations performed with Ansys Electromagnetic Desktop software. In the simulations, we will consider a finite dimension spatial domain in which, along the axis z, we considered two (not shown) vacuum regions of thickness $l_v$=8.5 cm, the first at the metamaterial surface far from the RF coil and the second beyond the sample. Furthermore, perfect electrical conductor (PEC) boundary conditions haw been imposed on the spatial domain frontier. We used appropriate non-homogeneous spatial domain discretization with a maximum grid dimension of 1.5 mm (about $8\times10^5$ degrees of freedom).

II. RF Coil Signal Calculation in an NMR/MRI Apparatus

In the configuration considered in FIG. 1, the RF coil can be used to transmit an RF pulse or receive the induction signal caused by the spin of the sample. Bearing in mind that the static magnetic field $\vec{\mathbb{B}}_0$, in FIG. 1 *a*), is along the axis x, the RF magnetic field $\vec{\mathbb{B}}_1$=Re[$B_1 e^{-i\omega t}$] (ω is the angular frequency of the radiation) can be broken down into two contributions $$B_1^{(+)} = \frac{(B_{1y} - iB_{1z})^*}{2},\qquad B_1^{(-)} = \frac{B_{1y} + iB_{1z}}{2}, \tag{6}$$

where $B_1=B_{1x}\hat{e}_x+B_{1y}\hat{e}_y+B_{1z}\hat{e}_z$ is the alternating magnetic field per unit current flowing in the RF coil. Here we will use the symbols $B_1^{(\pm)}$ to distinguish the two circular polarizations which rotate in opposite directions: $B_1^{(+)}$ is the polarized field rotating in the same direction as the spin precession (transmission), $B_1^{(-)}$ is the counter-rotating component (reception). Considering the cylindrical coordinates (ρ, ϕ, z), as defined in FIG. 1, the previous equations become $$B_1^{(+)} = \frac{(B_{1\rho}\sin\phi + B_{1\phi}\cos\phi - iB_{1z})^*}{2},\qquad B_1^{(-)} = \frac{B_{1\rho}\sin\phi + B_{1\phi}\cos\phi - iB_{1z}}{2}. \tag{7}$$

In our simulations, the surface current density has only one azimuthal component and the system has rotational symmetry, so we can write $$B_1^{(+)}(\rho, \phi, z) = \frac{(B_{1\rho}\sin\phi - iB_{1z})^*}{2},\qquad B_1^{(-)}(\rho, \phi, z) = \frac{B_{1\rho}\sin\phi + iB_{1z}}{2}. \tag{8}$$

The co-rotating component $B_1^{(+)}$ is the relevant component for the transmission of RF signals which causes the sample spin transitions. On the other hand, considering the principle of reciprocity, the received RF signals are proportional to $B_1^{(-)*}$ (i.e. the complex conjugate of the counter-rotating RF magnetic field component per current unit), so the signal of the receiving RF coil is simply given by $$S \propto \left|B_1^{(-)}(\rho, \phi, z)\right|. \tag{9}$$

III. Analytical Expression of the Electromagnetic Vector Potential

Here, from Maxwell's equations, we can obtain the analytical expression of the electromagnetic vector potential generated by the current flowing in the RF coil in the configuration described in FIG. 1. We will take into consideration the case in which the sample is a semi-infinite slab ($l_s\to\infty$), $d_m=d_s$=0 cm and assume a negligible thickness for the RF coil. Furthermore, we will consider the dimensions of the metamaterial and the sample, along the directions orthogonal to the axis of symmetry z, much larger than the diameter of the RF coil.

Maxwell's equations admit a monochromatic solution of the shape $\vec{A}$=Re[$A_\phi$(ρ, z)$e^{(-i\omega t)}$], where $A_\phi=A_\phi\hat{\phi}$ is the azimuthal component of the electromagnetic vector potential. Considering the Lorenz gauge (i.e. the electric and magnetic field are given by $E_\phi=i\omega A_\phi$, $B_1=\nabla\times A_\phi$, respectively), the spatial dynamics of the potential vector $A_\phi$(ρ, z) is ruled by the equation $$\nabla^2 A_\phi + \mu^{-1}\nabla_\mu \times (\nabla \times A_\phi) + \epsilon\mu k_0^2 A_\phi = -\mu_0\mu J_\phi \tag{10}$$

where $k_0=\omega/c$, $J_\phi$(ρ, z) is the current density of the RF coil, ε, μ represent the complex dielectric permittivity and the complex magnetic relative permeability, respectively, of the materials considered (c is the vacuum light speed, $\mu_0$ is the vacuum magnetic permeability). Considering the configuration shown in FIG. 1, in which the metamaterial and the sample are assumed to be homogeneous, permittivity and permeability depend only on the coordinate z. The current density distribution of the RF coil is given by $J_\phi=K_\phi(\rho)\delta(z)\hat{\phi}$. By using the Hankel transform we can write $$A_\phi(\rho, z) = \int_0^{+\infty} dk_\rho k_\rho J_1(k_\rho\rho)\tilde{A}_\phi(k_\rho, z)$$

and the potential vector equation becomes:

$$\frac{d}{dz}\left(\mu^{-1}\frac{d\tilde{A}_\phi}{dz}\right) + \epsilon k_z^2\tilde{A}_\phi = -\mu_0\delta(z)\tilde{K}_\phi, \tag{11}$$

wherein $$k_z^2 = k_0^2 - k_\rho^2 \text{ and } \tilde{K}_\phi$$

is the Hankel transform of the RF coil surface current.

Solving the previous equation, we obtain, for the regions occupied by the vacuum (v), the metamaterial (m) and the sample(s):

$$\tilde{A}_\phi = \begin{cases} C_v e^{-ik_z^{(v)} z} & \text{if } z < -l_m, \\ F_m e^{ik_z^{(m)} z} + C_m e^{-ik_z^{(m)} z} & \text{if } -l_m \le z \le 0, \\ F_s e^{ik_z^{(s)} z}, & \text{if } z > 0, \end{cases} \tag{12}$$

where $$k_z^{(v)} = \sqrt{k_0^2 - k_\rho^2},\ k_z^{(m)} = \sqrt{k_0^2 \epsilon_m \mu_m - k_\rho^2},\ k_z^{(s)} = \sqrt{k_0^2 \epsilon_s - k_\rho^2},$$

$$k_\pm^{(v)} = k_z^{(m)} \pm \mu_m k_z^{(v)} \text{ and } k_\pm^{(s)} = k_z^{(m)} \pm \mu_m k_z^{(s)}, \text{ and } C_v, C_m, F_m$$

and $F_s$ are given by $$C_v = \frac{i2\mu_0 \mu_m k_z^{(m)} \tilde{K}_\phi e^{-ik_z^{(v)} l_m}}{k_+^{(v)} k_+^{(s)} e^{-ik_z^{(m)}} l_m - k_-^{(v)} k_-^{(s)} e^{ik_z^{(m)}} l_m}; \tag{13}$$

$$C_m = \frac{i\mu_0 \mu_m k_+^{(v)} \tilde{K}_\phi e^{-ik_z^{(m)} l_m}}{k_+^{(v)} k_+^{(s)} e^{-ik_z^{(m)} l_m} - k_-^{(v)} k_-^{(s)} e^{ik_z^{(m)}} l_m};$$

$$F_m = \frac{i\mu_0 \mu_m k_-^{(v)} \tilde{K}_\phi e^{ik_z^{(m)} l_m}}{k_+^{(v)} k_+^{(s)} e^{-ik_z^{(m)} l_m} - k_-^{(v)} k_-^{(s)} e^{ik_z^{(m)} l_m}};$$

$$F_s = \frac{i\mu_0 \mu_m \tilde{K}_\phi \left[k_-^{(v)} e^{ik_z^{(m)} l_m} + k_+^{(v)} e^{-ik_z^{(m)} l_m}\right]}{k_+^{(v)} k_+^{(s)} e^{-ik_z^{(m)} l_m} - k_-^{(v)} k_-^{(s)} e^{ik_z^{(m)} l_m}};$$

In the example given here, we are interested in the solution in the static limit (i.e., $k_\rho > |\epsilon_m \mu_m| k_0$, $k_\rho >> k_0$ and $k_\rho >> |\epsilon_s| k_0$), to discuss the excitation of magnetic surface plasmons. In this limit, considering a metamaterial with $Re(\mu) = -1$ and low electromagnetic losses (i.e., $\mu_m \simeq -1 + iIm(\mu_m)$ and $Im(\mu_m) << 1$), the preceding relationships are reduced to:

$$C_v \simeq \frac{2\mu_0 \mu_m \tilde{K}_\phi e^{k_\rho l_m}}{k_\rho \left[(1+\mu_m)^2 e^{k_\rho l_m} - 4e^{-k_\rho l_m}\right]}; \tag{14}$$

$$C_m \simeq \frac{\mu_0 \mu_m (1+\mu_m) \tilde{K}_\phi e^{k_\rho l_m}}{k_\rho \left[(1+\mu_m)^2 e^{k_\rho l_m} - 4e^{-k_\rho l_m}\right]};$$

$$F_m \simeq \frac{2\mu_0 \mu_m \tilde{K}_\phi e^{-k_\rho l_m}}{k_\rho \left[(1+\mu_m)^2 e^{k_\rho l_m} - 4e^{-k_\rho l_m}\right]};$$

$$F_s \simeq \frac{\mu_0 \mu_m \tilde{K}_\phi \left[2e^{-k_\rho l_m} + (1+\mu_m) e^{k_\rho l_m}\right]}{k_\rho \left[(1+\mu_m)^2 e^{k_\rho l_m} - 4e^{-k_\rho l_m}\right]}.$$

The expressions obtained highlight two relevant regimes, namely the Pendry regime for $k_\rho << k_1$ and the plasmonic regime for $k_\rho >> k_1$, being $k1 = I_m^{-1} \log[2/Im(\mu_m)]$. In the Pendry regime, when the support of $\tilde{K}_\phi$ is in the region $k_\rho << k_1$, the potential vector within the sample (for z>0) is given by expression (3).

On the contrary, in the plasmonic regime, when the support of Kó is in the region $k_\rho >> k_1$, the potential vector, within the sample, is given by expression (4).

From the comparison of Eq. (3) and the Eq. (4), the resonant nature of the solution in the plasmonic regime is apparent: $|1+\mu_m] = Im(\mu_m)$ and, as $Im(\mu_m)$ decreases, (4) shows a divergent trend.

The data above are provided as examples. It is worth noting that in general, in addition to the spatial arrangement of sample, coil, and metamaterial, it is sufficient to obtain the improvement effect of the invention that the metamaterial is chosen so that it is adapted to develop a surface plasmonic regime, the rest of the values of the parameters being related to optimized configurations of the basic concept of the invention.

Although the examples given refer to magnetic surface plasmons, the technical concept of the invention is also applicable to electric surface plasmons, as described above.

IV. Further Embodiment

According to the invention, an apparatus for the nuclear magnetic resonance analysis of a sample containing at least one nucleus of interest, comprising means of producing a static magnetic field, at least one induction coil C with a maximum transverse dimension $\rho_0$ and tuned in a pass-band around the Larmor frequency defined on the basis of said static magnetic field and at least one nucleus of interest, at least one metamaterial MM, and at least one sample S housing. In the apparatus:

said at least one induction coil C is inserted between said at least one metamaterial MM and said at least one sample S housing;

the distance $d_m$ between said at least one metamaterial MM and said at least one. Induction coil C is in the range from 0 to the maximum transverse dimension of the induction coil; and the metamaterial (MM) is chosen so that it is capable of developing a magnetic or electric surface plasmonic regime;

According to an aspect of the invention, the distance $d_m$ is between 0 and 1/10 of the maximum transverse dimension of the induction coil.

According to a different aspect of the invention, the distance $d_s$ between said at least one induction coil C and said at least one sample S housing is in the range from 0 to the maximum transverse dimension of the induction coil. The distance $d_s$ can be comprised between 0 and 1 cm.

According to an aspect of the invention, said at least one metamaterial MM is a slab with two opposite faces (e.g. lying substantially on said first and second plane), wherein the minimum radius of curvature of at least one of the two opposite sides of the slab is greater than the maximum transverse dimension of the induction coil C.

According to a different aspect of the invention, said at least one metamaterial MM is characterized by a relative magnetic permeability $\mu_m$ such that $Re(\mu_m)$ is in a range about the value −1, said range having a width equal to $2 \cdot Im(\mu_m)$. Preferably: the at least one metamaterial MM has a thickness $I_m$ between the two opposite faces such that $I_m > 1/10$ of the maximum transverse dimension of the induction coil C; the metamaterial MM has a relative magnetic permeability $\mu_m$; the maximum transverse dimension of the coil $\rho_0<2\pi/[l_m^{-1}\log(2/\text{Im}(\mu_m))]$; and the condition that $\text{Re}(\mu_m)$ is in an amplitude range of $2-\text{Im}(\mu_m)$ about the value $-1$ holds.

Said at least one metamaterial MM and said at least one induction coil C can have a development substantially along their respective concentric arcs of circumference. Preferably, the respective concentric arcs of circumference are arcs of 360°. According to another aspect of the invention, said at least one metamaterial MM and/or said at least one induction means C respectively consist of a plurality of metamaterials MM #1, MM #2, MM #3 and/or dielectric materials and induction means C#1, C#2, C#3, positioned in consecutive and separate portions of the respective arcs of circumference.

According to the invention, said at least one metamaterial MM can be characterized by a relative magnetic permeability $\mu_m$ such that $\text{Im}(\mu_m)$ is less than $10^{-1}$, preferably $\text{Im}(\mu_m)$ is less than $10^{-2}$ or $10^{-3}$.

According to an aspect of the invention, said at least one metamaterial MM is chosen so as to present at least two poles tuned to two different Larmor frequencies of at least two corresponding nuclei of interest.

Embodiment with Sphere

I. MLSPS Excitations and Improved Signal-to-Noise Ratio

In the sections above (see also Ref. [3]), the Inventors suggested excited magnetic surface plasmons on the surface of a negative permeability MM slab to increase the SNR values of the magnetic resonance. It is worth considering that surface plasmon polaritons (SPP) and magnetic and/or electrical surface plasmons may exist in geometries other than the slab (e.g. particles with dimensions below the wavelength or empty cavities with different topologies) and can be applied in the magnetic resonance according to the invention. Here, for example, we will discuss the existence of magnetic localized surface plasmons (MLSPs), hosted by a sphere (of radius $\rho_m$}, which in reference to the previous embodiments can be identified as $l_m/2$; or a spheroid with two semi-axes) of MM with negative permeability. Exploiting both the spherical symmetry of the MM device considered and the rotational invariance relative to the axis z of the apparatus shown in FIG. 22, we will focus our attention on monochromatic solutions of the form $\vec{A}=\text{Re}[A_\phi(r,\theta)\,e^{-i\omega t}]$ with angular frequency $\omega$ and where $A_\varphi=A_\phi\hat{\phi}$ is the azimuthal component of the electromagnetic vector potential, $r=\sqrt{\rho^2+z^2}$ and $\theta=\arccos(z/r)$ (see FIG. 22). From Maxwell's equations, we can obtain $$\nabla^2 A_\phi+\mu^{-1}\nabla\mu\times(\nabla\times A_\phi)+\epsilon\mu k_0^2 A_\phi=0, \tag{15}$$

where $\varepsilon$ and $\mu$ are dielectric permittivity and magnetic permeability, respectively, and $k_0=\omega/c$ (c is the speed of radiation in vacuum). We will assume a homogeneous magnetic MM sphere (with radius $\rho_m$) with relative permeability and permittivity $\mu=\mu_m$, $\varepsilon_m=1$ within the sphere and $\mu=1$, $\varepsilon=1$ otherwise. Following Mie's approach, considering the expansion in spherical waves and imposing the connection conditions on the surface of the sphere, it results:

$$A_\phi=A_L\frac{h_L^{(+)}(k_0\rho_m)}{J_L(k_m\rho_m)}j_L(k_m r)P_L^{(1)}(\cos\theta)\quad\text{for } r\le\rho_m, \tag{16}$$

-continued $$A_\phi=A_L h_L^{(+)}(k_0 r)P_L^{(1)}(\cos\theta)\quad\text{for } r>\rho_m,$$

where $A_L$ is a constant, $k_m=\sqrt{\epsilon_m\mu_m}k_0$, L a positive integer (L=1, 2, 3, . . . ), $$P_L^{(1)}$$

is the Legendre polynomial $$P_L^{(m)}$$

with m=1, $j_L$ the spherical Bessel functions and $$h_L^{(+)}$$

the output spherical Hankel functions. These solutions represent localized magnetic waves characterized by the dispersion relation $$\varphi_L^{(1)}(k_m\rho_m)-\mu_m\varphi_L^{(+)}(k_0\rho_m)=0, \tag{17}$$

wherein:

$$\varphi_L^{(+)}(\xi)=\left(d\left[\xi h_L^{(+)}(\xi)\right]/d\xi\right)/h_L^{(+)}(\xi),\ \varphi_L^{(1)}(\xi)=\left(d[\xi j_L(\xi)]/d\xi\right)/j_L(\xi) \tag{18}$$

with $\iota=k_m\rho_m$.

To physically grasp the main features of these solutions, we will consider the static limit $k_0\rightarrow 0$ where $$A_\phi\simeq A_L\left(\frac{r}{\rho_m}\right)^L P_L^{(1)}(\cos\theta)\quad\text{for } r\le\rho_m,$$
$$A_\phi\simeq A_L\left(\frac{\rho_m}{r}\right)^{L+1}P_L^{(1)}(\cos\theta)\quad\text{for } r>\rho_m, \tag{19}$$

and the dispersion relation Eq. (17) becomes $$\rho_m=\frac{1+L}{L}. \tag{20}$$

It is worth noting that for a specific L and, therefore, a specific value of $\mu_m$, the second equation of the Eq. (19) coincides with a term of the standard multipole expansion. Equation (20) is the magnetic counterpart of the condition of the existence of electric localized surface plasmons [1] and makes these resonances exist only for discrete magnetic permeability values. It is worth noting that the excitation of an electromagnetic surface mode generally shows a resonant behavior [1], so an adequate MLSP excitation can produce a significant improvement in the RF electromagnetic field.

The improving effect obtained by using a sphere of MM applies to any value of the sphere radius $\rho_m$ once the $\mu_m$ of the sphere is chosen according to one of the values determined by the equation (20) which is valid in the case of an isolated sphere, or by means of numerical simulations if the presence of the sample S and the RF coil C and/or in the case of the spheroid are to be taken into account.

Preferably, the metamaterial MM with spherical shape has a relative magnetic permeability $\mu_m$ such that $\mathrm{Im}(\mu_m)$ is less than 0.2, even more preferably less than 0.1.

To numerically test the improvement of the electromagnetic field due to the excitation of these surface plasmons located in a magnetic resonance configuration, we will consider the case in which a surface RF coil is located between the MM sphere with negative permeability and the sample, as shown in FIG. 22. Exploiting the rotational invariance of the setup along the z-axis, we evaluate the electromagnetic field and SNR using full-wave 2D simulations in cylindrical coordinates (i.e. in the plane (ρ, z)). In the numerical examples, we will set the frequency ν=127.74 MHz (corresponding to a static magnetic field $|\hat{B}_0|$=3 T), $\rho_m$=8.4 cm, $d_m$=0 mm, $l_m=l_s=3\ \rho_m$, $d_s$=2 mm. The electromagnetic response of the sample is that of muscle tissue ($\epsilon_s$=63.5+i101.2). The RF surface coil has negligible thickness along the z-axis and is described by the azimuth current density $J_\phi(\rho, z)=K_\phi(\rho)\epsilon(z)$ (δ(·) is the Dirac delta function), where $K_\phi(\rho)=K_0$ for $\rho_0-\omega/2<\rho<\rho_0+\omega/2$ and $K_\phi(\rho)=0$ otherwise ($\rho_0=\rho_m/2$=4.2 cm, $\omega=\rho_m/10=\rho_0/5$=8.4 mm and $K_0$ is a constant chosen to obtain a unit current in the coil).

In FIG. 23, we trace $$|B_1^{(-)}|/\mu_0$$

(continuous simple line) and $\mathrm{SNR}^{(n)}$ (continuous gray line with star symbol) at the spatial point ρ=0 mm and z=6 mm (on the z-axis of the RF coil) depending on the real part of the permeability $\mu_m$ of the metamaterial, assuming Im ($\mu_m$) =0.01. For comparison, the permeability values obtained from Eq. (20) are shown in the same figure as vertical black dotted lines. It is worth noting that both $$|B_1^{(-)}|/\mu_0$$

and $\mathrm{SNR}^{(n)}$ snow several peaks (for the latter, highlighted by the star markers in FIG. 23) and each peak is due to the excitation of a specific MLSP. On the other hand, in FIG. 23 you can see that the peaks are shifted relative to the MLSP existence conditions provided by Eq. (20). This can be explained because Eq. (20) neglects the delay effects in Maxwell's equations and applies in the absence of both the sample and the RF surface coil. However, FIG. 23 clearly demonstrates that MLSPs are excited and support a significant improvement of the RF signal $$|B_1^{(-)}|/\mu_0$$

and $\mathrm{SNR}^{(n)}$.

Hereinafter, we focus our attention on the values $\mathrm{Re}(\mu_m)$ highlighted by the star markers in close correspondence with cases in which $\mathrm{Re}(\mu_m)$=−1.39; −1.26; −1.20; −1.16; −1.13. From the comparison of the spatial distribution of the analytical solutions of Eq. (19) with the numerical results, it is apparent that the values $\mathrm{Re}(\mu_m)$ highlighted by the star markers in FIG. 23 correspond to the MLSPs of the Eq. (19) with L=3, 4, 5, 6, 7. Both the resonant behavior of MLSP excitations and their multipolar structure can be exploited to improve the SNR of the magnetic resonance. The first can be improved by reducing MM losses as previously demonstrated for planar configuration (above and [8]). In the case of the MM sphere, by choosing a specific permeability value $\mu_m$, the desired L mode can be excited and then, by increasing the value by L, narrower spatial confinement of the magnetic field and its intensity are obtained compared to the standard case of a surface RF coil in which the field has a dipolar distribution. In FIG. 24, for the sphere with the above geometry and Im(μ)=0.01, we report.

$$|B_1^{(-)}|/\mu_0$$

(panel a) and $\mathrm{SNR}^{(n)}$ (panel b) along the axis z and within the sample (i.e. ρ=0 cm and z>0.2 cm) for the permeability values corresponding to the resonance modes marked by the star symbols in FIG. 23. In FIG. 24 it can be seen that the greater $\mathrm{Re}(\mu_m)$ the greater the values of $$|B_1^{(-)}|/\mu_0$$

anu $\mathrm{SNR}^{(n)}$; for Re ($\mu_m$)=−1.13, the $\mathrm{SNR}^{(n)}$ near the sample interface (z=0.2 cm) is ≃10. FIG. 25, we report the spatial distribution of $\mathrm{SNR}^{(n)}$ without (panel a) and with the sphere MM having the magnetic permeability values as in FIG. 24 (panels b-f), where the dashed isolevel lines correspond to $\mathrm{SNR}^{(n)}$=1. For the considered system, an increase of SNR in the sample (e.g. $\mathrm{SNR}^{(n)}$>1) is obtained within a region with a longitudinal dimension (z-axis) of about 5 cm and a transverse dimension (radius ρ) of about 3.5 cm.

FIG. 25 shows SNR maps (n) in the presence of the MM sphere compared to the SNR map obtained in the standard configuration. It is worth noting that for the various modes, obtained with negative values of $\mu_m$, the value of $\mathrm{SNR}^{(n)}$ increases up to about 10 times with a clear application advantage in the receiving phase of the magnetic resonance experiment. In FIG. 26 *a* similar advantage is observed for the RF excitation field, which implies advantages in RF pulse duration and/or maximum RF amplification power.

Furthermore, FIG. 27 (*a*) shows a maximum centered around the position of the RF coil ($\rho_0$=4.2 cm). In FIG. 27 (*b*)-(*f*) it is observed that the presence of the sphere of MM ($\mathrm{Re}(\mu_m)$=−1.39, −1.26, −1.20, −1.16, −1.13) introduces an asymmetric distribution of the electric field with respect to the plane z=0, concentrating it more inside the sphere MM (values of z<0), near its surface, and shifting the maximum electric field towards smaller radial positions (FIG. 27 (*f*), ρ=2 cm).

II. MLSPS Mimicking by a Dielectric

In the previous section, we studied and characterized MLSP hosted by a spherical MM with negative permeability, suitably inserted in a magnetic resonance configuration. As a matter of fact, the desired magnetic behavior (i.e. a resonant magnetic response at Larmor frequency and a negligible magnetic response at the static limit [3]) is not available in nature. However, a specific magnetic response can be achieved by means of an appropriate composite structure. For example, Freire et al. [6] made a slab of MM having ρ=−1 In the RF field with a periodic ring resonator structure [6]. The use of such repeated structures makes the manufacture of such devices complex. Furthermore, their theoretical description, based on effective medium theories, has imitations due to the intrinsic uneven response of such materials on scales comparable with those of their composite structure.

According to the invention, these limits can be exceeded by demonstrating that the electromagnetic field generated by MLSPs outside the sphere can be mimicked using dielectrics with preferably high relative dielectric constant (typical values of 100-4000 at the frequencies of the previous example are provided in the literature) already available in nature [5]. It is worth noting that several research teams have studied the inclusion of high-ε dielectric materials in a standard magnetic resonance scanner to manipulate the local RF field distribution [5]. Such materials support intense displacement currents capable of modifying the RF field distribution and this effect was taken into account for the impedance adaption, shimming, and focusing the RF field distribution to different static field values (3, 4, 7, 9, 4 T).

In this invention, on the contrary, we will show in detail, by way of example, the equivalence (mimicking), with good approximation, between the external scattering field of a homogeneous dielectric sphere with high permittivity and the electromagnetic field of a specific MLSP produced by a MM sphere of the same radius outside it. We will demonstrate that this dielectric sphere. In turn, produces the significant magnetic resonance SNR enhancement we have already shown for the MM sphere.

For this purpose, referring to FIG. 28, to test the electromagnetic equivalence between the isolated sphere of MM and a dielectric sphere with the same radius $\rho_m$, we compare the localized waves for both configurations. Considering a dielectric sphere in vacuum the electromagnetic response of which is described by the permittivity $\epsilon_d$ and permeability $\mu_d=1$, the condition of existence and the distribution of the electromagnetic vector potential are given by Eq. (17) and Eq. (16) (replacing $\mu_m$ con $\mu_d=1$, $k_m$ con $k_d=\sqrt{\epsilon_d}k^0$), respectively. From Eq. (16), it is apparent that the resonant surface mode of order L (one hosted by the dielectric sphere and the other by the MM sphere with negative permeability) have the same electromagnetic field profile outside the sphere while they differ inside. Equivalence is guaranteed by the condition of existence for both modes on the surface, i.e.

$$\varphi_L^{(1)}(k_m\rho_m) - \mu_m\varphi_L^{(+)}(k_0\rho_m) = 0. \quad (21)$$
$$\varphi_L^{(1)}(k_d\rho_m) - \varphi_L^{(+)}(k_0\rho_m) = 0.$$

Consequently, the equivalent dielectric permittivity $\epsilon_d$ may be evaluated by solving the complex transcendent equation:

$$\varphi_L^{(1)}(k_m\rho_m) - \mu_m\varphi_L^{(1)}(k_d\rho_m) = 0. \quad (22)$$

A similar approach was initially considered by Devilez et al. to mimic surface electric plasmons hosted by a spherical metal particle by means of a spherical dielectric particle [4]. Eq. (21) can only be met exactly for real permeability and permittivity values, i.e. for loss-free materials. For a low-loss magnetic material (the permeability value of which satisfies by first approximation the first of the Eq. (21)), we can still determine an equivalent complex permittivity which satisfies Eq. (22) and the accuracy of the electromagnetic equivalence can be verified by means of a numerical simulation taking into account all the implementation parameters.

The value of $\epsilon_d$ determined by equation (22), with the parameter $k_0$ implicitly contained in the equation by means of the definition of $k_m$ and $k_d$, depends on the chosen working frequency.

Therefore, the resulting value of $\epsilon_d$ will depend on the selected value of $\mu_m$ of the MM sphere whose electromagnetic field one wishes to mimic, the radius of the sphere (or the radii for the spheroid) and the working frequency.

In the presence of magnetic metamaterial losses and/or in the presence of sample S and (RF) coil C the solution of equation (22) no longer guarantees the exact correspondence between the electromagnetic field generated outside the magnetic MM sphere and outside the uHDC sphere. In this case, the verification of the accuracy of the approximation between the electromagnetic fields must be performed by numerical methods, as shown in the example of FIG. 33(*a*).

If the accuracy of the solution found by means of the equation (22) is deemed not satisfactory, it can be improved by numerical methods by determining complex values of $\epsilon_d$ that minimize the differences between the electromagnetic fields of the MM sphere and the uHDC sphere within the sample S.

For the frequencies of interest, we consider all those of use in MRI/NMR/EPR ranging from 1 kHz to 300 GHz. In the MRI scope, we expect the range of values of the radius of the sphere of MM or the equivalent sphere of uHDC that have a practical utility to be comprised between 0 and 20 cm. In the MRI scope for frequencies close to 400 MHz, the preferred values of $\epsilon_d$ of the uHDC sphere (spheroid) would be $Re(\epsilon_d)$ about 8000, $Im(\epsilon_d)$ less than 300 (i.e. tan δ less then 0.038).

By way of example, setting L=5 and numerically searching for solutions of Eq. (22) with $\rho_m$=8.4 cm, ν=127.74 MHz (3 T) and $\mu_m$=−1.20+i 0.01, it is obtained that Eq. (22) is satisfied for $\epsilon_d$=1324+i1.65. This result suggests that the MLSP considered with $\mu_m$=−1.2+i0.01 (the permeability value ensures an SNR improvement as shown in FIG. 33 and almost satisfies the first Eq. (20)) is reproduced by the electromagnetic field outside the dielectric sphere with the same radius and $\epsilon_d$=1324+i1.65. Of practical relevance is what happens when the sample and the RF coil are in the immediate vicinity of the sphere.

FIG. 30 shows the mapping in the (ρ, z) plane of the SAR at 127.74 MHz ($B_0$=3 T) with the same parameters as FIG. 29 without (a) and with (b) the uHDC sphere for tan δ=0.04 and $\rho_m$=8.82 cm. Similarly, FIG. 31 shows the mapping in the plane (ρ, z) of the effective transmission field $$|B_{1,eff}^{(+)}| \; (\phi = \pi/2)$$

at 127.74 MHz ($B_0$=3 T) with the same parameters as FIG. 29 without (a) and with (b) the uHDC sphere for tan δ=0.04 and $\rho_m$=8.82 cm.

FIG. 32 shows results for a uHDC sphere with Re (Ed)=3300 and radii $\rho_m$=4.08, 7.49, 10.64 cm supporting resonances L=1, 3, 5, respectively, at the Larmor frequency of 63.87 MHz ($B_0$=1.5 T). Again in this case, a gain of $SNR^{(n)}$ (estimated at z=2 mm, ρ=0 mm) is also observed in this case, but at a narrower range of values of the loss tangent tan δ (gray area of FIG. 32 *b*).

In FIG. 33 we compare the configuration of FIG. 22 (magnetic MM sphere with $\mu_m$=−1.20+i0.01) and that of FIG. 28 (uHDC sphere with $\epsilon_d$=1324+i1.65) both corresponding to the resonant mode L=5. In FIGS. 33 (*a*) and 33 (*b*), within the sample (z>0.2 cm, φ=π/2), we compare $$|B_1^{(-)}|/\mu_0$$

and SNR$^{(N)}$ along the z-axis to different values of the radial coordinate; while, in FIGS. 33 (*c*) and 33 (*d*), we will compare the maps of SNR$^{(n)}$ in the plane (ρ, z) (for φ=π/2). From FIG. 33, it is apparent that, in a realistic MRI configuration, the equivalence is valid to a good extent because the deviation is closely located on the z axis and near the interface between the sample and the air. Indeed, we note that the maximum deviation for $$|B_1^{(-)}|/\mu_0$$

is about 24% at z=2 mm and ρ=0 mm, while the correspondence is more and more accurate in the other regions.

It is worth noting that the mimicking is more accurate when losses are lower. In the limit of the absence of losses, the shape of the field is dominated by the divergent displacement (magnetization) currents within the dielectric (magnetic) sphere, which become very large compared to those of the coil and of the currents in the sample, and consequently, we approach the condition in which the spheres are isolated and Eq. (20) can be fully satisfied.

III. MIE Resonances with Very High Permittivity Ceramics

To verify the feasibility of the suggested configuration in which the magnetic sphere MM is replaced by the dielectric sphere, we will study the Mie resonances and their effects on magnetic resonance applications by assuming the properties of dielectric materials already used in the context of nuclear magnetic resonance. We will not discuss the quality of the mimicking approach, related to material losses, sample, and RF coil presence hereinafter. Here, we will focus our analysis on the improvement in MRI performance achievable with the inclusion of a dielectric sphere when its radius is chosen to satisfy the second of Eq. (20) at the desired Larmor frequency.

A large class of ferroelectric materials has low losses and has a very high real part of dielectric permittivity, with values which can be customized using different physical-chemical factors [5] (e.g. applied static electric field, temperature, chemical composition, doping and mixing with other dielectrics). However, the desired dielectric permittivity value may not be easily obtained at the operating frequency. On the other hand, it is worth noting that MLSP resonances are also highly dependent on material geometry. Indeed, by assigning a specific value of the dielectric constant, it is possible to satisfy the condition of existence by finely adjusting the radius of the sphere $\rho_m$. As mentioned above, dielectric ceramics have been used to improve the different aspects of the magnetic resonance. High dielectric permittivity values $\epsilon_d$ were made from high-concentration aqueous ceramic mixtures (Re ($\epsilon_d$)=475 at 7 T) or sintered ceramic beads (Re ($\epsilon_d$)=515 at 3 T). Rupprecht et al. [5] demonstrated improved RF coil sensitivity using materials with an ultra-high dielectric constant (uHOC) at 1.5 T and 3 T. In particular, they experimentally studied lead zirconate titanate-based ceramics (PZT) where Re ($\epsilon_d$)=1200 or Re ($\epsilon_d$)=3300 at 3 T and 1.5 T, respectively. Recently, to increase the SNR of the magnetic resonance, the use of ceramic materials was suggested, based on $BaTiO_3$ with $ZrO_2$ and $CeO_2$ as additives, leading to uHOC with Re ($\epsilon_d$)=4500 at 1.5 T. Here we will study the performance in magnetic resonance considering the two permittivity values reported by Rupprecht et al. [5].

In the first example, we will fix the real part of the sphere permittivity to the value of Re ($\epsilon_d$)=1200 for the working frequency 127.74 MHz ($|\overline{B}_0|$=3 T) and, to study the effect of dielectric losses on magnetic resonance performance, we will vary the imaginary part of the permittivity. For this purpose, full-wave numerical simulations were performed, using axial symmetry again, choosing the same coil and the example parameters in FIG. 33 (i.e., $d_m$=0 mm, $\rho_s$=$l_s$=25.2 cm, $d_s$=2 mm, $\rho_0$=4.2 cm, w=8.4 mm e $\varepsilon_s$=63.5+i101.2), except for the radius of the sphere $\rho_m$ adjusted to select three different resonant modes (i.e. L=1, 3, 5).

An additional example is shown in the results of FIG. 29, wherein we have a sphere of ultra-high dielectric constant (uHOC) with Re ($\epsilon_d$)=1200 and radii $\rho_m$=3.38, 6.21, 8.82 cm supporting resonances L=1, 3, 5, respectively, at the Larmor frequency of 127.74 MHz ($B_0$=3 T) and in the presence of RF coil and sample. Also in this case, a gain of SNR$^{(n)}$ is observed (estimated at point z=2 mm, ρ=0 mm) at a wide range of values of the loss tangent tan δ of the uHOC sphere (gray area of FIG. 29 *b*).

In FIG. 29, we report $$\left(|\vec{B}_0| = 1.5\ T\right).$$

and SNR$^{(n)}$ at the spatial point z=2 mm, ρ=0 mm, as a function of the dielectric losses parameterized by tan δ=Im ($\varepsilon_d$)/Re($\varepsilon_d$), for $\rho_m$=3.38 cm, $\rho_m$=6.21 cm, $\rho_m$=8.82 cm (dielectric sphere radii supporting MLSP with L=1, 3, 5, respectively). The range of losses considered (5–$10^{-3}$<tan δ<0.17) has been selected in accordance with the literature [5] for the frequencies corresponding to magnetic resonance imaging at fields of 3 T or less. From FIG. 29 (*a*), the RF signal enhancement produced by the uHDC sphere is apparent. Furthermore, in FIG. 29 (*b*), we can observe an increase in SNR (SNR$^{(n)}$>1) in the wide range 0.005<tan δ<0.167 (gray region). In case tan δ=0.04, i.e. the value of the MRI dielectric pad tested in [5], we observe SNR$^{(n)}$=1.6, 1.5, 1.3 for $\rho_m$=3.38, 6.21, 8.82 cm, respectively. From the results shown in FIG. 29 (*b*), using a material with tan δ=5·$10^{-3}$, the SNR$^{(n)}$ would be 2.7 ($\rho_m$=3.38 cm, L=1), 3,3 ($\rho_m$=6.21 cm, L=3) and 3.1 ($\rho_m$=8.82 cm, L=5), respectively.

In a second series of full-wave simulations, we assume the real part of the permittivity of the uHDC sphere Re ($\epsilon_d$) =3300 and the working frequency ν=63.87 MHz $$|B_1^{(-)}|/\mu_0$$

We will consider the same coil and geometric parameters as in FIG. 29, choosing $\epsilon_s$=72.3+i193.7 corresponding to the dielectric constant of muscle tissue at 1.5 T. The MLSP with L=1, 3, 5 correspond to $\rho_m$=4.08, 7.49, 10.64 cm, respectively. FIG. 32 shows $$|B_1^{(-)}|/\mu_0$$

(a) and SNR$^{(N)}$ (b) at the spatial point z=2 mm, ρ=0 mm as a function of tan & for the chosen modes. FIG. 32 (*a*) shows an enhancement of the receiving RF signal $$|B_1^{(-)}|/\mu_0$$

throughout the range $5\cdot10^{-3}<\tan\delta<0.09$. In FIG. 32 (*b*), we note that $SNR^{(n)}>1$ (region in gray) for $\tan\delta<0.022$. For $\tan\delta=0.005$, we get an $SNR^{(n)}$ of about 1.4, 1.6, 1.5 for $\rho_m$=4.08, 7.49, 10.64 cm, respectively. However, for $\tan\delta=0.05$, as in the material used previously, we have $SNR^{(n)}$ =0.74, 0.69, 0.62 for ρm=4.08, 7.49, 10.64 cm, respectively. As in many photonic sub-wavelength devices, tan δ is a crucial parameter because high losses can drastically reduce or even eliminate the electromagnetic resonance of the dielectric.

For the sake of completeness, we will evaluate the SAR and transmission efficiency within the sample. The local specific absorption rate is given by $SAR=\sigma|E|^2/(2\rho_V)$, where E is the complex electric field asmplitude, $\sigma=\omega\epsilon_0 \mathrm{Im}(\epsilon_s)$ and $\rho_V$ are the electrical conductivity and mass density of the sample, respectively [5]. In FIG. 30, we compare the SAR for the unit current without (a) and with (b) the 3 T uHDC sphere using the same parameters as FIG. 29 with tan δ=0.04 and $\rho_v$=3490 kg/m$^3$ [5]. Clearly, the maximum SAR (e.g. $SAR_{max}$=max(SAR)) is a critical parameter because it limits the maximum power to be applied to the drive RF coil. Here, it is very interesting to note that the $SAR_{max}$ and the SAR averaged over the whole volume (e.g. $SAR_\alpha=\int_{sample}dr^3 SAR/V$, where V is the whole sample volume) are both reduced in presence of the dielectric sphere. More precisely, $SAR_{max}$ ($SAR_\alpha$) decreases from 21.5 W/kg ($3.5\cdot10^{-2}$ W/kg) to 18.6 W/kg ($2.1\cdot10^{-2}$ W/kg) without and with the uHDC sphere, respectively. The reduction of $SAR_{max}$ by approximately 14% (SAR, reduced by 40%) in the presence of the uHDC sphere is an important advantage for 3 T magnetic resonance and could be useful for higher static field applications (7; 9.4 T).

In FIG. 31, we compare the maps of $$|B_{1,eff}^{(+)}|,$$

defined as the ratio of the absolute value of the field $$B_1^{(+)}$$

and the square root of $SAR_{max}$, without (a) and with (b) the uHDC sphere under the same conditions as in FIG. 30. Despite the fact that the geometrical parameters of the considered configuration have not been completely optimized, from FIG. 31 both an improvement in RF efficiency and a significant focus of the magnetic field in the region near the axis of the RF coil, i.e. near the central volume of the sample under study, are apparent. Finally, we can observe, in the presence of the uHDC sphere, that the SAR is concentrated at about ρ=4 cm, i.e. close to the RF coil. As a result, by placing a relatively small sample close to the coil axis, our configuration makes it possible to improve the magnetic resonance performance by reducing SAR in the region of interest.

FIG. 34 shows the layout of an MRI configuration with geometry B according to an aspect of the invention, with the sphere (of magnetic MM or UHDC) positioned between a standard surface RF coil and the cylindrical sample.

FIG. 35 shows the maps $$|B_1^{(-)}|/\mu_0$$

within the cylindrical sample ($d_m$=0 mm; z≥2 mm) in the presence of: magnetic MM sphere ($\mu_m$=−1.2+i0.02) with (a) geometry A ($d_s$=2 mm) or (b) geometry B ($d_s=\rho_m$+2 mm); uHDC sphere ($\varepsilon_d$=1324+i1.65) with (c) geometry A ($d_s$=2 mm) or (d) geometry B ($d_s=\rho_m$+2 mm), FIG. 35 shows, for a more immediate comparison, the profile (ρ=0 mm) of $$|B_1^{(-)}|/\mu_0$$

for geometry A and B in the presence of the MM sphere (e) or of the uHDC sphere (f).

FIG. 36 shows the graphs as in FIG. 35 for the |E| field (per current unit).

FIG. 37 shows the graphs as in FIG. 35 for the SAR (for the unit current).

FIG. 38, assuming a working frequency of 127.74 MHz ($B_0$=3 T), shows: in (a) the profile of $$|B_1^{(-)}|/\mu_0$$

along the z-axis ($d_m$=0 mm) for the uHDC sphere (a=1200+i48) with geometry A ($d_x$=2 mm, solid line) and geometry B ($d_s=\mu_m$+2 mm, dashed line); in (b) the specific SAR absorption rate at the plane (ρ, z) without uHDC; in (c) the SAR in the presence of the uHDC sphere ($\varepsilon_d$=1200+i48) with geometry A ($d_s$=2 mm); in (d) the SAR in the presence of the uHDC sphere ($\varepsilon_d$=1200+i48) with geometry B ($d_s=\rho_m$+2 mm).

FIG. 35 shows the maps of $$|B_1^{(-)}|/\mu_0$$

in the plane (ρ, z) for the MM sphere and the uHDC sphere. A reasonable similarity of spatial distribution between geometric configurations A (FIG. 1 *a*) and B (FIG. 34) is observed, with a slight decrease in amplitude in the case of the uHDC sphere in geometry B. Similar results are observed for the field maps |E| shown in FIG. 36 and SAR shown in FIG. 37. The results shown in FIG. 35-37 allow us to conclude that the uHDC sphere is a valid alternative to the use of the MM sphere, with a considerable practical simplification.

Although the case in which the induction coil is adjacent to or away from one end of the metamaterial or dielectric along dimension z was always treated above, it is also possible for the coil to surround at least part of the metamaterial or dielectric. In other words, two parallel planes can be defined between which the metamaterial or dielectric extends, the planes being parallel and perpendicular to the z-direction, in such a case, the distance of the coil from either plane can be both positive and negative. In case of negative distance, the plane of the coil crosses somewhere through the metamaterial or dielectric, and obviously, the coil must be wide enough to surround it on the xy plane, so that there is no interpenetration between the two elements.

It is also possible to express this configuration by saying that the distance module $d_m$ is comprised in the range specified below. The possibility of using a positive or negative distance (coil between the two planes above or outside the metamaterial or dielectric) depends on the geometry of the metamaterial or dielectric as well as on the plasmonic or dielectric resonance regime to be excited. A positive distance is, however, generally preferred.

Even more in general, the various configurations of the apparatus according to the invention, in terms of the aforesaid distances, can be included in the relation $d_s+d_m \geq 0$. A particular case of the invention is when both $d_s$ and $d_m$ are positive.

Advantages of the Invention

According to the invention, a new use of a magnetic metamaterial slab is provided to increase the performance of an RF coil in a magnetic resonance device useful for both spectroscopy (NMR) and imaging (MRI) applications. The approach of the invention is based on magnetic plasmonic resonances present on at least one surface of a metamaterial slab with Re $(\mu_m)=-1$ which are responsible for a strong increase of the RF magnetic field within a sample suited for magnetic resonance imaging. A further advantage of the suggested configuration is the positioning of the metamaterial slab, i.e., outside the RF coil and sample assembly, in a region in which free space is usually available.

In this respect, the present invention has the potential to be applied in most current situations of use with minimal additional requirements compared to available configurations. The results are based on an approximate description of the current density in the RF coil and do not assume losses in the RF coil itself. Furthermore, the described mode can be implemented also if one desires to detect the signal coming from two or more NMR or MRI active nuclear species present in the sample, i.e. In multi-nuclear mode, using a metamaterial able to support at least two distinct plasmonic resonances the resonance frequency of which coincides, or is close to, the one corresponding to the known Larmor frequencies (metamaterial chosen to present at least two poles tuned to two different Larmor frequencies of at least two corresponding nuclei of interest). A two-dimensional metamaterial configuration has been described in the literature which can be used to improve the detection of the proton $^1H$ and phosphorus $^{31}P$ nuclear signal. Such metamaterial supports Fabry-Perot resonances by means of a given number of metal strips appropriately separated from each other and arranged on a plane. Such device behaves like a set of electric dipoles, suited for the low frequencies corresponding to the signal of $^{31}P$ and a second set of magnetic dipoles necessary for the detection of the signal $^1H$.

Finally, we can note that the invention could also be extended to the context of electronic paramagnetic resonance (EPR).

Furthermore, to use the prior art with dielectrics according to the invention, the values of the real and Imaginary part of the electrical permittivity of the dielectric material should be appropriately selectable to satisfy the conditions of electromagnetic equivalence relative to the magnetic metamaterial of identical or similar geometry.

It is interesting to observe the ability of the invention to replace a magnetic and/or electrical metamaterial with an equivalent dielectric material, because the practical making of the metamaterial may present limitations due to the physical dimensions of the constituent unitary cells (usually small inductive/capacitive resonant circuits of a circular shape, see [2]), which makes it difficult to achieve the spatial homogeneity condition.

More generally, the following beneficial effects of the invention are listed in a non-exhaustive manner 1. The metamaterial slab can support surface plasmonic resonances at the frequency of use of magnetic resonance (Larmor frequency) on at least one of its component surfaces. Such plasmonic resonances can be appropriately excited by an RF coil, tuned to the Larmor frequency of the magnetic resonance apparatus. Plasmonic resonances, characterized by the presence of intense concentrated currents near at least one of the surfaces of the metamaterial slab, have the effect of amplifying the intensity of the RF magnetic field in a specific region of the sample under examination, which is placed at a given distance from the surface of the metamaterial slab.
2. Plasmonic resonances useful for the purposes of the present invention can be located on the surface of structures other than the slab, such as a spherical shape [1], a semi-spherical shape, a cylindrical shape, an ellipsoidal shape, a toroidal shape, and even structures with an irregular surface [1, 2].
3. The RF coil can also be used to detect the signal of the sample under examination which, in a similar manner as described in the preceding point, is amplified by the plasmonic resonances of the metamaterial.
4. The circular RF coil used in the resonance apparatus is described in FIG. 1, may be replaced by a square, rectangular, or triangular coil, or any other shape capable of exciting plasmonic resonances on at least one surface of the metamaterial.
5. The geometry and composition of the metamaterial can be appropriately chosen to generate a given spatial distribution of the RF field amplitude in the inner volume of the sample under examination.
6. The metamaterial is preferably, but not necessarily, positioned outside the RF excitation/detection coil facing the sample itself, to maximize the amplification effect.
7. The properties of the metamaterial (used for making the slab or other useful structures) can be adjusted to assume the desired value at the working frequency (Larmor frequency) for the specific application of magnetic resonance, e.g. the frequency of about 64 MHz could be chosen to detect the hydrogen signal ($^1H$) present in the tissues when these are in the presence of a static magnetic field of 1.5 T.
8. The functionality of the metamaterial can only be used during the excitation operating phase, or only during both the excitation and signal detection phases.
9. The electrical and/or magnetic parameters of the metamaterial can be modified, even in dynamic mode, within a given range by means of an appropriate electrical and/or mechanical control to modulate the effects on the signal in a specific spatial position.
10. The geometric arrangement of the metamaterial relative to the RF coil and the sample can be modified within a given range of values by means of a mechanical control to modulate the effects on the signal also in dynamic mode.
11. The metamaterial can support more than one mode of surface plasmonic resonance (multi-nuclear mode), each corresponding to a distinct frequency able to excite and/or detect, either simultaneously or consecutively, the signal of at least two nuclear species useful for magnetic resonance, and by way of example we could consider hydrogen ($^1H$) and sodium ($^{23}Na$) of biological tissues exposed to the same static magnetic field.

12. The element comprising the metamaterial and its excitation/detection RF coil can be structured in a volume configuration (e.g. of the birdcage, or saddle, or TEM type), which surrounds and encloses all or part of the test sample.
13. The element which comprises the metamaterial and the respective excitation/detection coil can be replicated a given number of times (N), and be arranged near the sample to ensure multi-channel operation, with sequential or parallel acquisition both for single nucleus (e.g. $^1H$) and multi-nuclear (e.g. $^1H$ and $^{23}Na$).
14. The properties of the MM can be adjusted to allow paramagnetic electronic resonance (ESR, EPR) applications in a frequency range from radio frequencies to microwaves.
15. In the case of the magnetic MM sphere, there is an infinite number of resonance modes which can be excited and each of which corresponds to its own spatial trend of the transmission and/or reception electromagnetic field and SNR, which can be useful for specific applications, so the expert user can select them according to needs.
16. To use a specific magnetic resonance mode to the desired Larmor frequency, the geometry (sphere radius) and the value of pw of the sphere (negative) must be adapted. For this purpose, analytical and/or numerical electromagnetic simulation methods may be used to optimize such parameters.
17. The efficiency maps of the transmission RF magnetic field with the magnetic MM sphere show that there is an improvement in RF efficiency and also a significant focus of the magnetic field in the region near the axis of the RF coil, i.e. near the central volume of the sample under study.
18. Having demonstrated the electromagnetic equivalence between the magnetic MM sphere and a dielectric sphere (uHDC) of the same radius and with selected permittivity value, it follows that the preceding advantages in terms of excitation and/or detection field and/or SAR apply to the case of the dielectric sphere, this advantage being particularly important for 3 T magnetic resonance and useful applications in higher static fields can be expected (7; 9.4 T).
19. The use of the uHDC sphere simplifies the practical implementation of the detection system, as it is not necessary to build unit cells with conductive and insulated elements, with considerable cost savings.
20. A further advantage of the uHDC sphere is the absence of static magnetic field disturbance, which allows the acquisition of MRI data without the introduction of artifacts.
21. The suggested uHDC device makes it possible to avoid complex manufacturing procedures and the inhomogeneous response of the electromagnetic field present in a magnetic composite MM when the size of the constituent inclusions of the MM becomes comparable to the radius of the sphere or with the size of the plasmonic resonance modes because the intrinsic inhomogeneity of the MM can dramatically modify or even eliminate the presence of such modes, the existence of which is based on the effective medium theory. With the use of uHDC, this fundamental limit is completely overcome because the homogeneous macroscopic dielectrics do not present spatial inhomogeneity.

LITERATURE

[1] A. V. Zayats, I. I. Smolyaninov, A. A. Maradudin, Nano-optics of surface plasmon polaritons, Physics Reports, 408, 131-134 (2005).
[2] N. Engheta and R. W. Ziolkowski, Engineering, physics, and applications of Metamaterials. John Wiley & Sons& IEEE Press (2006).
[3] J. B. Pendry, L Martin-Moreno, F. J. Garcia-Vidal, "Mimicking Surface Plasmons with Structured Surfaces", Science. 305 (5685): 847-848 (2004).
[4] W. X. Tang, H. C. Zhang, H. F. Ma, W. X. Jiang, T. J. Cui. Concept, Theory, Design, and Applications of Spoof Surface Plasmon Polaritons at Microwave Frequencies, Adv. Optical Mater. 1800421, 2018.
[5] S. Rupprecht, C. T. Sica, W. Chen, M. T. Uanagan, and Q. X. Yang. Improvements of transmit efficiency and receive sensitivity with ultrahigh dielectric constant (uHOC) ceramics at 1.5 T and 3 T, Magn. Reson. Med. 79, 2842(2018).
[6] M. J. Freire, L. Jelinek, R. Marques, M. Lapine, On the applications of $\mu_r=-1$ metamaterial lenses for magnetic resonance imaging. J. Magn. Reson. 203, 81(2010).
[7] A. Devilez, X. Zambrana-Puyalto, B. Stout, and N. Bonod, Mimicking localized surface plasmons with dielectric particles, Phys. Rev. B 92, 241412(R)(2015).
[8] C. Rizza, M. Fantasia, E. Palange, M. Alecci, and A. Galante, Harnessing Surface Plasmons for Magnetic Resonance imaging Applications, Phys. Rev. Appl. 12, 044023 (2019).

Hereto, we have described the preferred embodiments and suggested some variants of the present invention, but it is understood that a person skilled in the art can make modifications and changes without departing from the respective scope of protection, as defined by the appended claims. $SNR^{(m)}/SNR^{(V)}$) signal-to-noise ratio (SNR), where $SNR^{(m)}$ $SNR^{(V)}$ are calculated in presence and absence of the metamaterial, respectively.

FIG. 2 shows the graph of $$|B_1^{(-)}|/\mu_0$$

(curves) and $SNR^{(n)}$ (curves with square symbols) as a function of: (a) $Re(\mu_m)$ (assuming $Im(\mu_m)=0.01$); (b) $Im(\mu_m)$ (assuming $Re(\mu_m)=-1$). In both cases, $$|B_1^{(-)}|/\mu_0$$

and $SNR^{(n)}$ are calculated at $\rho=2$ cm;

$$\phi=\frac{\pi}{2};$$

z=1 mm; having assumed $d_m=d_s=0$ mm.

FIG. 3 shows a graph as in FIG. 2 where $$|B_1^{(-)}|/\mu_0$$

and $SNR^{(n)}$ are calculated in the point: ρ=2 cm;

$$\phi = \frac{\pi}{2};$$

z=3 mm; for $d_m$=0 mm; $d_s$=2 mm.

FIG. 4 shows a graph as in FIG. 2 where $$|B_1^{(-)}|/\mu_0$$

and $SNR^{(n)}$ are calculated in the point: ρ=2 cm;

$$\phi = \frac{\pi}{2};$$

z=3 mm; for $d_m$=2 mm; $d_s$=2 mm.

FIG. 5 shows a two-dimensional map in the plane (ρ, z) of $SNR^{(n)}$ in the presence of the metamaterial slab assuming $Re(\mu_m)=-1$, $d_m=d_s=0$ mm, $$\phi = \frac{\pi}{2},$$

$l_m$=5.7 cm, $l_s$=20 cm with: (a) $Im(\mu_m)=0.1$; (b) $Im(\mu_m)=0.01$; (c) $Im(\mu_m)=0.001$; in panel (d) same parameters as (c) but with $d_s$=4 mm; the white dotted curves correspond to level SNR(C)=1.

FIG. 6 shows a two-dimensional map in the plane (ρ, z) of $$\log_{10}|B_1^{(+,n)}|, \text{ with } |B_1^{(+,n)}| = |B_1^{(+,MM)}|/|B_1^{(+,V)}|, \text{ where } |B_1^{(+,MM)}|$$

is the excitation RF magnetic field calculated in presence of the metamaterial, $$|B_1^{(+,V)}|$$

is the maximum of the absolute value of the same quantity, within the sample, in the configuration without the metamaterial; in the figure, it is assumed $d_m=d_s=0$ mm, $$\phi = \frac{\pi}{2},$$

$l_m$32 5.7 cm, is =20 cm and with: (a) $\mu_m=1$, (i.e. vacuum instead of metamaterial); (b) $\mu_m=-1+i0.1$; (c) $\mu_m=-1+i0.01$; (d) $\mu_m=-1+i\ 0.001$. The white dotted curves correspond to level $$\log_{10}|B_1^{(+,n)}| = 0.$$

The invention claimed is:

1. An apparatus for magnetic resonance analysis of nuclear and/or electronic spin of a sample containing at least one nucleus and/or one electronic spin of interest, comprising means for producing a static magnetic field and the following elements positioned along an axis (z):

induction means at a predefined position along the axis (z) and having a maximum transverse dimension $\rho_0>0$ perpendicularly to said axis (z), said induction means being tuned around a Larmor frequency defined on the basis of said static magnetic field and of the at least one nucleus and/or electronic spin of interest;

at least one sample housing; and at least one metamaterial or dielectric material that is an ultra-high dielectric constant (uHDC) material, having a dimension $l_m>0$ along said axis (z) between a first plane and a second plane perpendicular to the axis (z), the first plane being further from said at least one sample housing and the second plane being closer to said at least one sample housing, along the axis (z); wherein:

the at least one sample housing is bounded along the axis (z) by a tangent plane perpendicular to the axis (z), the tangent plane being closest to the at least one metamaterial or dielectric material;

a real value quantity $d_m$ is defined which represents a difference between a position along the axis (z) of the induction means and the position along the axis (z) of the first plane of the at least one metamaterial or dielectric material, and a real value quantity $d_s$ which represents the difference between the position along the axis (z) of the tangent plane and the position along the axis (z) of the induction means;

and wherein:

the at least one metamaterial is configured to develop a magnetic surface plasmonic regime, the at least one metamaterial has a relative magnetic permeability $\mu_m$ with negative real part, and the at least one metamaterial:

is a metamaterial slab with $Re(\mu_m)=-1$ which supports surface plasmonic excitations, in the situation where $\tilde{K}_\phi(k_\rho)$, which is the Hankel transform of the induction means' density current $K_\phi(\rho)$, is not null in the region of $k_\rho>>k_1$, being $$k_1 = l_m^{-1}\log[2/\mathrm{Im}(\mu_m)]$$

defined by the thickness of the metamaterial slab ($l_m$) and its losses ($Im(\mu_m)$), where $k_\rho$ is the conjugate variable of ρ, used in cylindrical spatial coordinates (□, ϕ, z) to define the Hankel transform of the azimuthal component of the vector potential $$\left(A_\phi(\rho, z) = \int_0^{+\infty} dk_\rho k_\rho J_1(k_\rho\rho)\tilde{A}_\phi(k_\rho, z)\right),$$

wherein $J_1$ is a Bessel function of the first kind of order one and $\tilde{A}_\phi$ is the Hankel transform of the Vector potential in space $k_\rho$, z, and wherein $\mu_m$ is such that $Im(\mu_m)$ is less than 0.1, or has substantially spherical or spheroidal shape and $Re(\mu_m)$ is negative and approximate to the first order by $$\mu_m = -\frac{1+L}{L}$$

wherein L is a positive integer which identifies a magnetic plasmonic mode;

or the at least one dielectric material is configured to develop a dielectric resonance regime, the at least one dielectric material has a relative dielectric permittivity $\varepsilon_d$ with positive real and imaginary parts, and the at least one dielectric material with magnetic permeability $\mu_d=1$ has substantially spherical or spheroidal shape and satisfies the equation:

$$\varphi_L^{(1)}(k_m\rho_m) - \mu_m\varphi_L^{(1)}(k_d\rho_m) = 0.$$

wherein $$\varphi_L^{(1)}(\xi) = \left(d[\xi j_L(\xi)]/d\xi\right)/j_L(\xi),$$

$j_L$ are spherical Bessel functions, $\rho_m$ is the radius of the sphere, $k_m=\sqrt{\epsilon_m\mu_m}k_0$ and $k_d=\sqrt{\epsilon_d}k_0$ with $k_0=\omega/c$ where $\omega=2\pi\nu$ and $\nu$ is the working Larmor frequency of the induction means, with $\xi=k_m\rho_m$ in the first term on the left-hand side and $\xi=k_d\rho_m$ in the second term on the left-hand side of the equation, and wherein $\mu_m$ is the relative magnetic permeability and $\varepsilon_m$ the dielectric permittivity of an equivalent sphere of said at least one metamaterial resonating at the Larmor frequency;

said induction means face said first or said second plane.

2. The apparatus of claim 1, wherein the real value quantity $d_m$ ranges from 0 to the maximum traverse dimension $\rho_0$ of said induction means.

3. The apparatus of claim 1, wherein the real value quantity $d_m$ is comprised between 0 and 1/10 of the maximum traverse dimension $\rho_0$ of said induction means.

4. The apparatus of claim 1, wherein the real value quantity $d_s$ ranges from 0 to the maximum traverse dimension $\rho_0$ of said induction means.

5. The apparatus of claim 4, wherein the real value quantity $d_s$ is comprised between 0 and 1 cm.

6. The apparatus of claim 1, wherein said at least one metamaterial or dielectric material consists of a flat slab with two opposite faces, lying on said first and second planes, wherein a minimum radius of curvature of at least one of the two opposite faces of the flat slab is greater than the maximum transverse dimension $\rho_0$ of the induction means.

7. The apparatus of claim 6, wherein said at least one metamaterial has a relative magnetic permeability $\mu_m$ such that $\mathrm{Re}(\mu_m)$ is in a range of about −1, said range having a width equal to $2\cdot\mathrm{Im}(\mu_m)$.

8. The apparatus of claim 6, wherein:

the at least one metamaterial has a thickness $l_m$ between the two opposite faces such that $l_m>1/10$ of the maximum transverse dimension $\rho_0$ of the induction means; and the maximum transverse dimension of the induction means is $2\rho_0<4\pi/[l_m^{-1}\log(2/\mathrm{Im}(\mu_m))]$.

9. The apparatus of claim 1, wherein said at least one metamaterial or dielectric material has a spherical or spheroidal shape.

10. The apparatus of claim 9, wherein said at least one metamaterial has a relative magnetic permeability $\mu_m$ such that $\mathrm{Re}(\mu_m)$ is negative and approximate to the first order by $$\mu_m = -\frac{1+L}{L}$$

wherein L is a positive integer which identifies a magnetic plasmonic regime.

11. The apparatus of claim 9, wherein said at least one metamaterial has a relative magnetic permeability $\mu_m$ such that $\mathrm{Im}(\mu_m)$ is less than 0.3.

12. The apparatus of claim 11, wherein said at least one metamaterial has a relative magnetic permeability $\mu_m$ such that $\mathrm{Im}(\mu_m)$ is less than 0.1.

13. The apparatus of claim 9, wherein the relative dielectric permittivity $\varepsilon_d$ of said at least one dielectric material with relative magnetic permeability $\mu_m=1$ satisfies the equation:

$$\varphi_L^{(1)}(k_m\rho_m) - \mu_m\varphi_L^{(1)}(k_d\rho_m) = 0.$$

wherein $$\varphi_L^{(1)}(\xi) = \left(d[\xi j_L(\xi)]/d\xi\right)/j_L(\xi),$$

$j_L$ are spherical Bessel functions, $\xi=k_m\rho_m$, $\rho_m$ is the radius of the sphere, $k_m=\sqrt{\epsilon_m\mu_m}k_0$ and $k_d=\sqrt{\epsilon_d}k_0$ with $k_0=\omega/c$, where $\omega=2\pi\nu$ and $\nu$ is a working frequency of the induction means, wherein $\mu_m$ is the relative magnetic permeability of a metamaterial sphere, wherein $\varepsilon_m$ is the dielectric permittivity of an equivalent sphere of said at least one metamaterial resonating at the working frequency, and wherein c is the speed of light.

14. The apparatus of claim 10, wherein the-real value quantity $d_m$ is chosen as a function of a geometry of the at least one metamaterial or dielectric material and said magnetic plasmonic regime or dielectric resonances regime, respectively.

15. The apparatus of claim 1, wherein said at least one metamaterial has a relative magnetic permeability $\mu_m$ such that $\mathrm{Im}(\mu_m)$ is smaller than $10^{-1}$.

16. The apparatus of claim 15, wherein $\mathrm{Im}(\mu_m)$ is smaller than $10^{-2}$ or $10^{-3}$.

17. The apparatus of claim 1, wherein said at least one metamaterial or dielectric material is configured to display at least two resonance frequencies tuned to two different Larmor frequencies of at least two corresponding nuclei of interest.

18. The apparatus of claim 1, wherein the induction means is inserted between said at least one metamaterial or dielectric material and said at least one sample housing.

19. The apparatus of claim 1, wherein the real value quantities $d_s$ and $d_m$ are both positive.

20. The apparatus of claim 1, wherein the at least one metamaterial or dielectric material is a metamaterial.

21. The apparatus of claim 1, wherein the at least one metamaterial or dielectric material is a dielectric material.

* * * * *